United States Patent
Hatakeyama et al.

(10) Patent No.: US 11,286,320 B2
(45) Date of Patent: *Mar. 29, 2022

(54) POLYMERIZABLE MONOMER, POLYMER COMPOUND FOR CONDUCTIVE POLYMER, AND METHOD FOR PRODUCING THE POLYMER COMPOUND

(71) Applicant: SHIN-ETSU CHEMICAL CO., LTD., Tokyo (JP)

(72) Inventors: Jun Hatakeyama, Joetsu (JP); Takayuki Nagasawa, Joetsu (JP); Koji Hasegawa, Joetsu (JP); Masayoshi Sagehashi, Joetsu (JP); Masahiro Fukushima, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 64 days.

This patent is subject to a terminal disclaimer.

(21) Appl. No.: 16/744,594

(22) Filed: Jan. 16, 2020

(65) Prior Publication Data
US 2020/0247926 A1 Aug. 6, 2020

(30) Foreign Application Priority Data
Jan. 31, 2019 (JP) .............................. JP2019-15515

(51) Int. Cl.
C08F 212/14 (2006.01)
C08F 220/68 (2006.01)
C08F 220/38 (2006.01)
C07C 43/23 (2006.01)

(52) U.S. Cl.
CPC ............ *C08F 212/22* (2020.02); *C07C 43/23* (2013.01); *C08F 212/24* (2020.02); *C08F 212/30* (2020.02); *C08F 220/382* (2020.02); *C08F 220/387* (2020.02); *C08F 220/68* (2013.01)

(58) Field of Classification Search
CPC .................................................. C08F 212/24
See application file for complete search history.

(56) References Cited

U.S. PATENT DOCUMENTS

| | | | |
|---|---|---|---|
| 8,057,708 B2 | 11/2011 | Hsu | |
| 2004/0005512 A1* | 1/2004 | Mizutani | G03F 7/0046 430/270.1 |
| 2008/0020289 A1* | 1/2008 | Hatakeyama | G03F 7/0397 430/4 |
| 2014/0178820 A1* | 6/2014 | Hatakeyama | C08F 214/186 430/285.1 |
| 2014/0212810 A1* | 7/2014 | Hatakeyama | G03F 7/0046 430/285.1 |
| 2016/0237307 A1* | 8/2016 | Cheng | C09D 125/18 |
| 2018/0237561 A1 | 8/2018 | Hatakeyama et al. | |
| 2019/0148080 A1* | 5/2019 | Fukui | H01G 9/028 361/525 |
| 2020/0259094 A1* | 8/2020 | Nagasawa | H01L 51/0035 |
| 2021/0200084 A1* | 7/2021 | Park | G03F 7/038 |

FOREIGN PATENT DOCUMENTS

JP 2008-146913 A 6/2008
JP 5264723 B2 8/2013

OTHER PUBLICATIONS

Jun. 17, 2020 Extended European Search Report issued in European Patent Application No. 20152732.2.

\* cited by examiner

*Primary Examiner* — Nicole M. Buie-Hatcher
(74) *Attorney, Agent, or Firm* — Oliff PLC

(57) ABSTRACT

Polymerization reaction is performed using a polymerizable monomer shown by the following general formula (1) and at least one monomer selected from monomers each having a structure of a salt among a lithium salt, a sodium salt, a potassium salt, and a nitrogen compound salt of a fluorosulfonic acid or the like; then, the structure of the salt of the repeating unit of a polymer obtained by the polymerization reaction is changed to the fluorosulfonic acid or the like by ion exchange. Thus, the present invention provides a polymer compound for a conductive polymer and a method for producing the polymer compound which is suitably used as a dopant for a fuel cell and a conductive material, and which is a copolymer containing a repeating unit of styrene having a 3,3,3-trifluoro-2-hydroxy-2-trifluoromethylisobutyl ether group, and a repeating unit having any of a fluorosulfonic acid, a fluorosulfonimide group, and a n-carbonyl-fluorosulfonamide group.

(1)

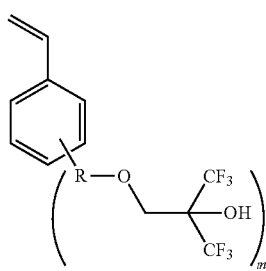

4 Claims, No Drawings

POLYMERIZABLE MONOMER, POLYMER COMPOUND FOR CONDUCTIVE POLYMER, AND METHOD FOR PRODUCING THE POLYMER COMPOUND

TECHNICAL FIELD

The present invention relates to a polymerizable monomer, a polymer compound for a conductive polymer, and a method for producing the polymer compound.

BACKGROUND ART

A sulfo group-containing polymer has been used as a dopant polymer of a fuel cell or a conductive polymer. Vinyl perfluoroalkyl ether sulfonic acid represented by Nafion® has widely been used for fuel cells, and polymers of vinyl sulfonic acid or styrene sulfonic acid have widely been used as dopant polymers for conductive polymers (Patent Document 1). A fluorinated acid polymer in which a proton is substituted by a cation has been proposed as a dopant polymer; particularly, a dopant of a styrene derivative having a lithium salt of bisfluoroalkylsulfonylimide has been shown (Patent Document 2).

Although vinyl perfluoroalkyl ether sulfonic acid has chemically high stability and is excellent in durability, its glass transition point is low, and when the fuel cell using the same is exposed to a high temperature, there is a problem that the polymer undergoes heat flow whereby ion conductivity is lowered. A styrene having bisfluoroalkylsulfonylimide has the similar problem. In order to enhance the ion conductivity of the derivative, a super strong acid polymer represented by a sulfo group fluorinated at the α-position is effective, but along with this, a material having a high glass transition point and being chemically stable has not yet been found out.

Conductive polymers having conjugated double bonds such as polythiophene, polyaniline, and polypyrrole do not show electric conductivity by themselves, but electric conductivity is developed by doping with a strong acid such as sulfonic acid. Polystyrenesulfonic acid (PSS) has been most frequently used as a dopant. This is because the electric conductivity becomes the highest by PSS doping.

The PSS is a water-soluble resin and hardly soluble in an organic solvent. Accordingly, the polythiophene using the PSS as a dopant is also water-soluble.

The polythiophene using the PSS as a dopant has high electric conductivity and high transparency, so that it is expected to be a conductive film for organic EL lighting replacing ITO (indium-tin oxide). However, a luminous body of an organic EL chemically changes due to moisture and does not emit light. That is, when a conductive film of a water-soluble resin is used for an organic EL, the resin contains water, so that there is a problem that the emission lifetime of the organic EL is shortened.

CITATION LIST

Patent Literature

Patent Document 1: Japanese Unexamined Patent Application Publication No. 2008-146913
Patent Document 2: Japanese Patent No. 5264723

SUMMARY OF INVENTION

Technical Problem

The present invention has been made in view of the above circumstances, and an object thereof is to provide a polymer compound for a conductive polymer, which is suitably used as a dopant for a fuel cell and a conductive material, and which is a copolymer containing: a repeating unit having any of a fluorosulfonic acid, a fluorosulfonimide group, and a n-carbonyl-fluoro-sulfonamide group; and a repeating unit of styrene having a 3,3,3-trifluoro-2-hydroxy-2-trifluoromethyl(hexafluoroalcohol: HFA)isobutyl ether group. Another object of the present invention is to provide a method for producing such a polymer compound for a conductive polymer.

Solution to Problem

To achieve the object, the present invention provides a polymerizable monomer shown by the following general formula (1):

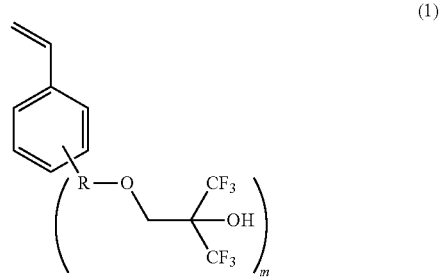

wherein R represents a single bond, a methylene group, or an ethylidene group, and "m" represents 1 or 2.

The inventive polymerizable monomer is a raw-material monomer for a specific polymer compound for a conductive polymer, which is soluble in an organic solvent and suitably used as a dopant for a fuel cell and a conductive material.

Moreover, the present invention provides a polymer compound for a conductive polymer, comprising a copolymer containing:

a repeating unit "a" shown by the following general formula (2); and at least one repeating unit "b" selected from repeating units of monomers respectively having a fluorosulfonic acid, a fluorosulfonimide group, and a n-carbonyl-fluoro-sulfonamide group, wherein the polymer compound for a conductive polymer has a weight average molecular weight in a range of 1,000 to 500,000,

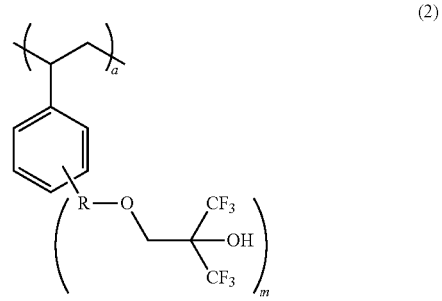

wherein R represents a single bond, a methylene group, or an ethylidene group; "m" represents 1 or 2; and "a" represents $0<a<1.0$.

The inventive polymer compound for a conductive polymer is soluble in an organic solvent, and suitably used as a dopant for a fuel cell and a conductive material.

Preferably, the repeating unit having a fluorosulfonic acid is shown by any of b1 to b5 in the following general formula (3), the repeating unit having a fluorosulfonimide group is shown by b6, and the repeating unit having a n-carbonyl-fluoro-sulfonamide group is shown by b7:

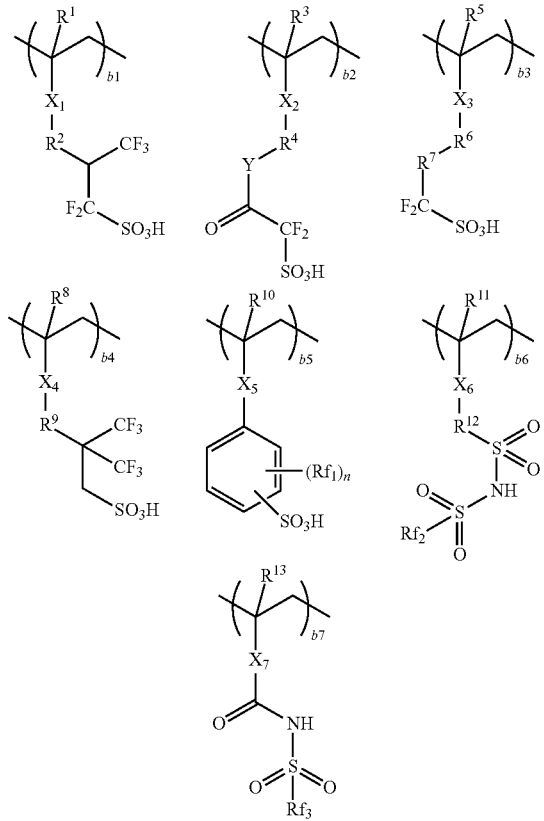

(3)

wherein $R^1$, $R^3$, $R^5$, $R^8$, $R^1$, $R^{11}$, and $R^{13}$ each independently represent a hydrogen atom or a methyl group; $R^2$, $R^4$, $R^6$, $R^9$, and $R^{12}$ each independently represent any of a single bond and a linear, branched, or cyclic hydrocarbon group having 1 to 12 carbon atoms optionally having one or both of an ether group and an ester group; $R^7$ represents a linear or branched alkylene group having 1 to 4 carbon atoms, and one or two hydrogen atoms in $R^7$ are optionally substituted with a fluorine atom; $X_1$, $X_2$, $X_3$, $X_4$, $X_6$, and $X_7$ each independently represent any of a single bond, a phenylene group, a naphthylene group, an ether group, an ester group, and an amide group; $X_5$ represents any of a single bond, an ether group, and an ester group; Y represents any of an ether group and an amino group which optionally contains any of a hydrogen atom and a linear, branched, or cyclic hydrocarbon group having 1 to 12 carbon atoms optionally containing a hetero atom; $Rf_1$ represents a fluorine atom or a trifluoromethyl group; $Rf_2$ and $Rf_3$ each represent a linear or branched alkyl group having 1 to 4 carbon atoms with one or more fluorine atoms, or a phenyl group substituted with a fluorine atom or a trifluoromethyl group; "n" represents an integer of 1 to 4; and b1, b2, b3, b4, b5, b6, and b7 satisfy $0 \le b1 < 1.0$, $0 \le b2 < 1.0$, $0 \le b3 < 1.0$, $0 \le b4 < 1.0$, $0 \le b5 < 1.0$, $0 \le b6 < 1.0$, $0 \le b7 < 1.0$, and $0 < b1+b2+b3+b4+b5+b6+b7 < 1.0$.

Also preferably, the repeating unit "b" is any of repeating units b1' to b7' shown by the following general formula (4), each of which is a lithium salt, a sodium salt, a potassium salt, or a nitrogen compound salt:

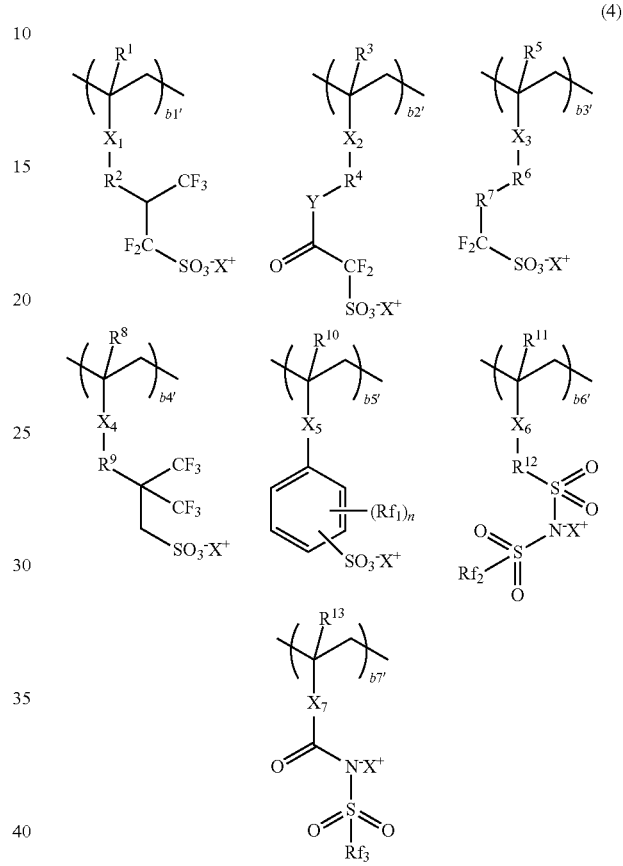

(4)

wherein R, $R^3$, $R^5$, $R^8$, $R^{10}$, $R^{11}$, and $R^{13}$ each independently represent a hydrogen atom or a methyl group; $R^2$, $R^4$, $R^6$, $R^9$, and $R^{12}$ each independently represent any of a single bond and a linear, branched, or cyclic hydrocarbon group having 1 to 12 carbon atoms optionally having one or both of an ether group and an ester group; $R^7$ represents a linear or branched alkylene group having 1 to 4 carbon atoms, and one or two hydrogen atoms in $R^7$ are optionally substituted with a fluorine atom; $X_1$, $X_2$, $X_3$, $X_4$, $X_6$, and $X_7$ each independently represent any of a single bond, a phenylene group, a naphthylene group, an ether group, an ester group, and an amide group; $X_5$ represents any of a single bond, an ether group, and an ester group; Y represents any of an ether group and an amino group which optionally contains any of a hydrogen atom and a linear, branched, or cyclic hydrocarbon group having 1 to 12 carbon atoms optionally containing a hetero atom; $Rf_1$ represents a fluorine atom or a trifluoromethyl group; $Rf_2$ and $Rf_3$ each represent a linear or branched alkyl group having 1 to 4 carbon atoms with one or more fluorine atoms, or a phenyl group substituted with a fluorine atom or a trifluoromethyl group; "n" represents an integer of 1 to 4; X represents lithium, sodium, potassium, or a nitrogen compound shown by the following general formula (5); and b1', b2', b3', b4', b5', b6', and b7' satisfy $0 \leq b1' < 1.0$, $0 \leq b2' < 1.0$, $0 \leq b3' < 1.0$, $0 \leq b4' < 1.0$, $0 \leq b5' < 1.0$, $0 \leq b6' < 1.0$, $0 \leq b7' < 1.0$, and $0 < b1'+b2'+b3'+b4'+b5'+b6'+b7' < 1.0$,

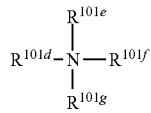

(5)

wherein $R^{101d}$, $R^{101e}$, $R^{101f}$, and $R^{101g}$ each represent a hydrogen atom, a linear, branched, or cyclic alkyl group, alkenyl group, oxoalkyl group, or oxoalkenyl group having 1 to 12 carbon atoms, an aryl group having 6 to 20 carbon atoms, or an aralkyl group or aryloxoalkyl group having 7 to 12 carbon atoms, and a part or all of hydrogen atoms of these groups are optionally substituted with alkoxy groups; and $R^{101d}$ and $R^{101e}$, or $R^{101d}$, $R^{101e}$, and $R^{101f}$, optionally form a ring, and when a ring is formed, $R^{101d}$ and $R^{101e}$, or $R^{101d}$, $R^{101e}$, and $R^{101f}$, represent an alkylene group having 3 to 10 carbon atoms or a heteroaromatic ring having the nitrogen atom in the formula in the ring.

When the repeating unit "b" is particularly as described above, the effects of the present invention are more sufficiently exhibited.

Furthermore, the present invention provides a method for producing a polymer compound for a conductive polymer, comprising:

performing polymerization reaction using a polymerizable monomer shown by the following general formula (1) and at least one monomer selected from monomers each having a structure of a salt among a lithium salt, a sodium salt, a potassium salt, and a nitrogen compound salt of a fluorosulfonic acid, a fluorosulfonimide group, or a n-carbonyl-fluoro-sulfonamide group,

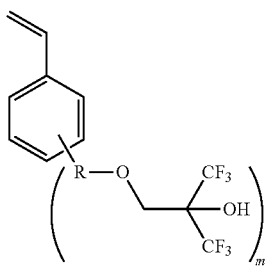

(1)

wherein R represents a single bond, a methylene group, or an ethylidene group, and "m" represents 1 or 2; and changing the structure of the salt of the monomer as a repeating unit of a polymer obtained by the polymerization reaction to the fluorosulfonic acid, the fluorosulfonimide group, or the n-carbonyl-fluoro-sulfonamide group by ion exchange, wherein the polymer compound for a conductive polymer comprises a copolymer containing a repeating unit "a" shown by the following general formula (2) and at least one repeating unit "b" selected from repeating units of monomers respectively having the fluorosulfonic acid, the fluorosulfonimide group, and the n-carbonyl-fluoro-sulfonamide group, and has a weight average molecular weight in a range of 1,000 to 500,000,

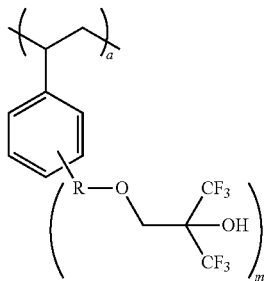

(2)

wherein R and "m" are as defined above, and "a" represents $0 < a < 1.0$.

Such a production method makes it possible to easily produce a polymer compound for a conductive polymer, which is a copolymer composed of the repeating unit "a" shown by the general formula (2) and one or more of the repeating units "b" selected from repeating units of monomers respectively having a fluorosulfonic acid, a fluorosulfonimide group, and a n-carbonyl-fluoro-sulfonamide group, and which has a weight average molecular weight in a range of 1,000 to 500,000.

Advantageous Effects of Invention

As described above, the inventive polymer compound for a conductive polymer is soluble in an organic solvent and suitably used as a dopant for a fuel cell and a conductive material. The polymer compound for a conductive polymer contains a repeating unit of a styrene monomer having a 3,3,3-trifluoro-2-hydroxy-2-trifluoromethylisobutyl ether group and one or more repeating units selected from repeating units of monomers respectively having a fluorosulfonic acid, fluorosulfonimide, and a n-carbonyl-fluoro-sulfonamide group.

By using this polymer compound for a conductive polymer in a fuel cell, a fuel-cell material having high dielectric constant can be formed. In addition, the use as a dopant for a polymer having conjugated double bonds makes it possible to form a conductive film having high transparency, high electric conductivity, and high durability. The inventive polymer compound for a conductive polymer has a 3,3,3-trifluoro-2-hydroxy-2-trifluoromethyl(HFA)isobutyl ether group. The HFA group is highly water repellent. When an aqueous solution of a composite of a polymer containing this group with polythiophene is prepared, water therein evaporates quickly after spin coating, and no moisture is left after the film formation. Thus, the use as a conductive film for organic EL lighting can prevent organic EL devices from deteriorating due to moisture.

Moreover, the inventive production method can facilitate production of the inventive polymer compound for a conductive polymer described above.

DESCRIPTION OF EMBODIMENTS

As mentioned above, it has been desired to develop a polymer compound for a conductive polymer, which has a specific super strong acid(s) and is suitably used as a dopant for a fuel cell and a conductive material.

In a case of using a water-soluble conductive polymer containing water which causes deterioration of an organic EL device, it is necessary to form a film that prevents the device deterioration by reducing the water content as much as possible. Hence, starting from polystyrenesulfonic acid, which is a highly hydrophilic dopant, the present inventors have tried to develop a dopant polymer from which water is likely to evaporate. As a result, the present inventors have found that a dopant polymer with a fluorine-containing super strong acid such as a fluorosulfonic acid, a fluorosulfonimide group, and a fluorosulfonamide group is effective in extending the lifetime of organic EL devices. Besides the super strong acid portion, the inventors have further found that introducing an HFA group with a specific structure increases the water evaporation speed and extends the lifetime of organic EL devices. Thereby, the present invention has been accomplished.

That is, the present invention provides a polymerizable monomer shown by the following general formula (1):

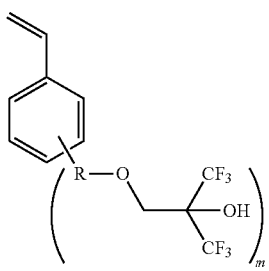

(1)

wherein R represents a single bond, a methylene group, or an ethylidene group, and "m" represents 1 or 2.

Moreover, the present invention provides a polymer compound for a conductive polymer, comprising a copolymer containing:

a repeating unit "a" shown by the following general formula (2); and at least one repeating unit "b" selected from repeating units of monomers respectively having a fluorosulfonic acid, a fluorosulfonimide group, and a n-carbonyl-fluoro-sulfonamide group, wherein the polymer compound for a conductive polymer has a weight average molecular weight in a range of 1,000 to 500,000,

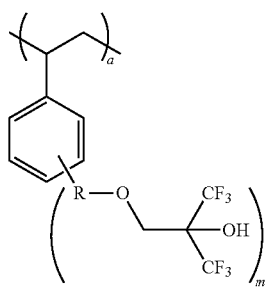

(2)

wherein R represents a single bond, a methylene group, or an ethylidene group; "m" represents 1 or 2; and "a" represents 0<a<1.0.

Further, the present invention provides a method for producing a polymer compound for a conductive polymer, comprising:

performing polymerization reaction using a polymerizable monomer shown by the following general formula (1) and at least one monomer selected from monomers each having a structure of a salt among a lithium salt, a sodium salt, a potassium salt, and a nitrogen compound salt of a fluorosulfonic acid, a fluorosulfonimide group, or a n-carbonyl-fluoro-sulfonamide group,

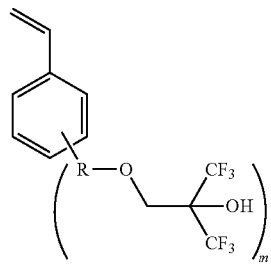

(1)

wherein R represents a single bond, a methylene group, or an ethylidene group, and "m" represents 1 or 2; and changing the structure of the salt of the monomer as a repeating unit of a polymer obtained by the polymerization reaction to the fluorosulfonic acid, the fluorosulfonimide group, or the n-carbonyl-fluoro-sulfonamide group by ion exchange, wherein the polymer compound for a conductive polymer comprises a copolymer containing a repeating unit "a" shown by the following general formula (2) and at least one repeating unit "b" selected from repeating units of monomers respectively having the fluorosulfonic acid, the fluorosulfonimide group, and the n-carbonyl-fluoro-sulfonamide group, and has a weight average molecular weight in a range of 1,000 to 500,000,

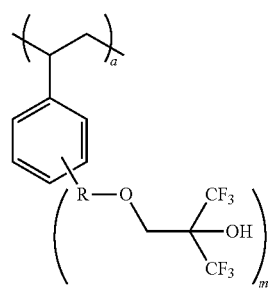

(2)

wherein R and "m" are as defined above, and "a" represents 0<a<1.0.

The polymerizable monomer for introducing an HFA group with a specific structure is shown by the following general formula (1):

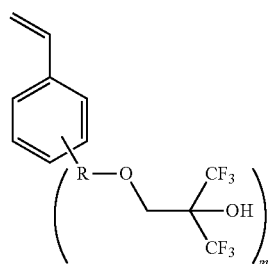

(1)

where R represents a single bond, a methylene group, an ethylidene group, or an isopropylidene group, and "m" represents 1 or 2.

The monomer shown by the general formula (1) can be specifically exemplified as follows.

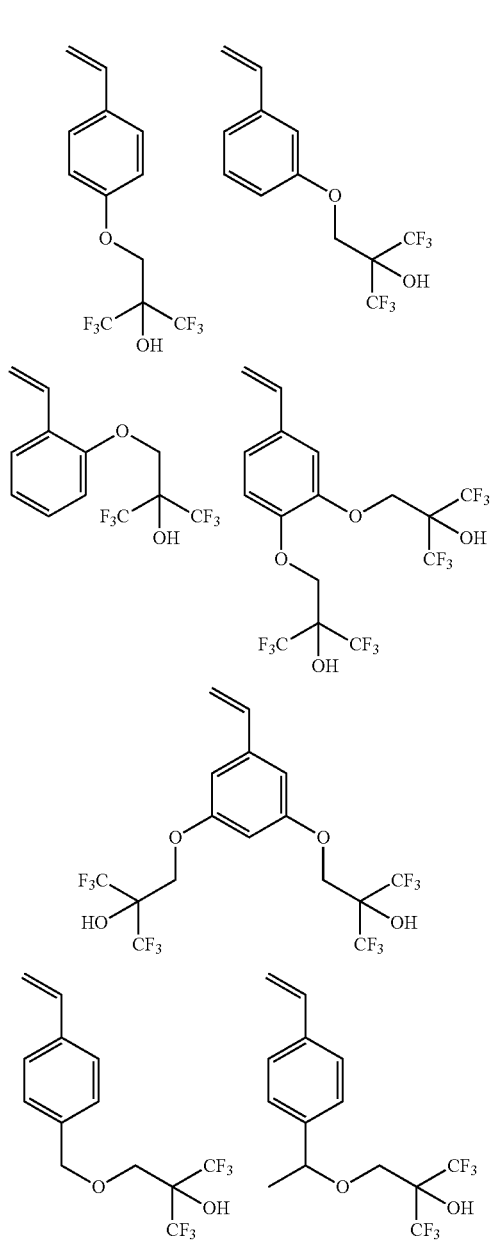

The method for producing the monomer shown by the general formula (1) is not limited to a specific production method. The monomer shown by the general formula (1) can be produced, for example, by synthesis methods to be described later in Examples.

A polymer compound for a conductive polymer can be obtained by copolymerizing the polymerizable monomer shown by the general formula (1) with at least one monomer selected from monomers each having a structure of a salt among a lithium salt, a sodium salt, a potassium salt, and an ammonium salt of a fluorosulfonic acid, a fluorosulfonimide group, or a n-carbonyl-fluoro-sulfonamide group. This polymer compound for a conductive polymer is preferably a copolymer containing a repeating unit "a" shown by the general formula (2) and any of repeating units shown by the following general formula (4).

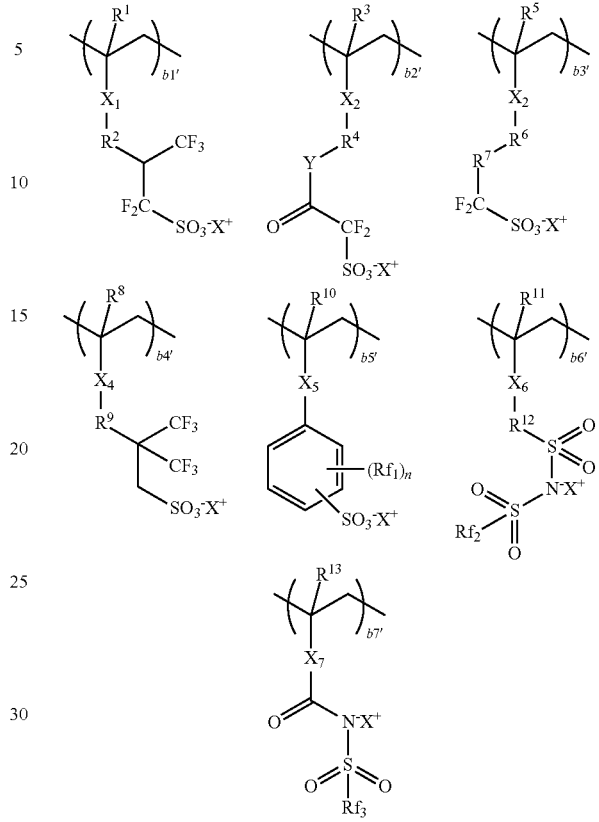

(4)

In the formula (4), $R^1$, $R^3$, $R^5$, $R^8$, $R^{10}$, $R^{11}$, and $R^{13}$ each independently represent a hydrogen atom or a methyl group. $R^2$, $R^4$, $R^6$, $R^9$, and $R^{12}$ each independently represent any of a single bond and a linear, branched, or cyclic hydrocarbon group having 1 to 12 carbon atoms optionally having one or both of an ether group and an ester group. $R^7$ represents a linear or branched alkylene group having 1 to 4 carbon atoms, and one or two hydrogen atoms in $R^7$ are optionally substituted with a fluorine atom. $X_1$, $X_2$, $X_3$, $X_4$, $X_6$, and $X_7$ each independently represent any of a single bond, a phenylene group, a naphthylene group, an ether group, an ester group, and an amide group. $X_5$ represents any of a single bond, an ether group, and an ester group. Y represents any of an ether group and an amino group. This amino group optionally contains any of a hydrogen atom and a linear, branched, or cyclic hydrocarbon group having 1 to 12 carbon atoms optionally containing a hetero atom. $Rf_1$ represents a fluorine atom or a trifluoromethyl group. $Rf_2$ and $Rf_3$ each represent a linear or branched alkyl group having 1 to 4 carbon atoms with one or more fluorine atoms, or a phenyl group substituted with a fluorine atom or a trifluoromethyl group. "n" represents an integer of 1 to 4. X represents lithium, sodium, potassium, or a nitrogen compound shown by the following general formula (5). b1', b2', b3', b4', b5', b6', and b7' satisfy $0 \leq b1' < 1.0$, $0 \leq b2' < 1.0$, $0 \leq b3' < 1.0$, $0 \leq b4' < 1.0$, $0 \leq b5' < 1.0$, $0 \leq b6' < 1.0$, $0 \leq b7' < 1.0$, and $0 < b1'+b2'+b3'+b4'+b5'+b6'+b7' < 1.0$.

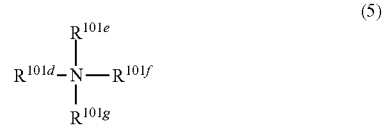

(5)

In the formula (5), $R^{101d}$, $R^{101e}$, $R^{101f}$, and $R^{1019}$ each represent a hydrogen atom, a linear, branched, or cyclic alkyl group, alkenyl group, oxoalkyl group, or oxoalkenyl group having 1 to 12 carbon atoms, an aryl group having 6 to 20 carbon atoms, or an aralkyl group or aryloxoalkyl group having 7 to 12 carbon atoms. A part or all of hydrogen atoms of these groups are optionally substituted with alkoxy groups. $R^{101d}$ and $R^{101e}$, or $R^{101d}$, $R^{101e}$, and $R^{101f}$, optionally form a ring, and when a ring is formed, $R^{101d}$ and $R^{101e}$, or $R^{101d}$, $R^{101e}$, and $R^{101f}$, represent an alkylene group having 3 to 10 carbon atoms or a heteroaromatic ring having the nitrogen atom in the formula in the ring.

By subjecting the copolymer to ion exchange, a polymer compound for a conductive polymer can be obtained which is a copolymer containing: the repeating unit "a" shown by the general formula (2); and at least one repeating unit "b" selected from repeating units of monomers respectively having a fluorosulfonic acid, a fluorosulfonimide group, and a n-carbonyl-fluoro-sulfonamide group. The polymer compound for a conductive polymer has a weight average molecular weight in a range of 1,000 to 500,000. The polymer compound for a conductive polymer having a weight average molecular weight within the range is preferably a copolymer containing the repeating unit "a" shown by the general formula (2) and any of repeating units shown by the following general formula (3).

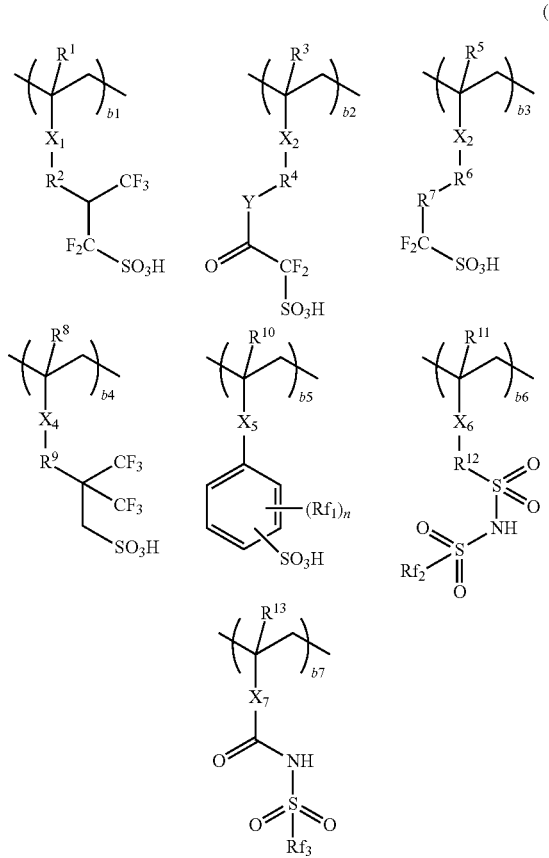

(3)

In the formula (3), $R^1$, $R^3$, $R^5$, $R^8$, $R^{10}$, $R^{11}$, and $R^{13}$ each independently represent a hydrogen atom or a methyl group. $R^2$, $R^4$, $R^6$, $R^9$, and $R^{12}$ each independently represent any of a single bond and a linear, branched, or cyclic hydrocarbon group having 1 to 12 carbon atoms optionally having one or both of an ether group and an ester group. $R^7$ represents a linear or branched alkylene group having 1 to 4 carbon atoms, and one or two hydrogen atoms in $R^7$ are optionally substituted with a fluorine atom. $X_1$, $X_2$, $X_3$, $X_4$, $X_6$, and $X_7$ each independently represent any of a single bond, a phenylene group, a naphthylene group, an ether group, an ester group, and an amide group. $X_5$ represents any of a single bond, an ether group, and an ester group. Y represents any of an ether group and an amino group. This amino group optionally contains any of a hydrogen atom and a linear, branched, or cyclic hydrocarbon group having 1 to 12 carbon atoms optionally containing a hetero atom. $Rf_1$ represents a fluorine atom or a trifluoromethyl group. $Rf_2$ and $Rf_3$ each represent a linear or branched alkyl group having 1 to 4 carbon atoms with one or more fluorine atoms, or a phenyl group substituted with a fluorine atom or a trifluoromethyl group. "n" represents an integer of 1 to 4. b1, b2, b3, b4, b5, b6, and b7 satisfy $0 \le b1 < 1.0$, $0 \le b2 < 1.0$, $0 \le b3 < 1.0$, $0 \le b4 < 1.0$, $0 \le b5 < 1.0$, $0 \le b6 < 1.0$, $0 \le b7 < 1.0$, and $0 < b1+b2+b3+b4+b5+b6+b7 < 1.0$.

A monomer for obtaining the repeating unit b1' can be specifically exemplified as follows.

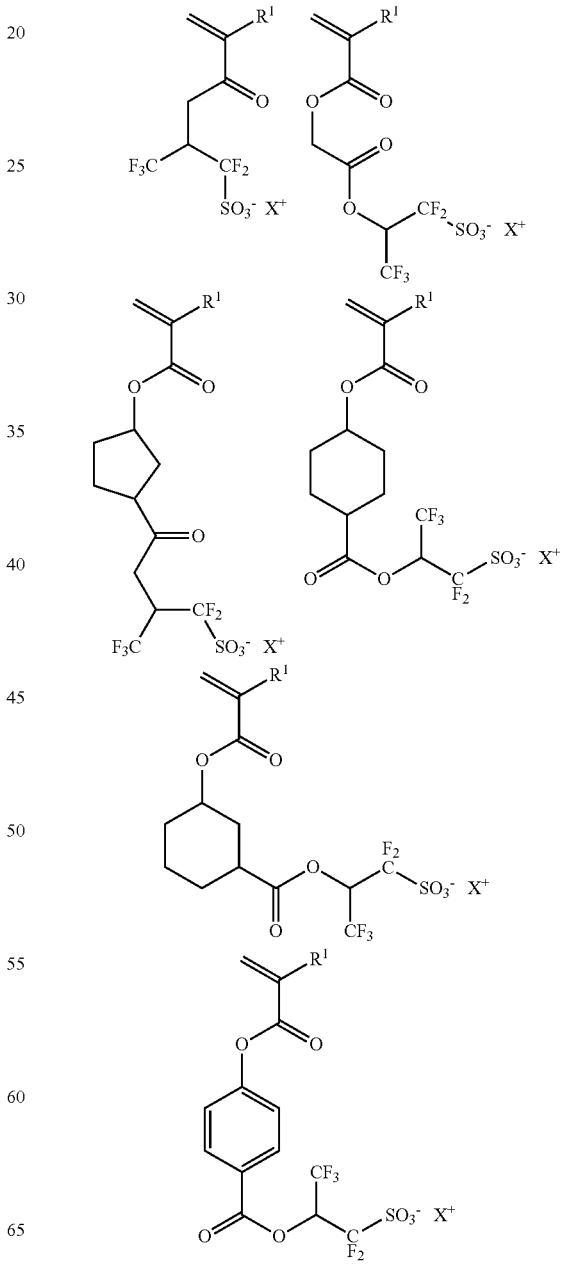

-continued
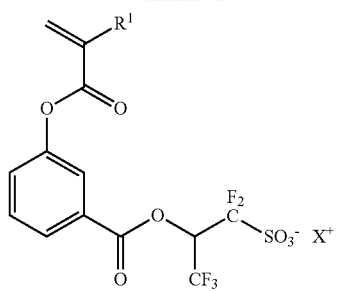
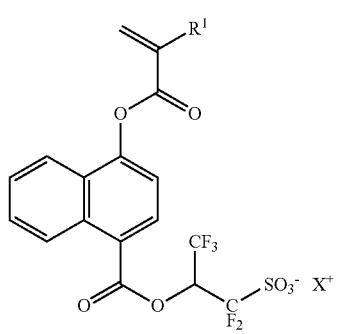
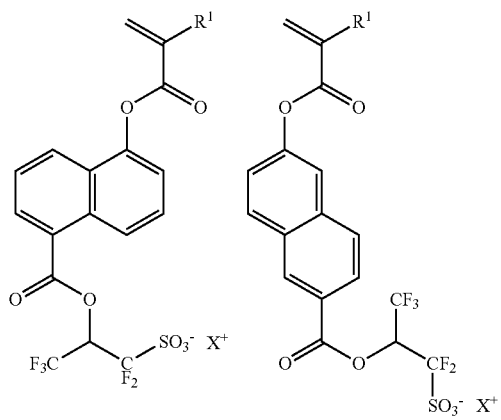
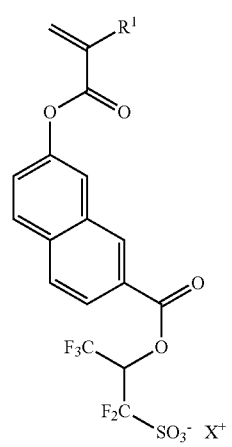
-continued
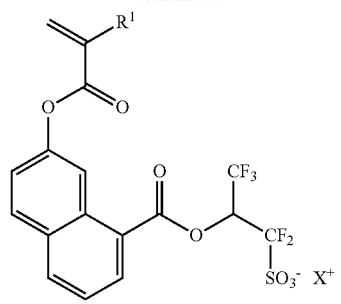
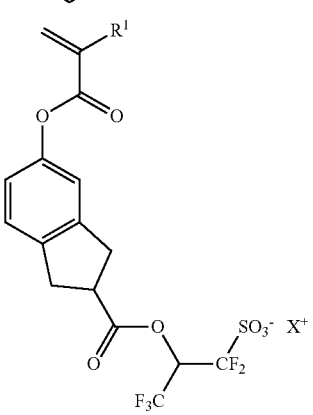
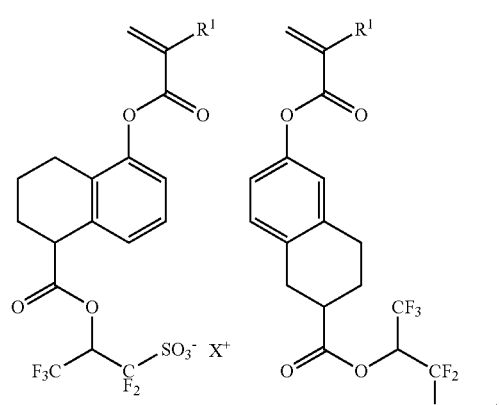
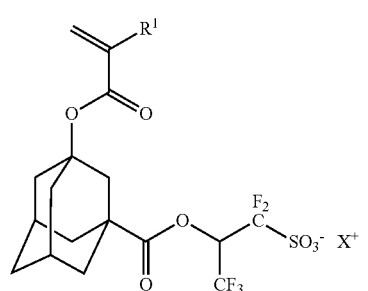
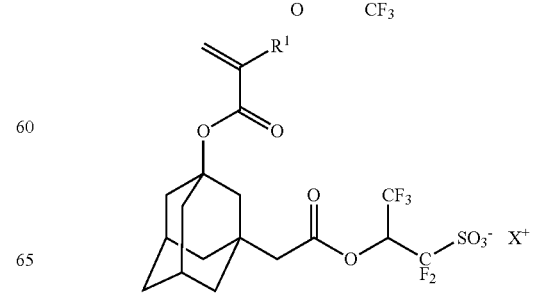

-continued
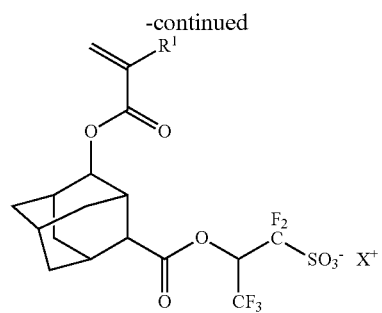
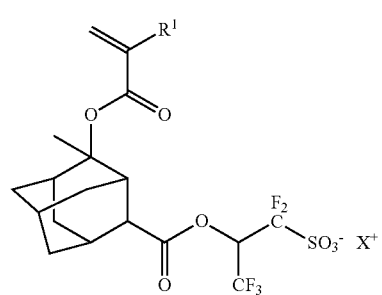
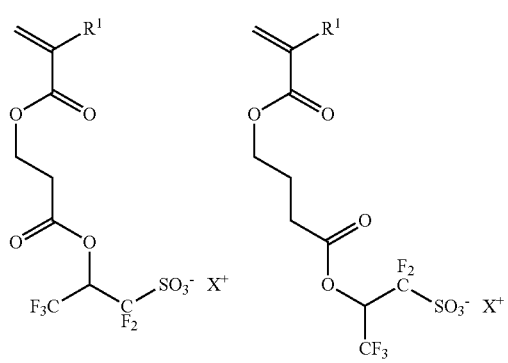
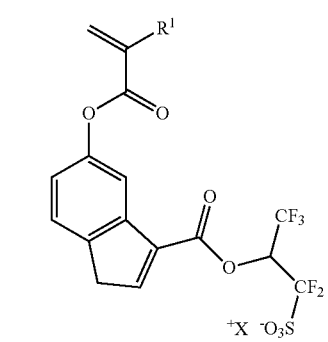
-continued
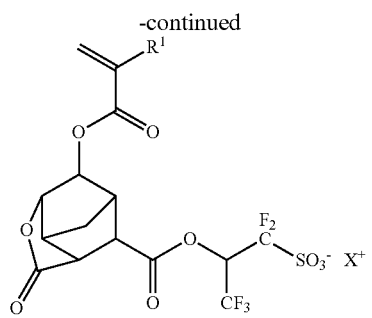
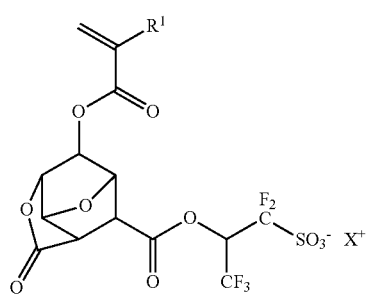
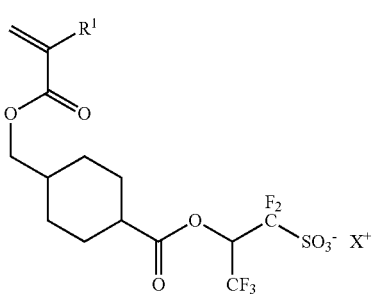
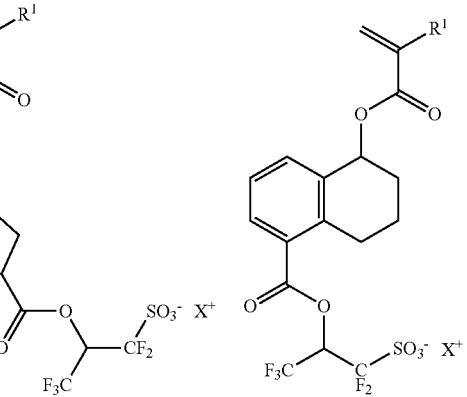

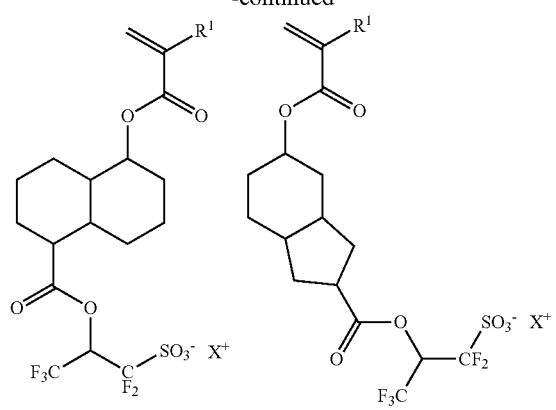
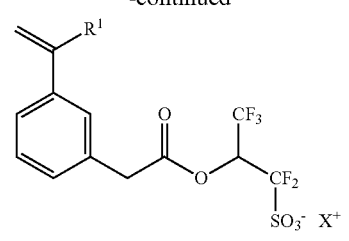
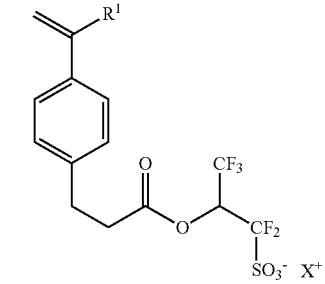
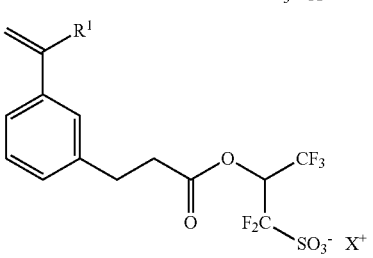
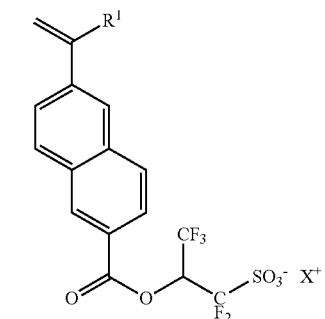
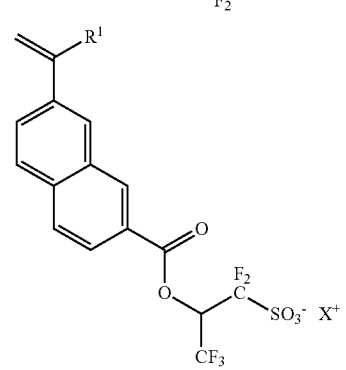
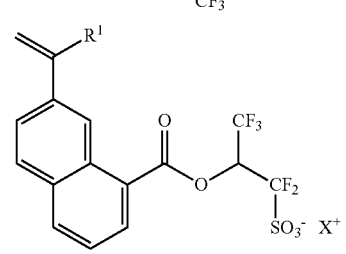

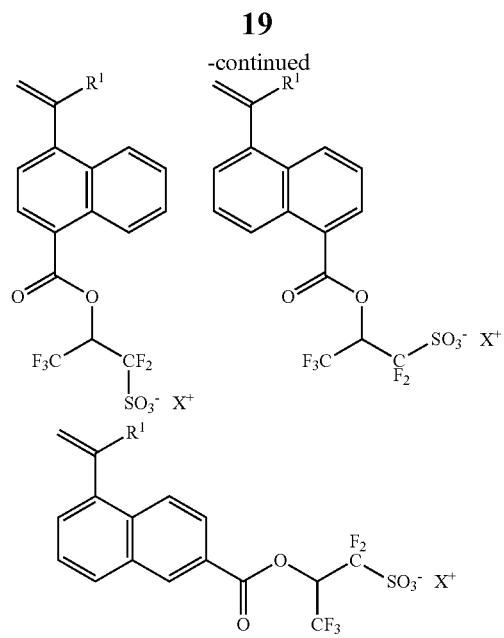
In each formula, $R^1$ is as defined above. X represents Li, Na, K, or an amine compound.
A monomer for obtaining the repeating unit b2' can be specifically exemplified as follows.
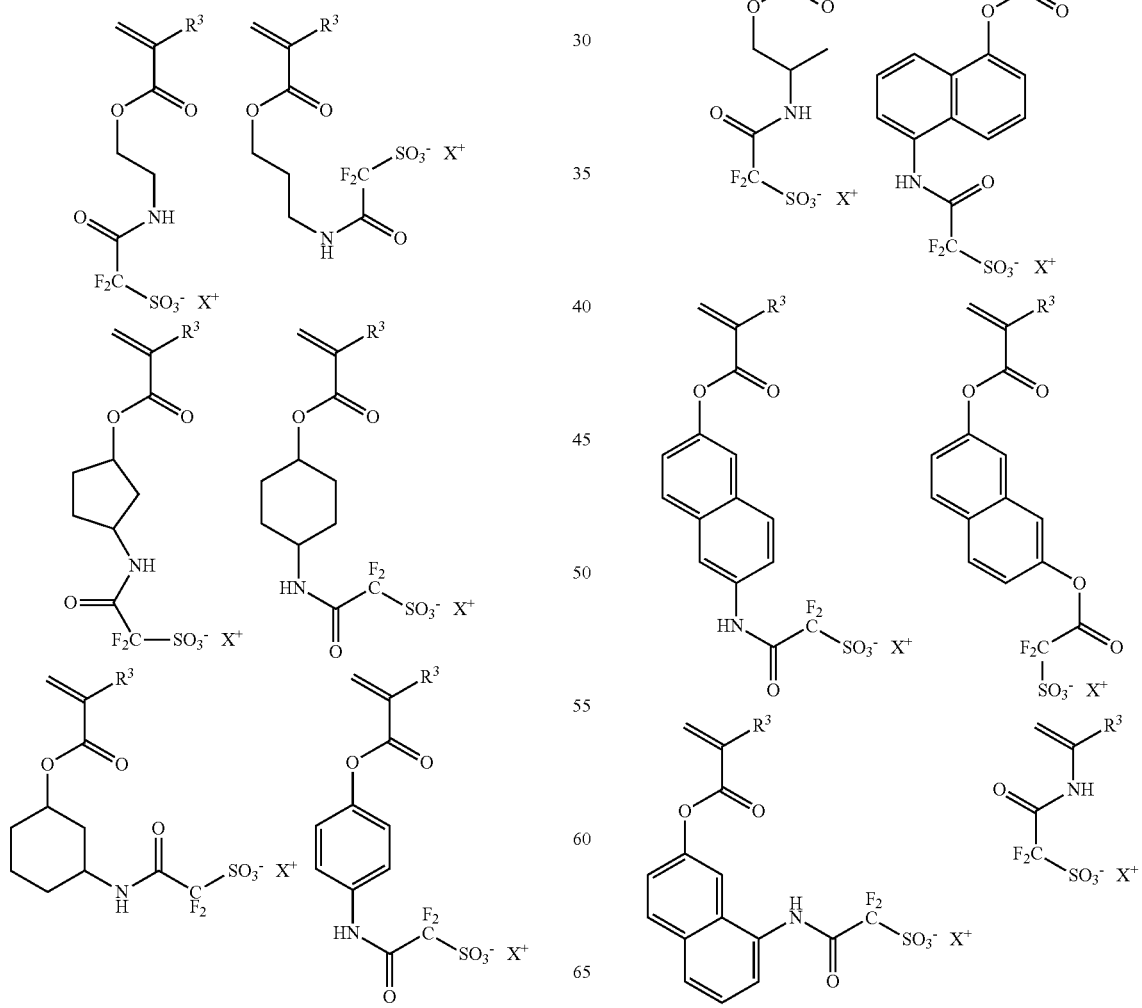

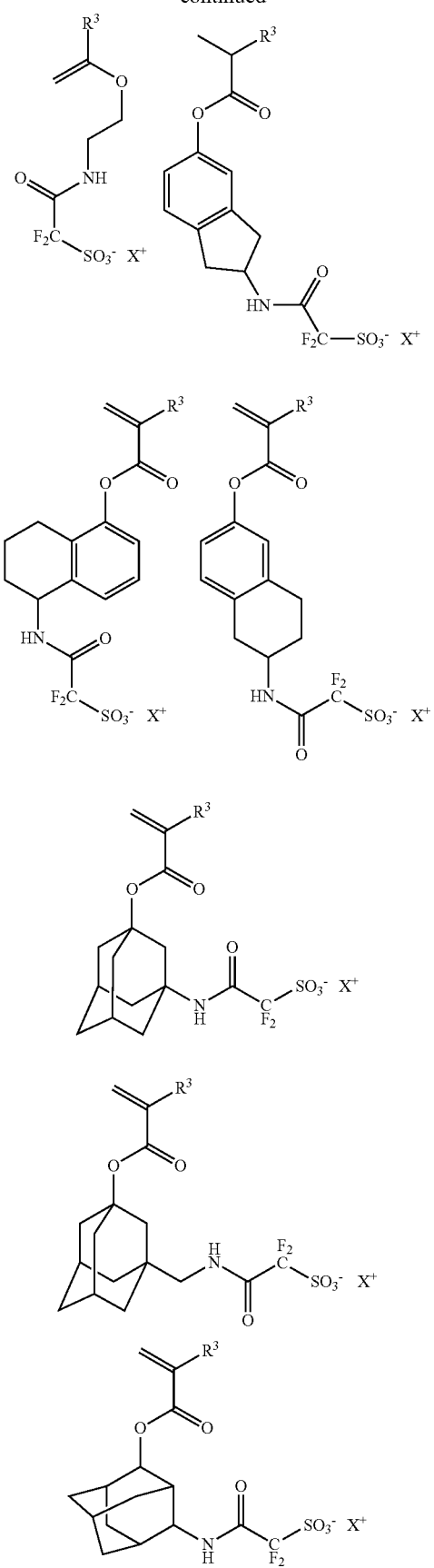
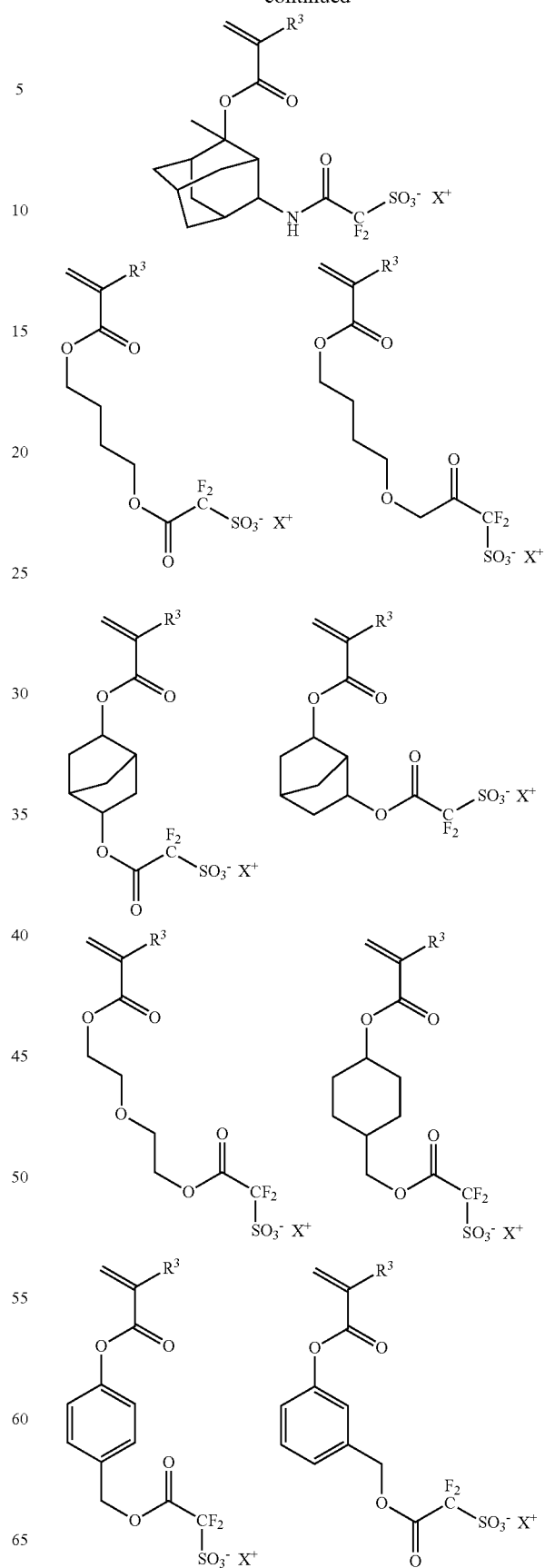

-continued
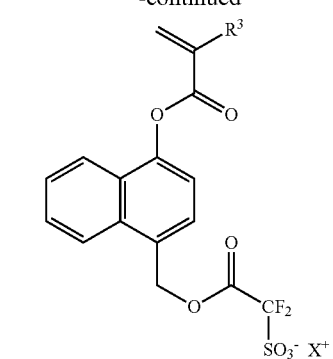
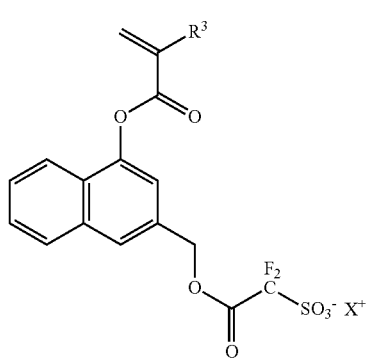
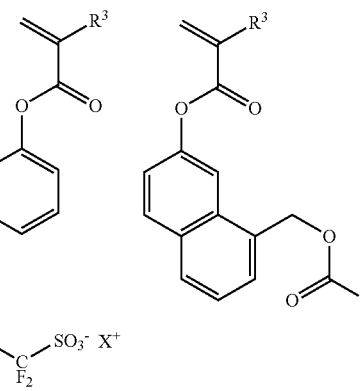
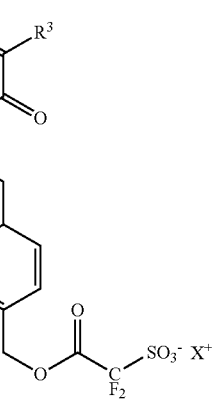
-continued
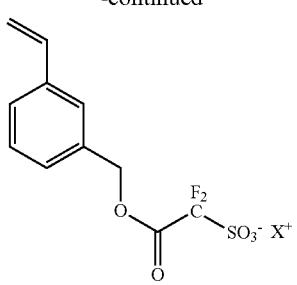
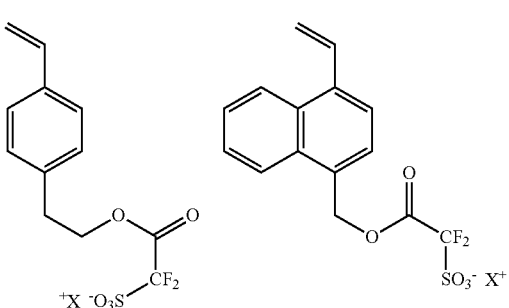
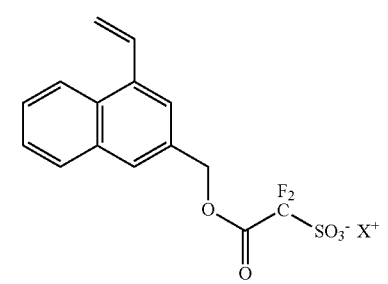
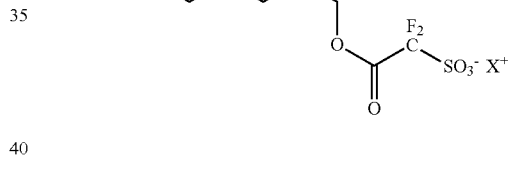
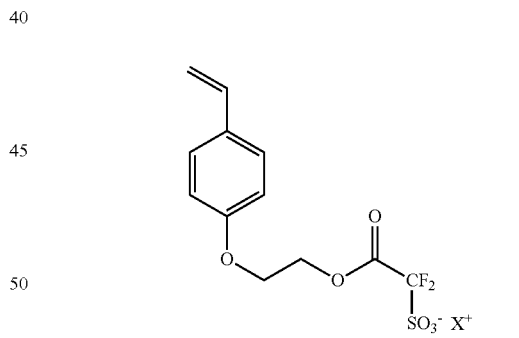
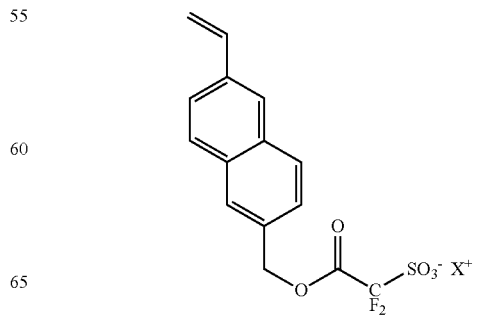

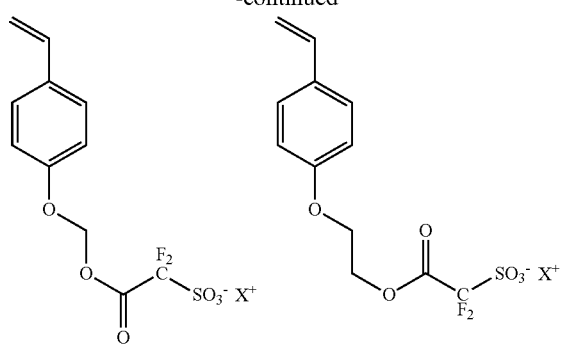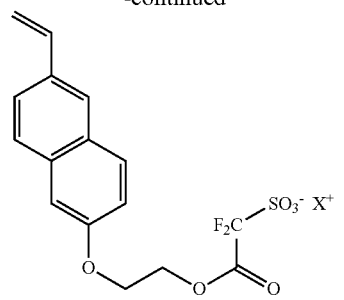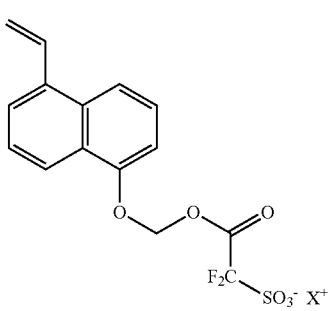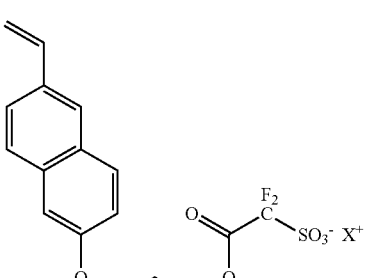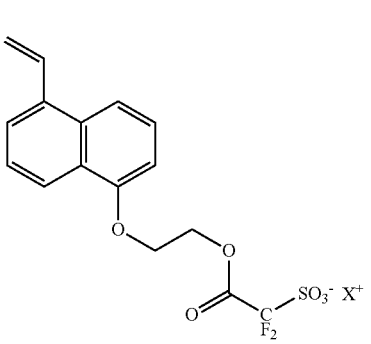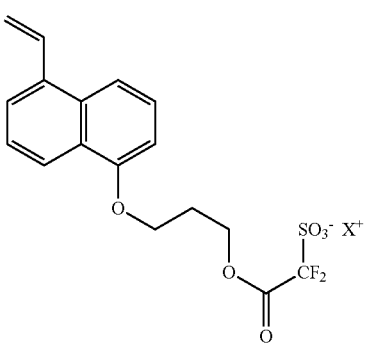

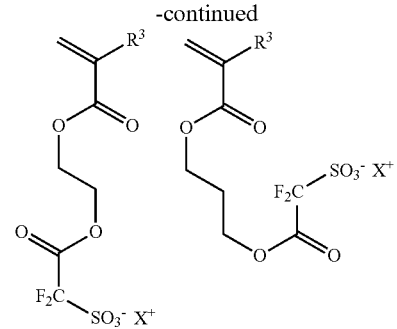
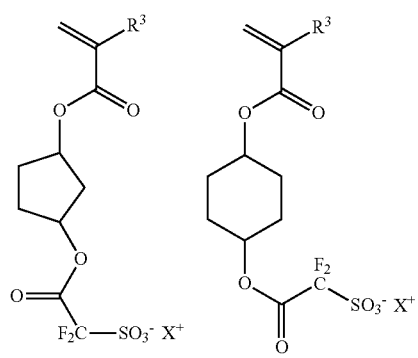
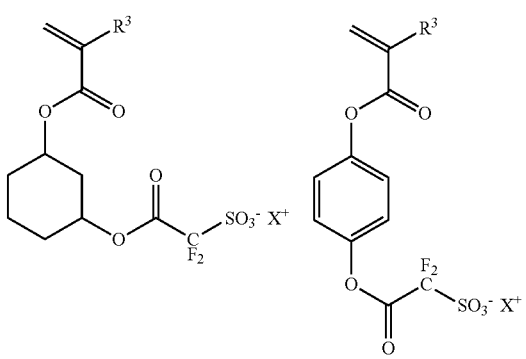
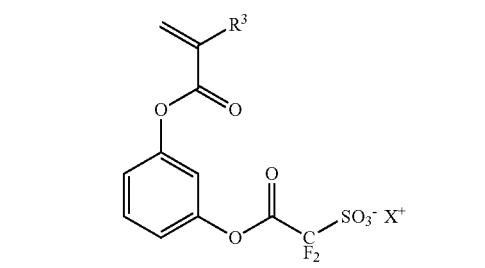
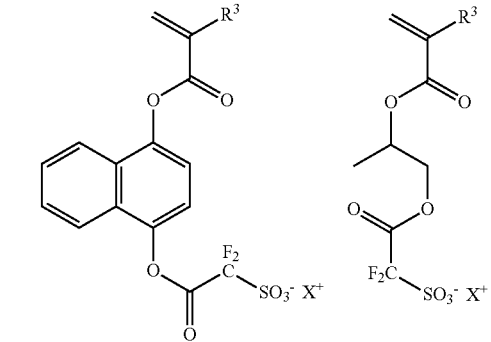
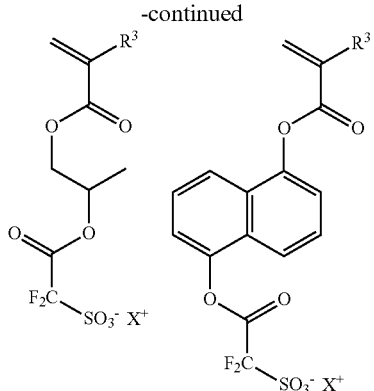
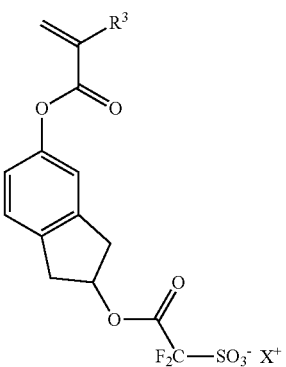

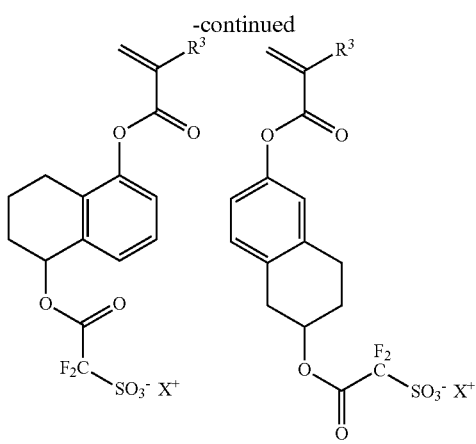
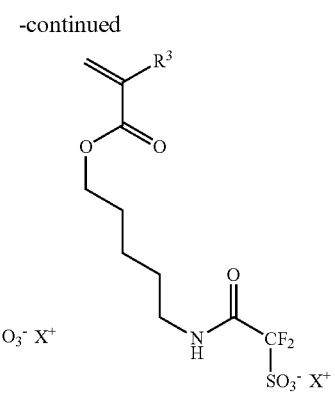
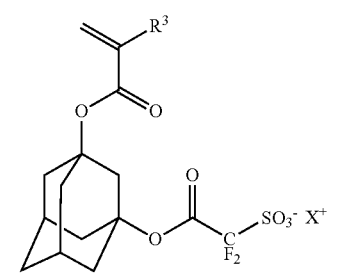
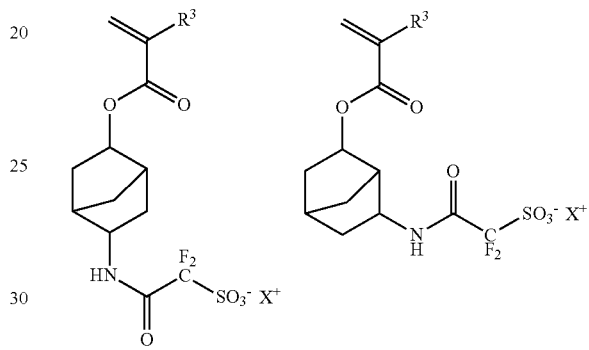
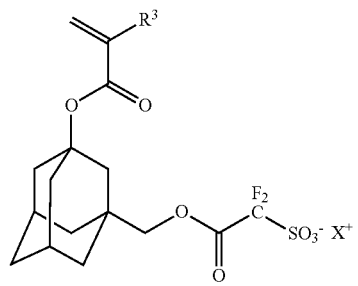
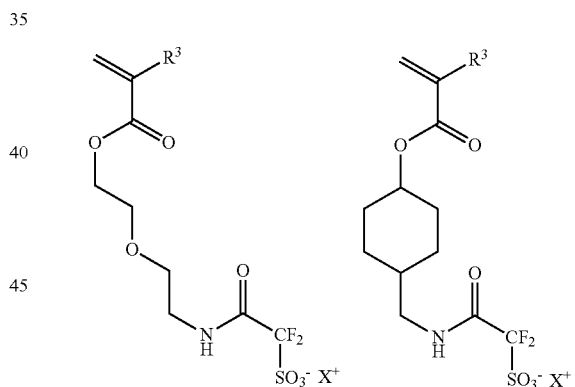
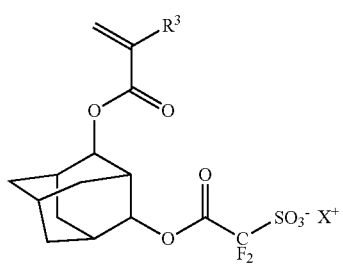
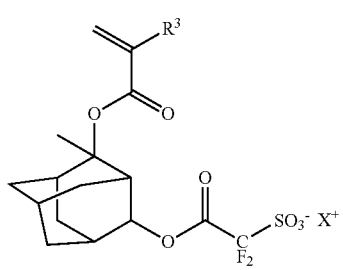
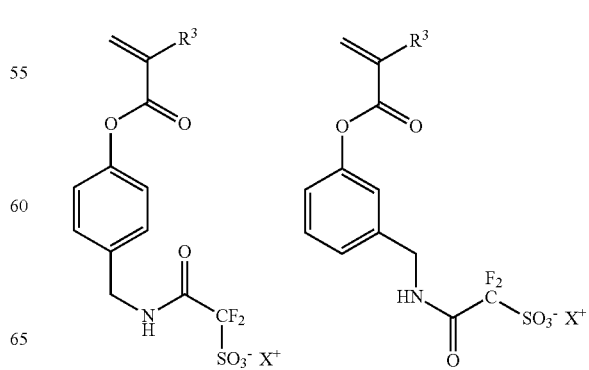

31
-continued
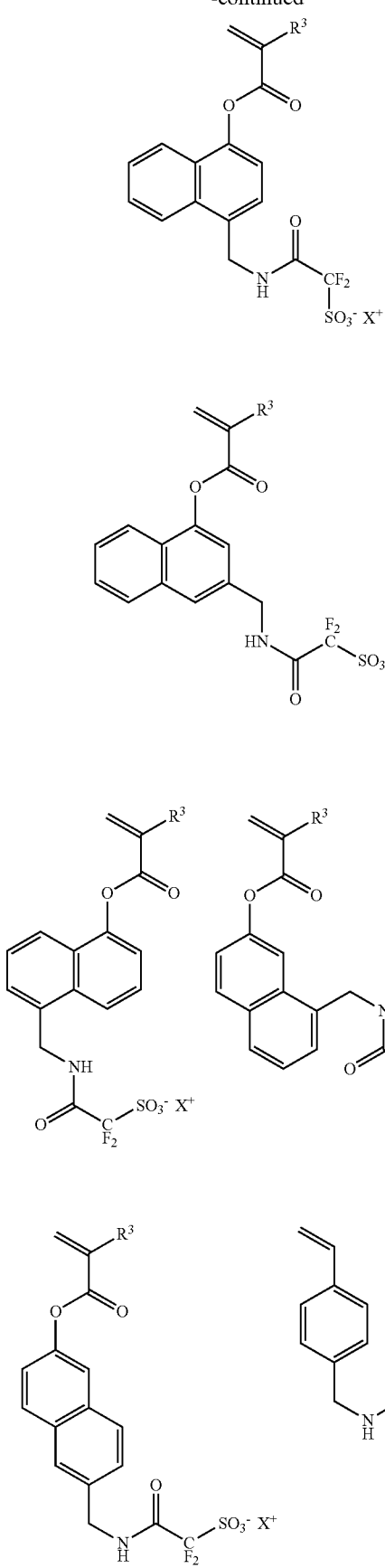
32
-continued
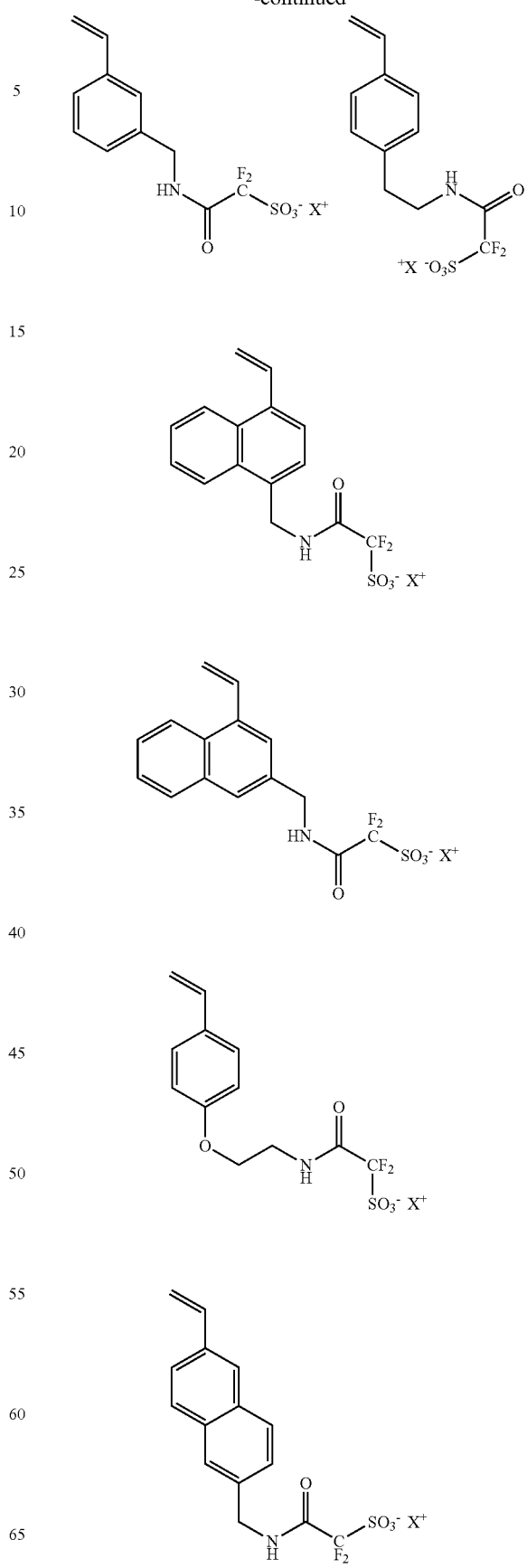

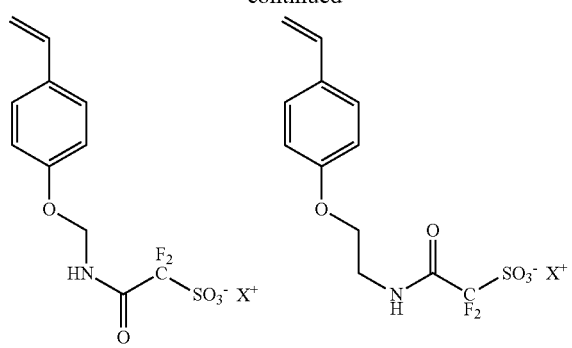
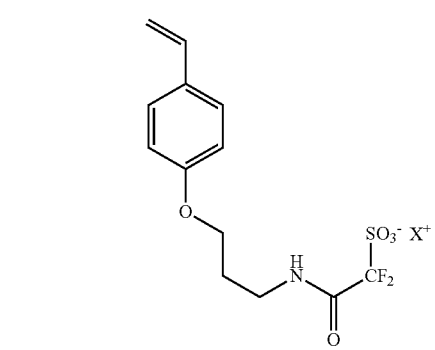
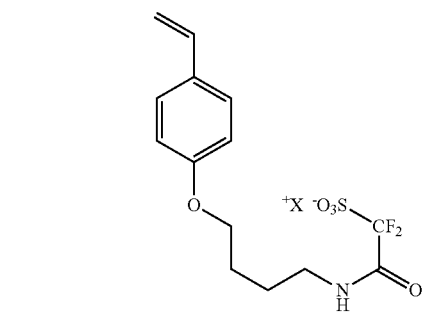
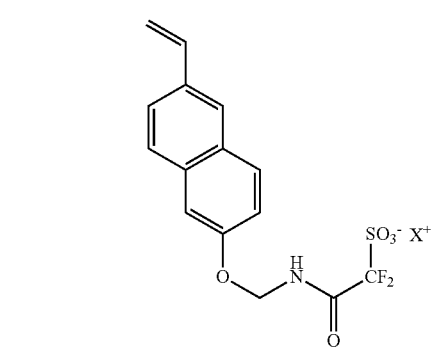
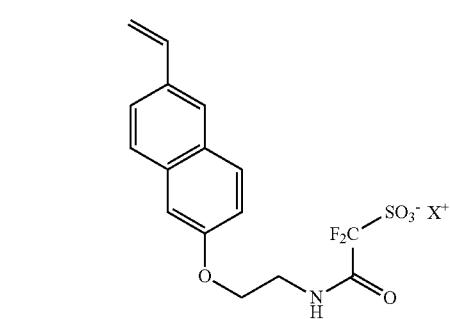
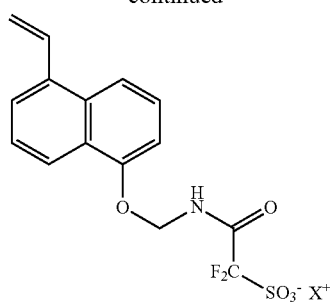
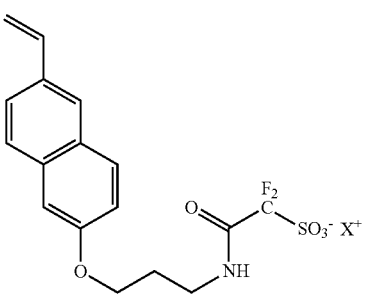
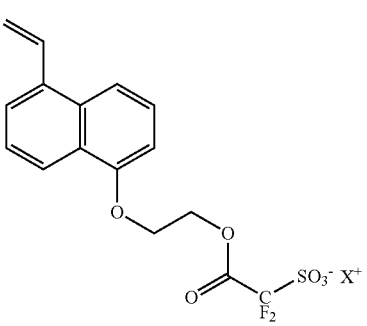
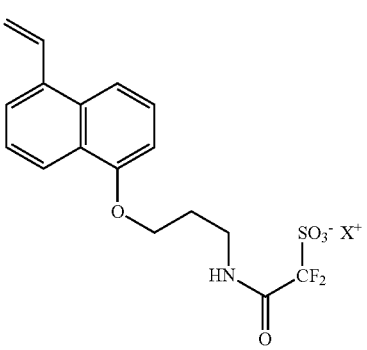
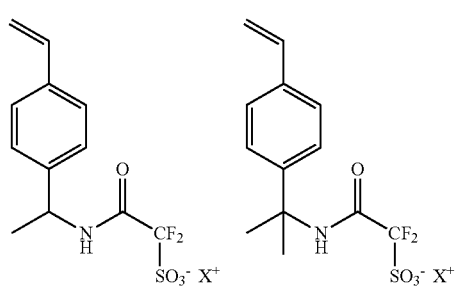

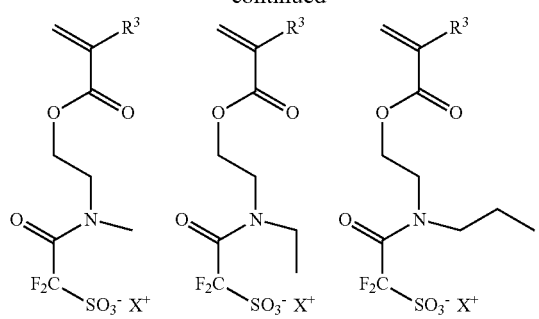
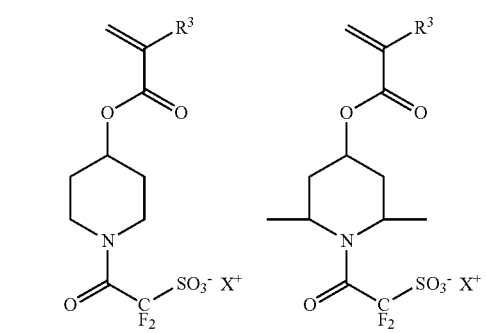
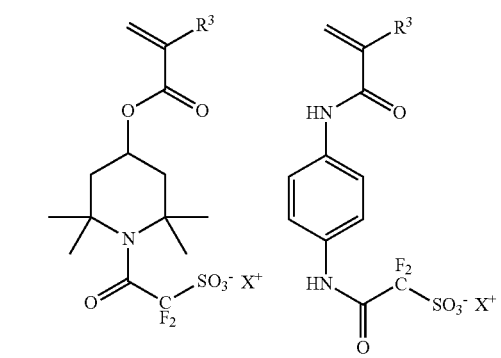
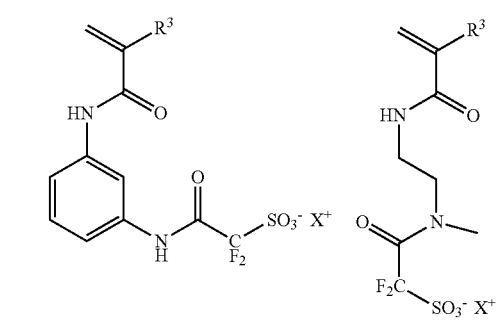
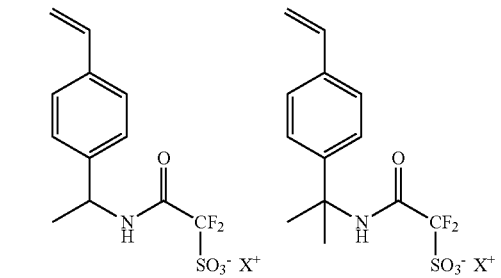
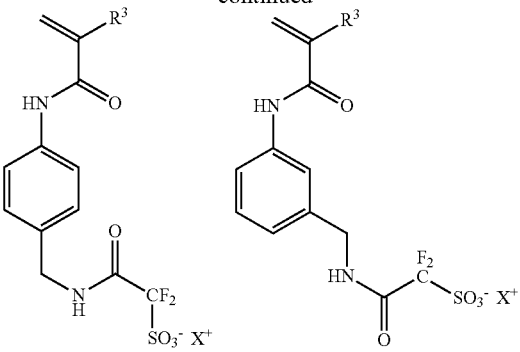
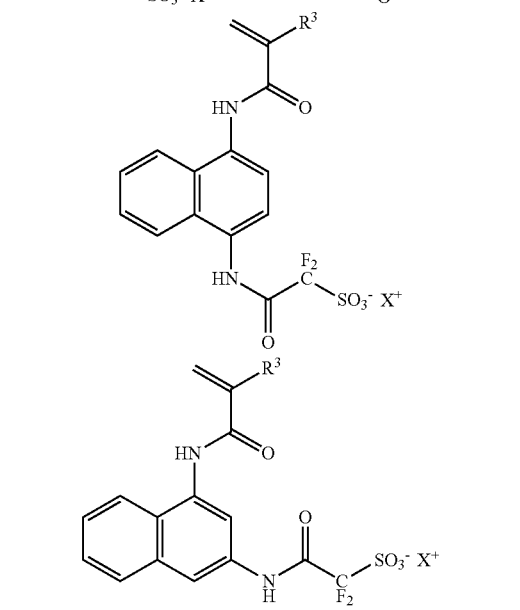
In each formula, R³ is as defined above. X represents Li, Na, K, or an amine compound.
A monomer for providing the repeating unit b3' can be specifically exemplified by the following.
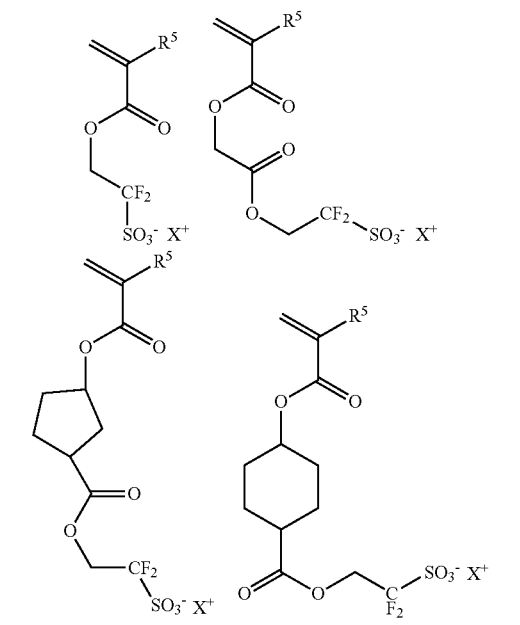

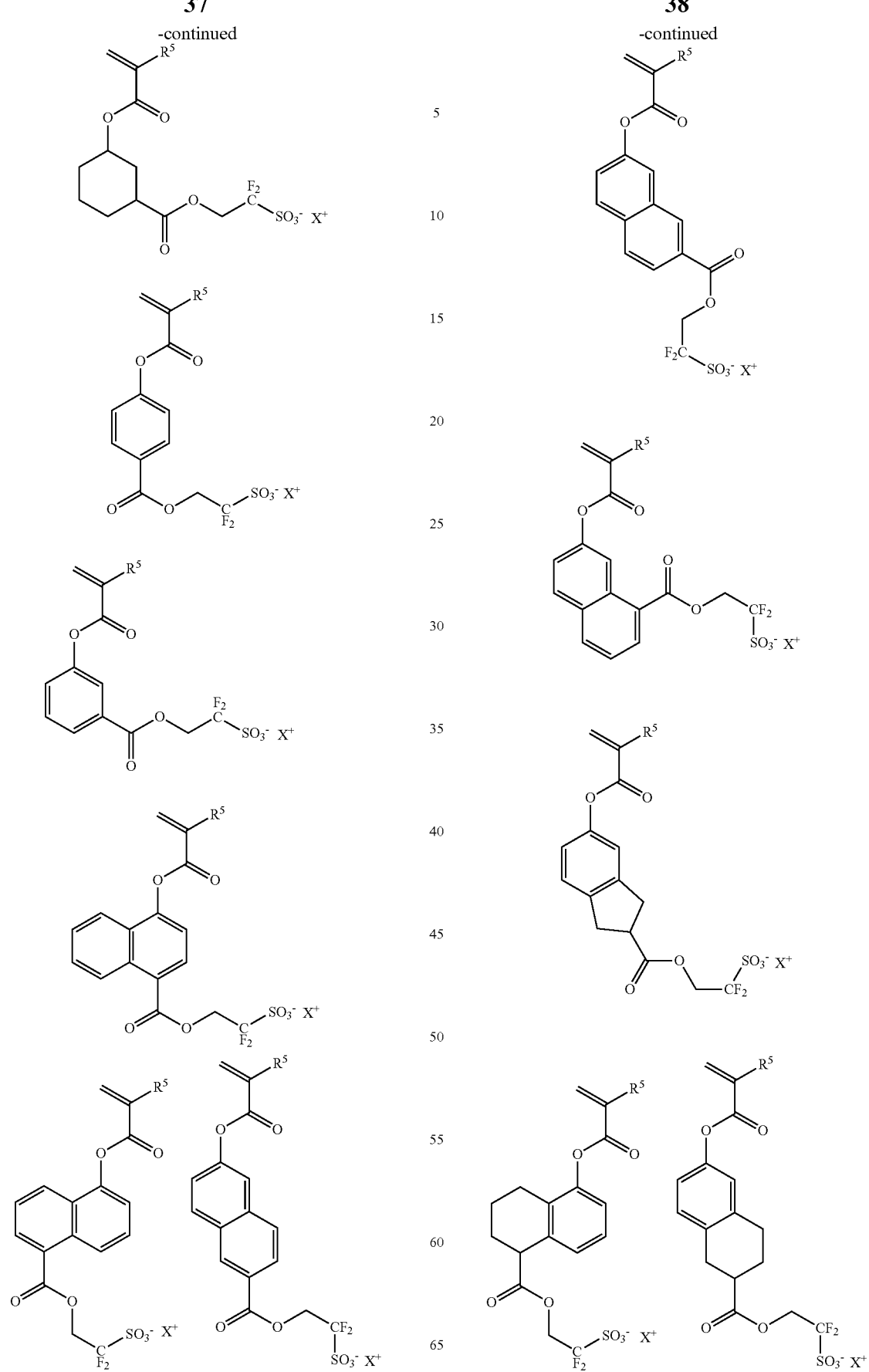

-continued

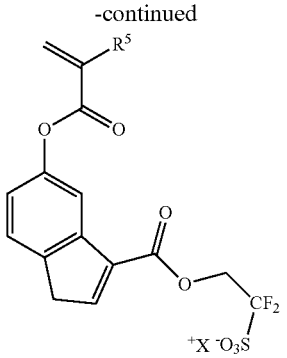
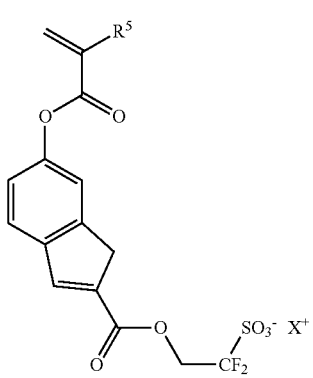
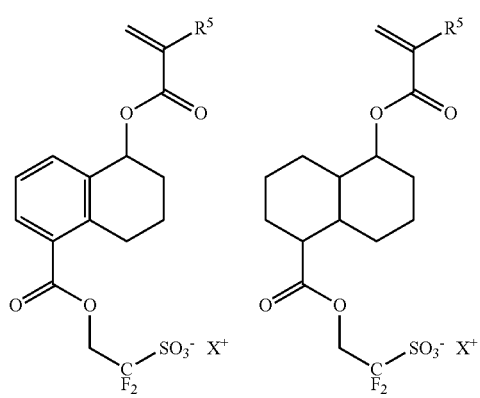
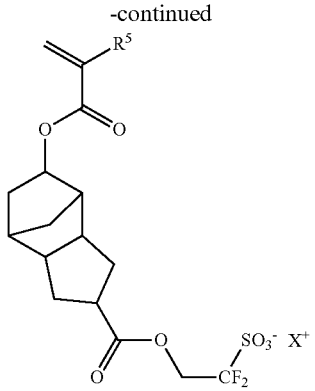
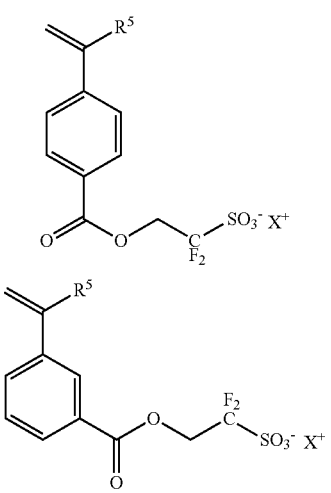
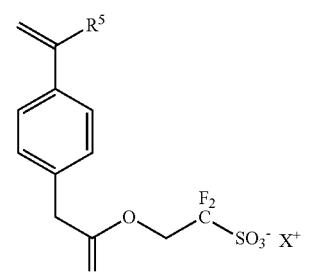
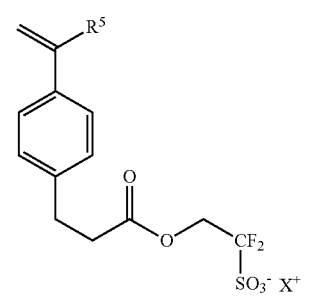

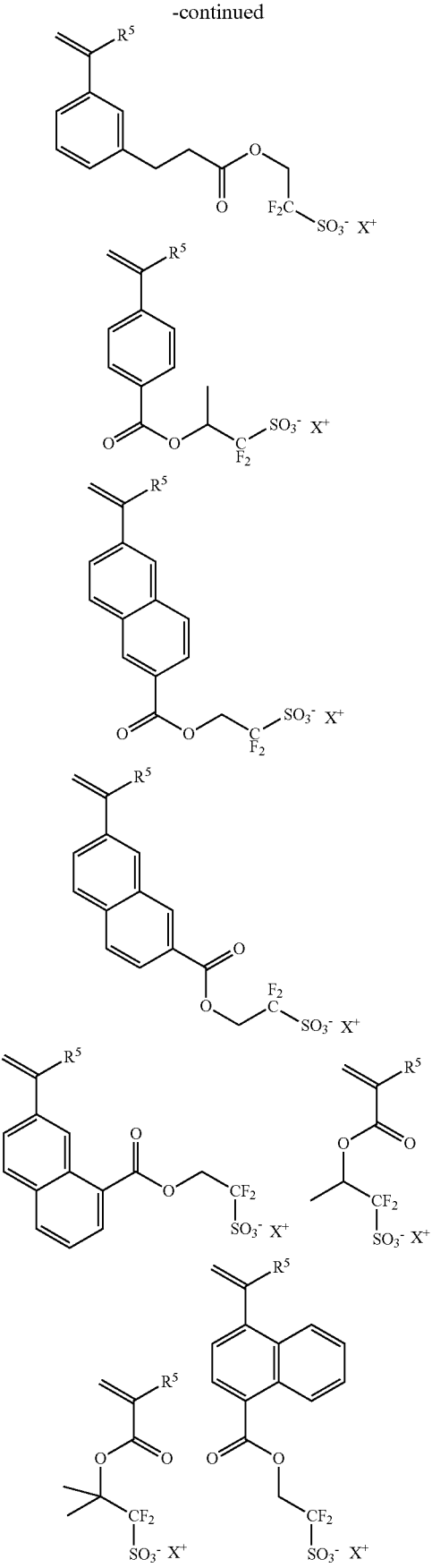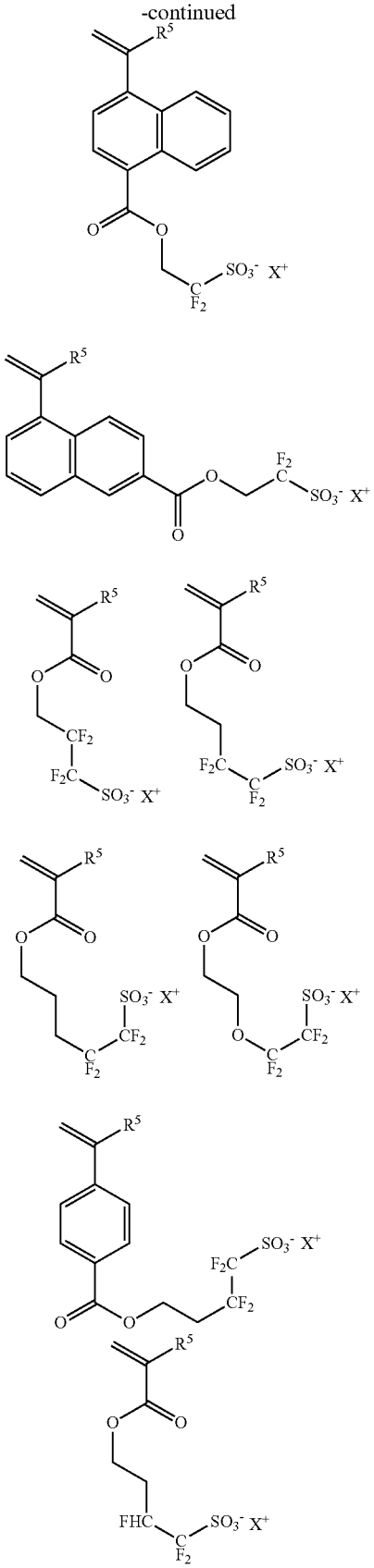
A monomer for providing the repeating unit b4' can be specifically exemplified by the following.

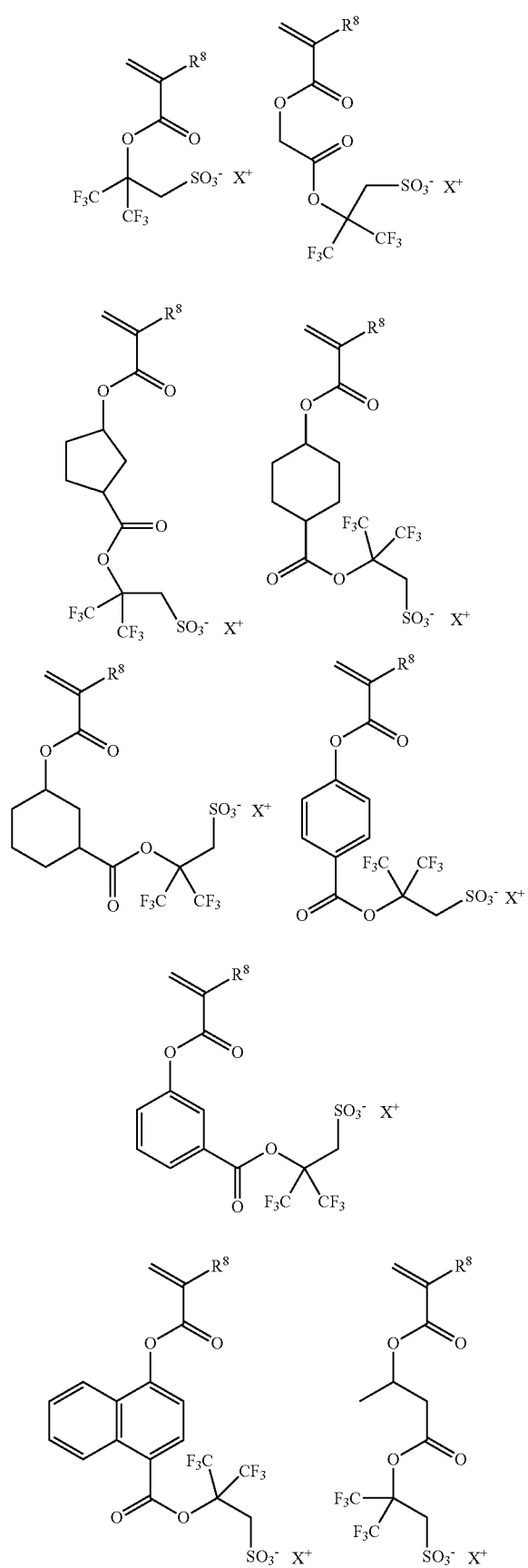
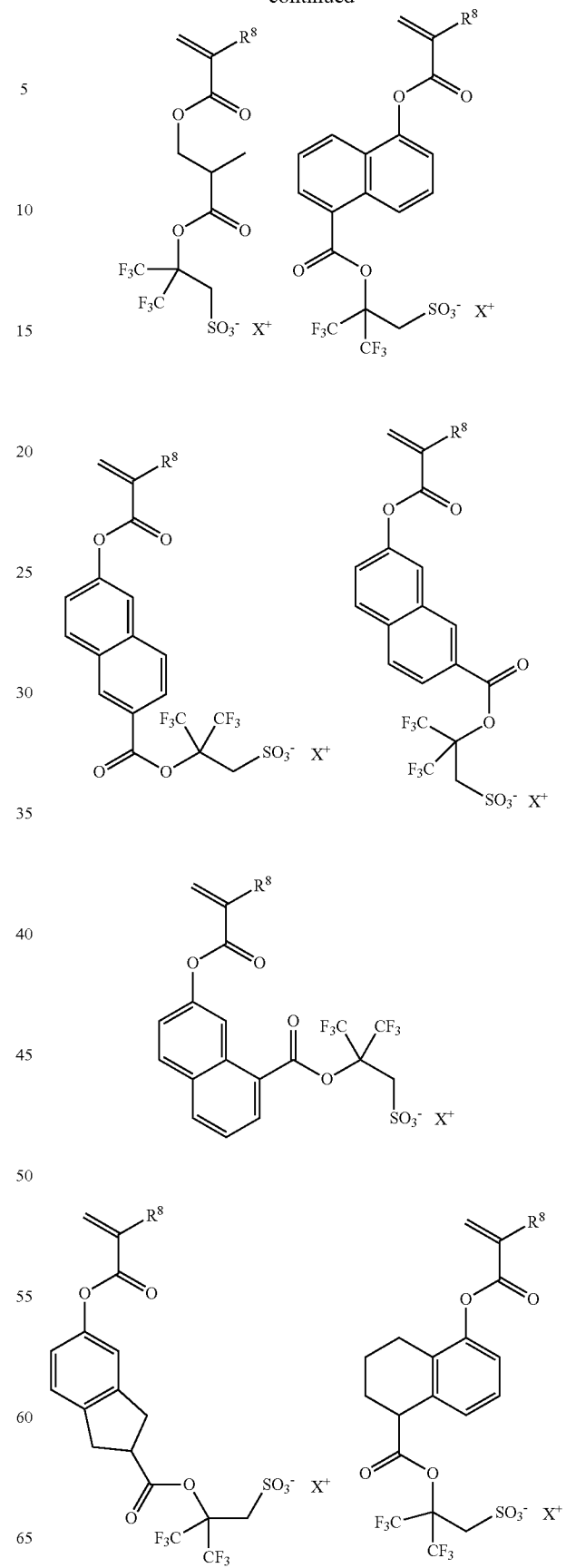

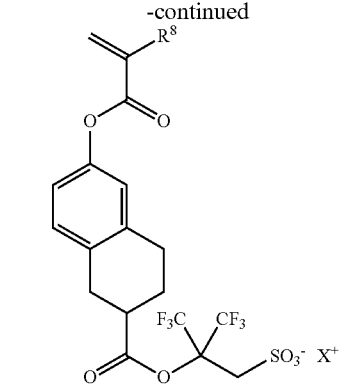
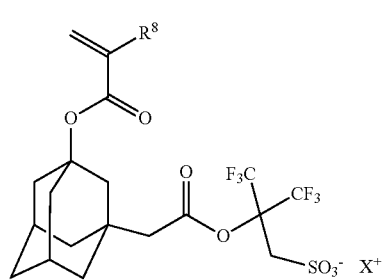
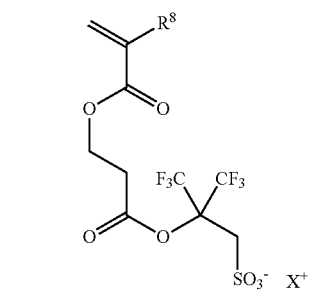
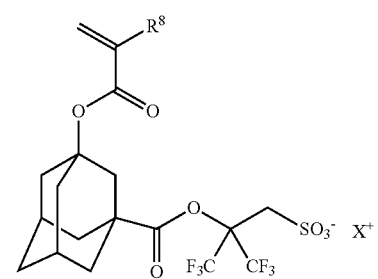
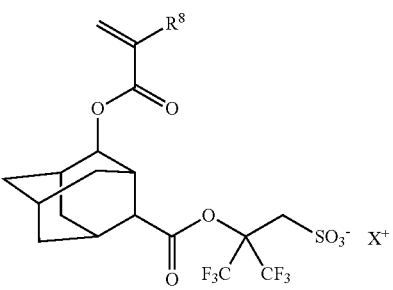
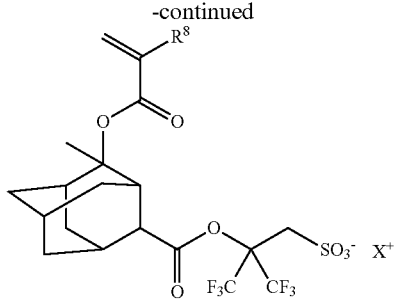
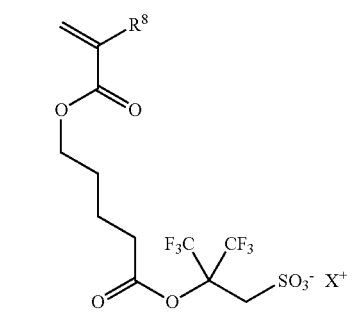
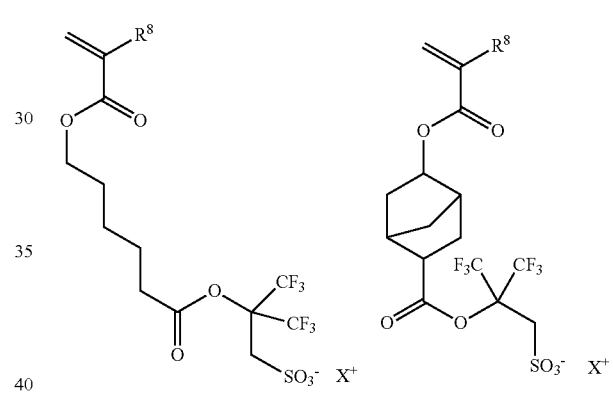
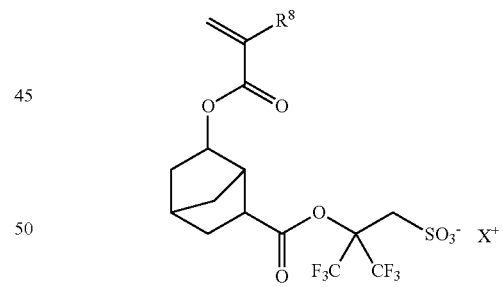
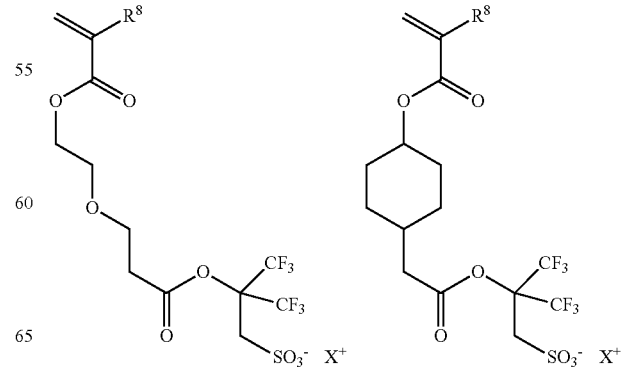

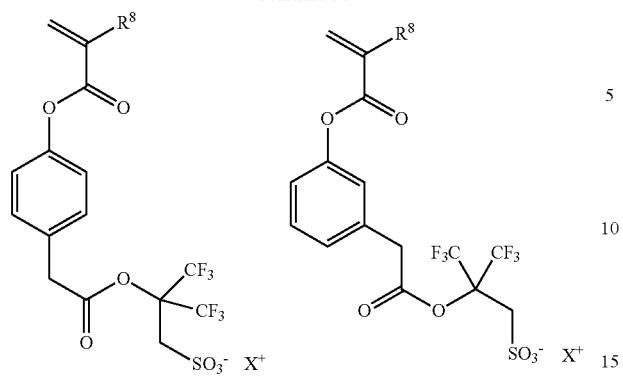
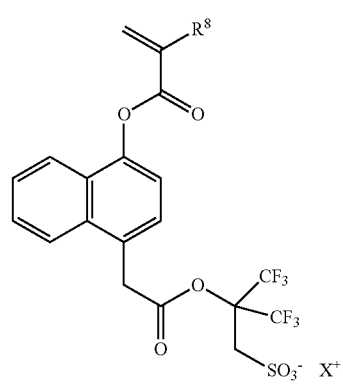
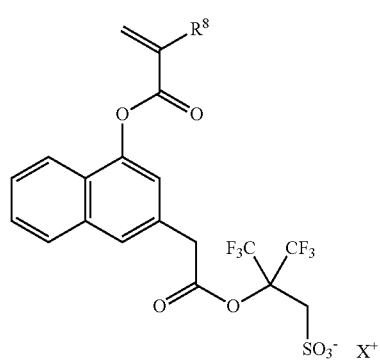
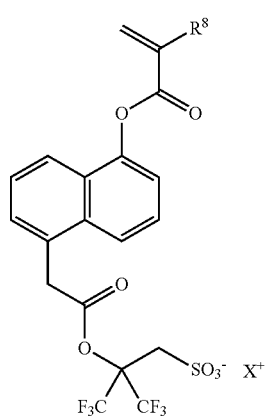
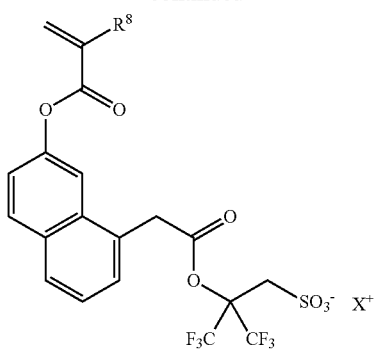
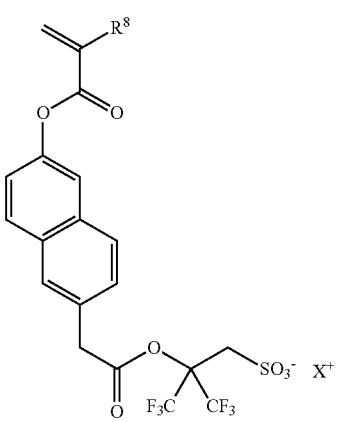
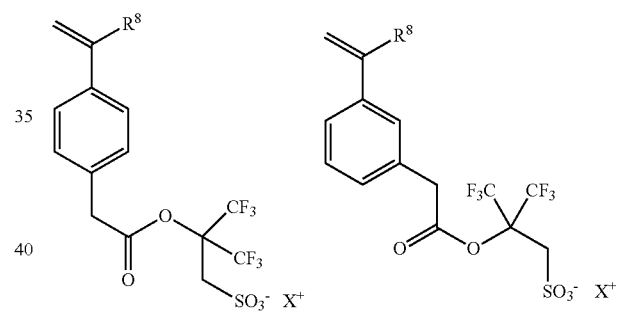
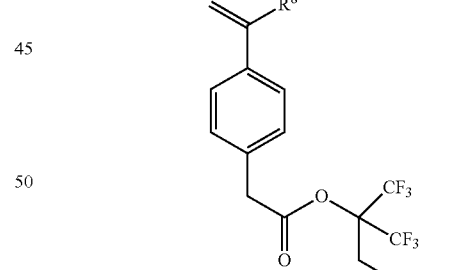
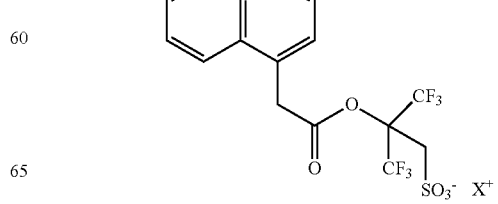

-continued
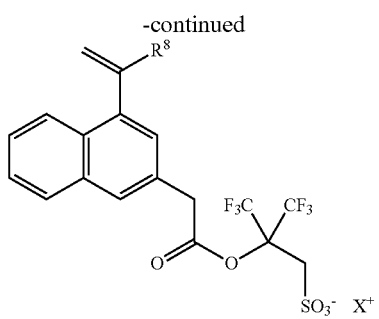
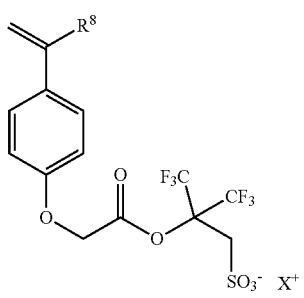
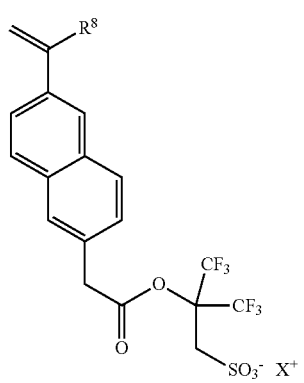
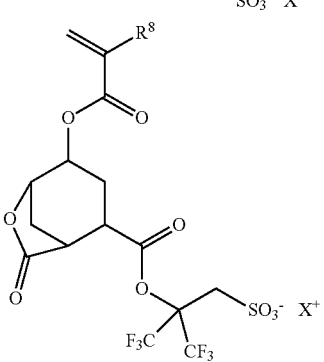
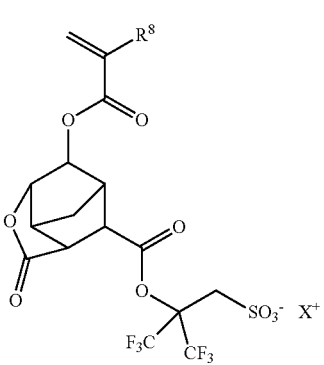
-continued
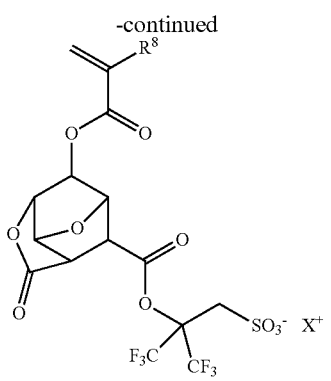
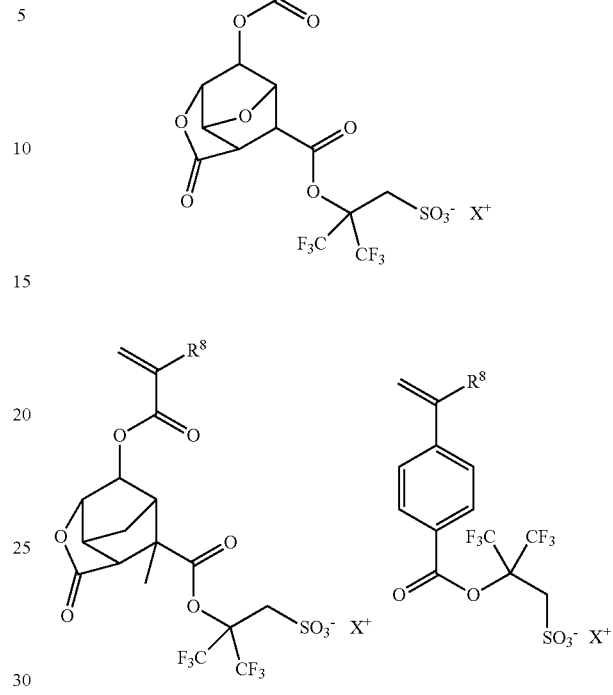
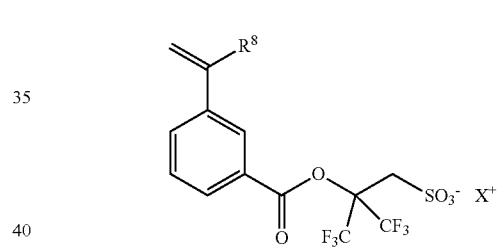
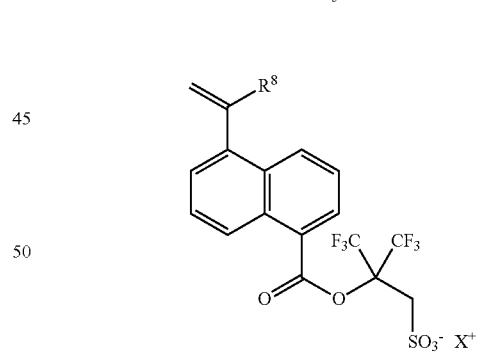
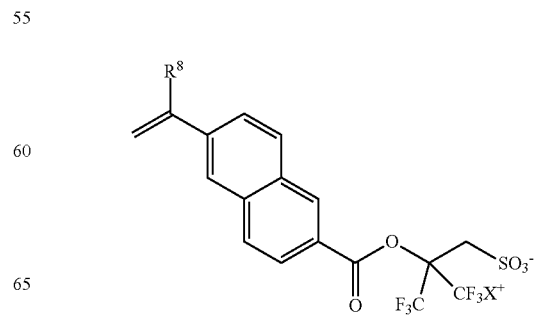

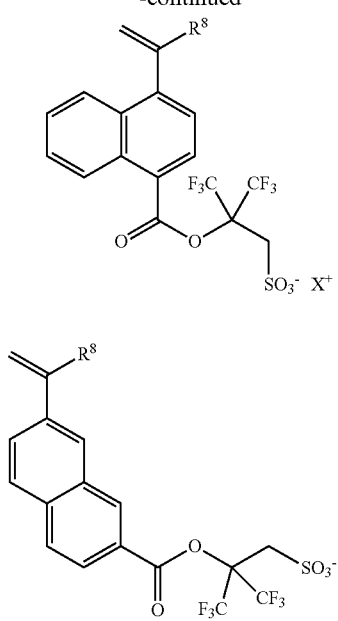
In each formula, $R^8$ is as defined above, and X represents Li, Na, K, or an amine compound.
A monomer for providing the repeating unit b5' can be specifically exemplified by the following.
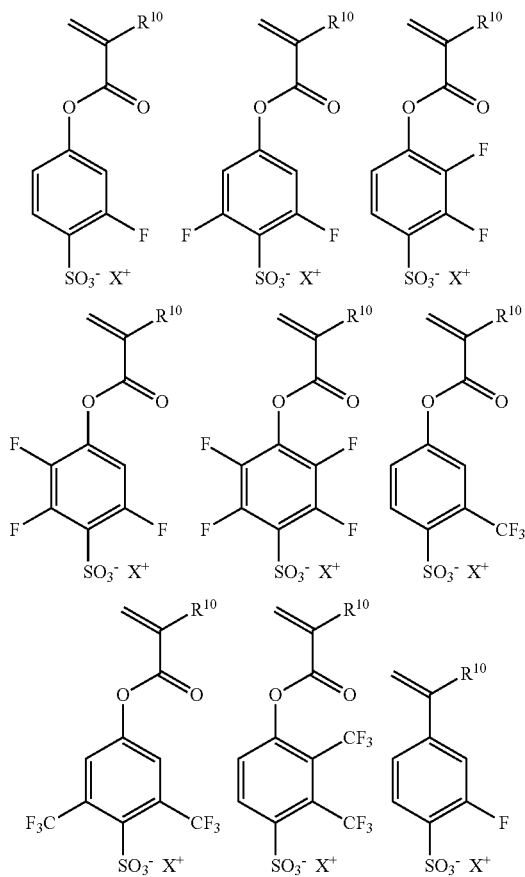
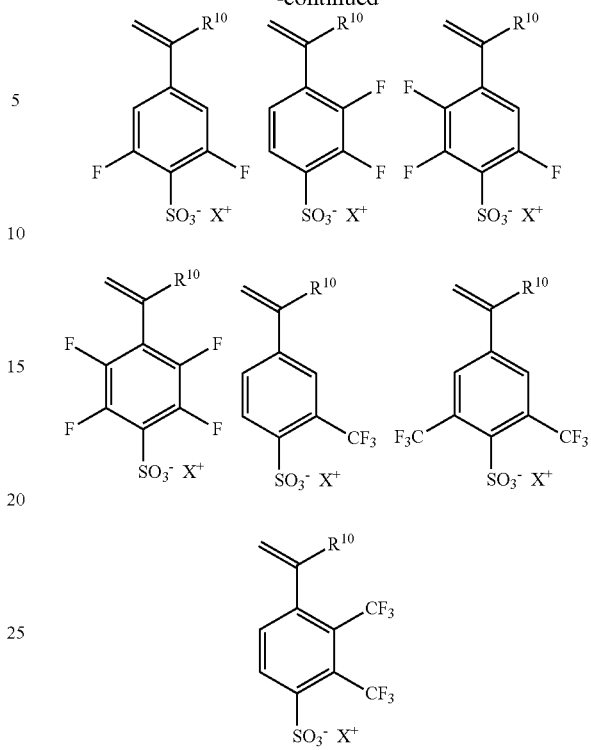
In each formula, $R^{10}$ is as defined above, and X represents Li, Na, K, or an amine compound.
A monomer for providing the repeating unit b6' can be specifically exemplified by the following.
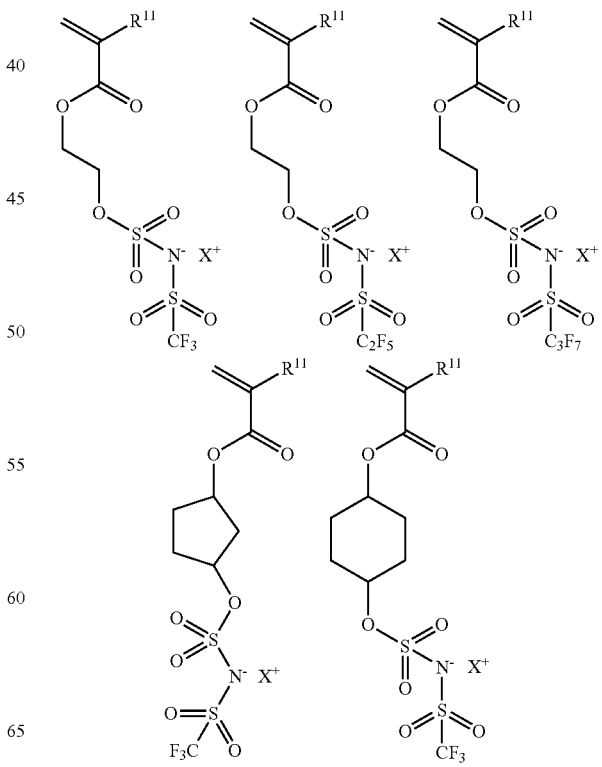

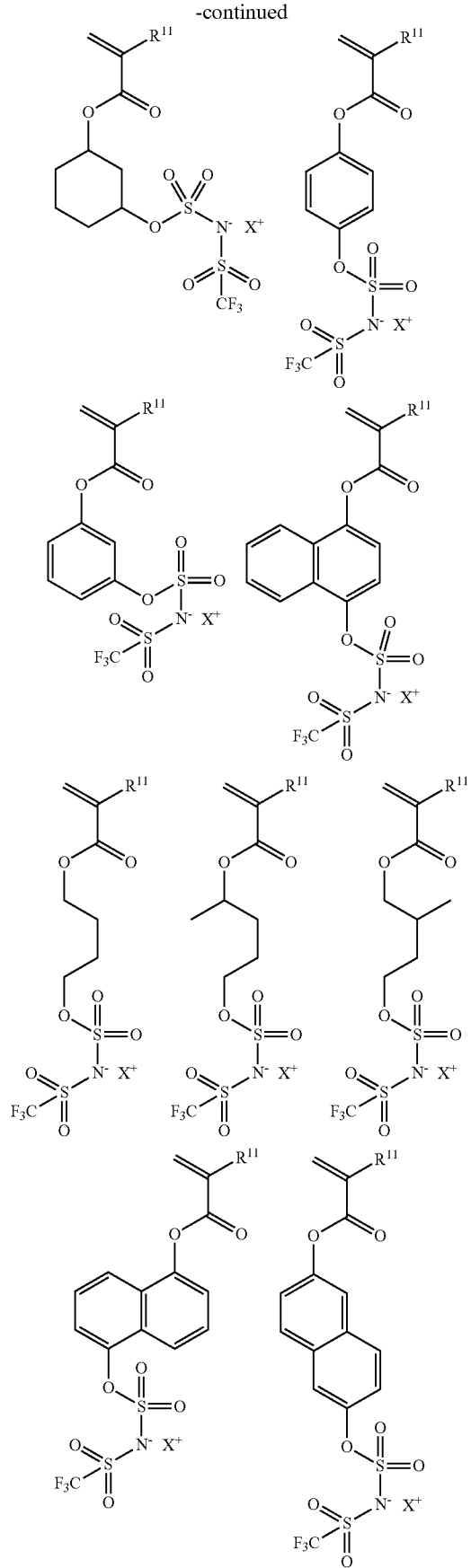
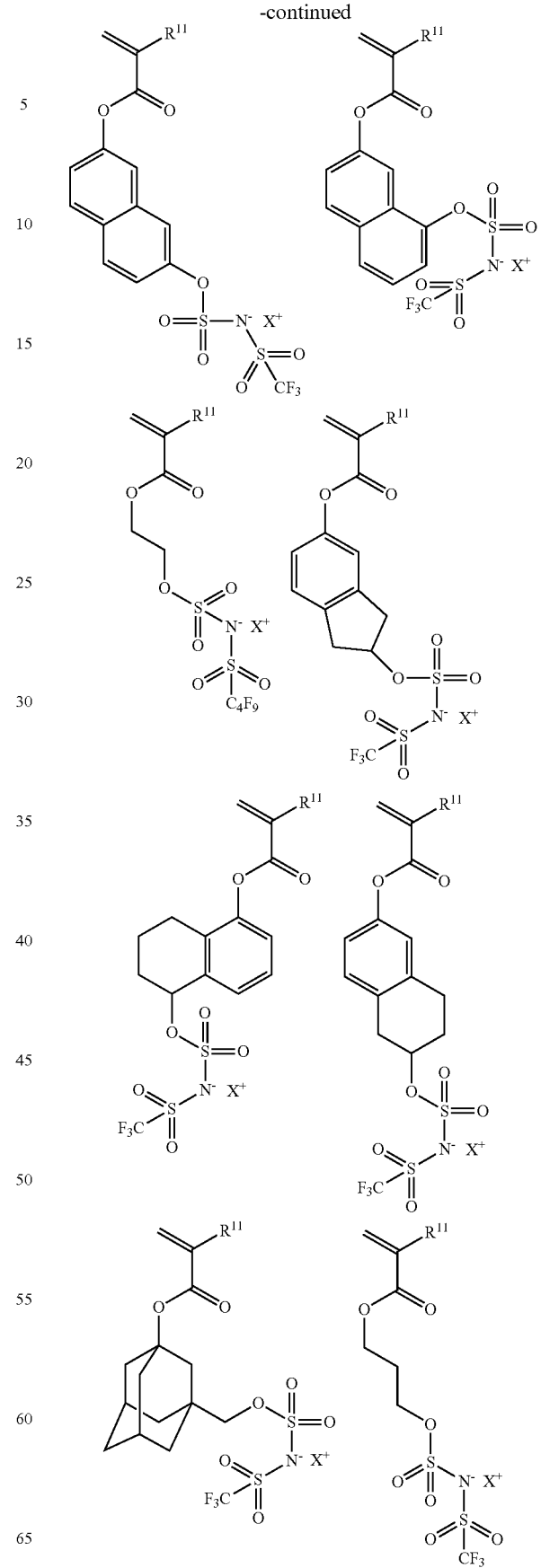

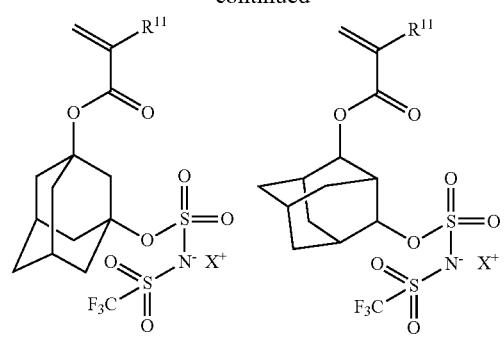
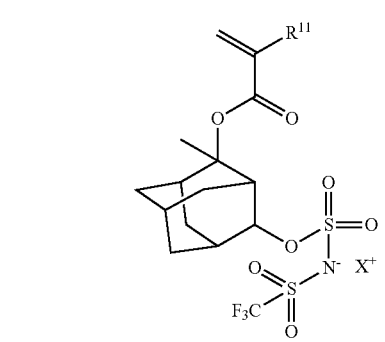
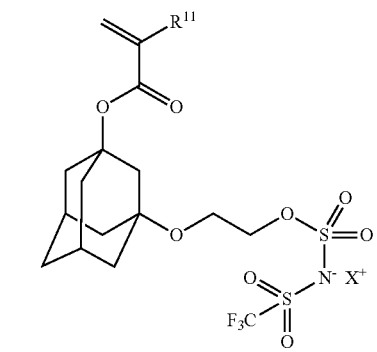
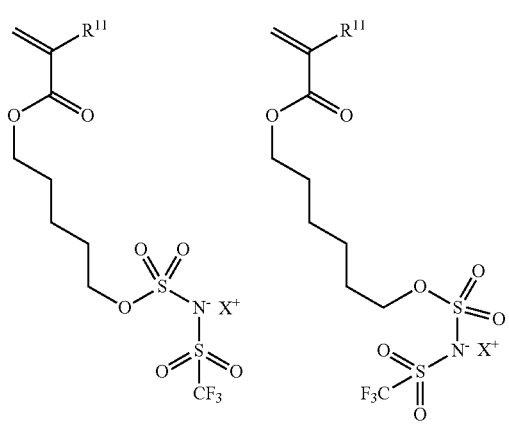
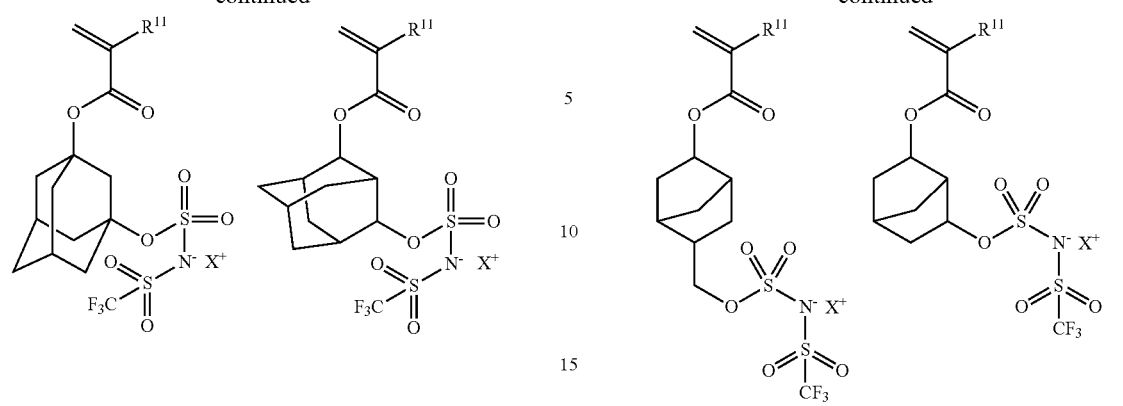
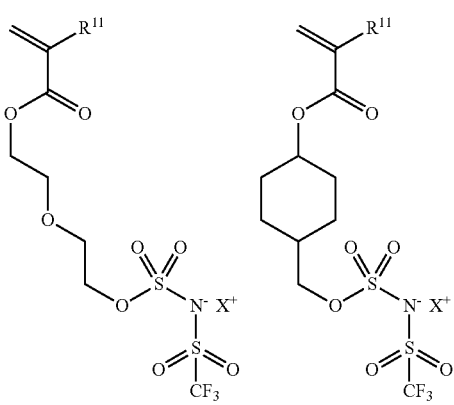
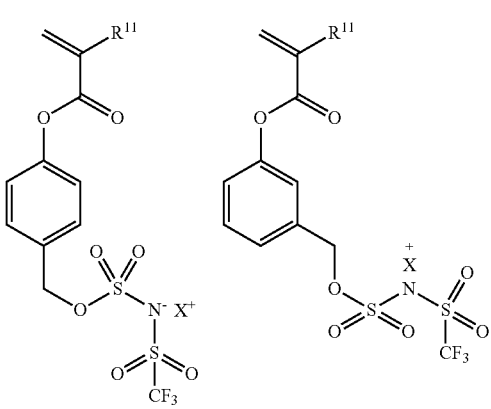
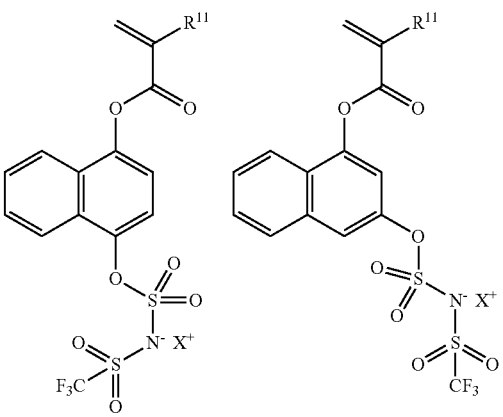

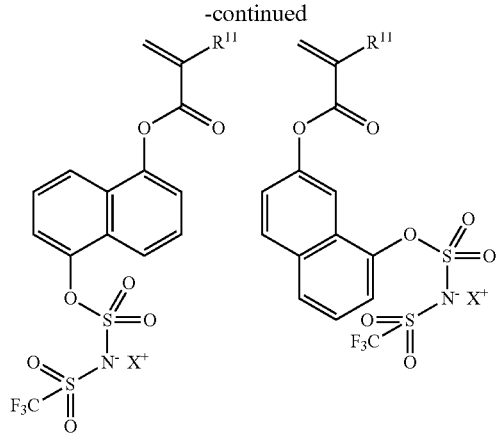
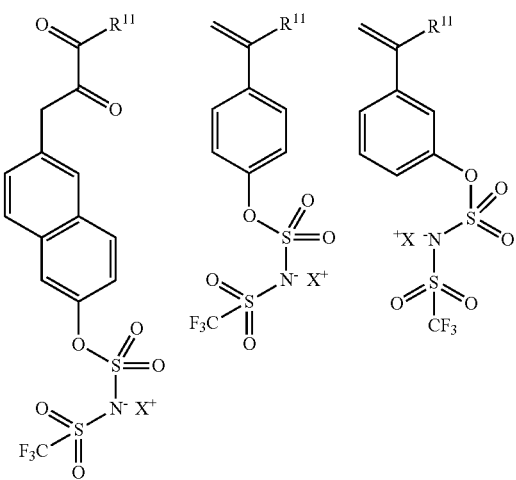
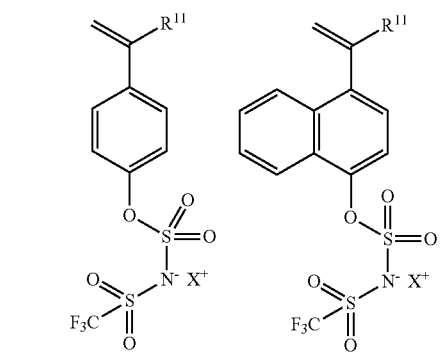
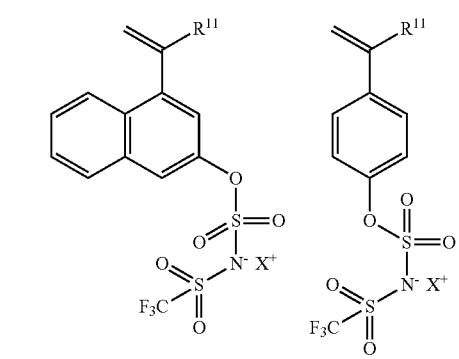
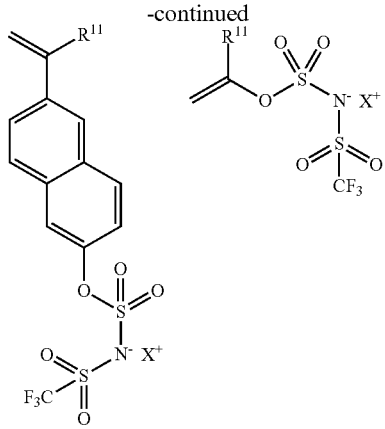
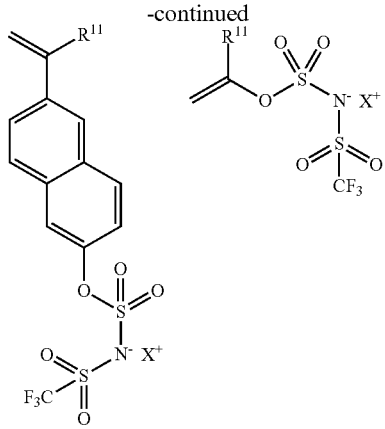
In each formula, $R^{11}$ is as defined above, and X represents Li, Na, K, or an amine compound.
A monomer for providing the repeating unit b7' can be specifically exemplified by the following.
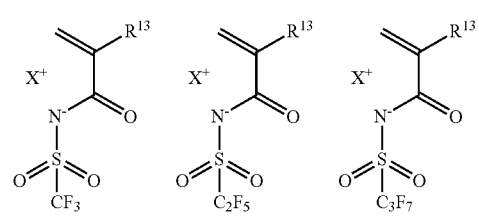
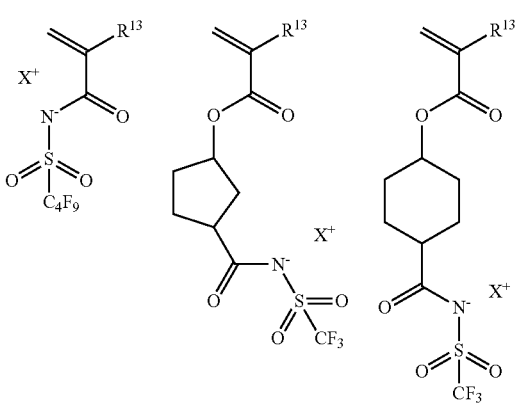
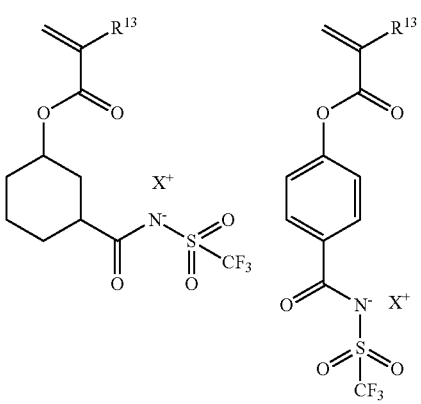

-continued
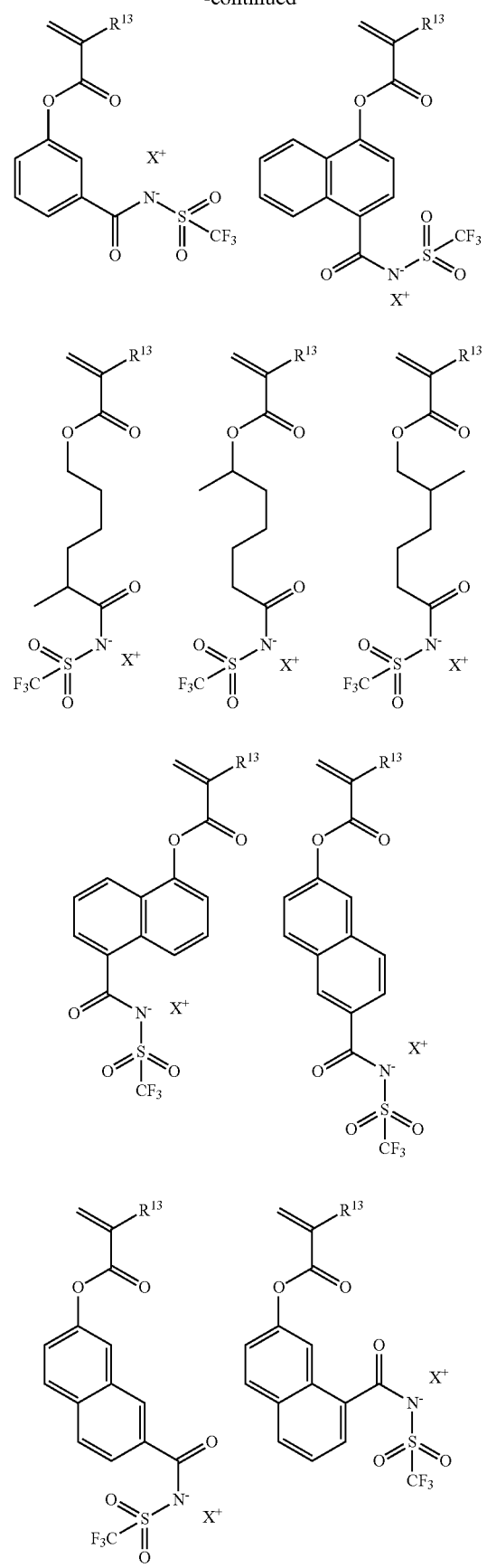
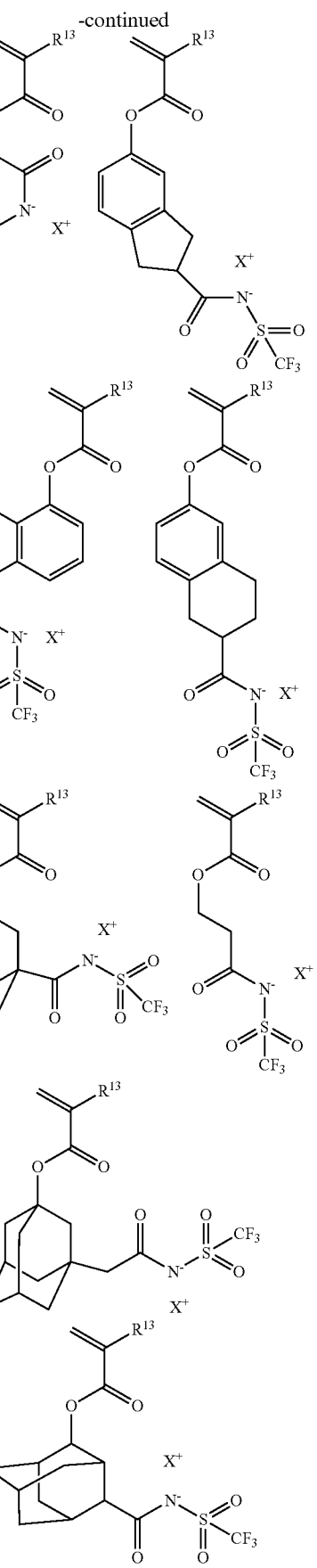

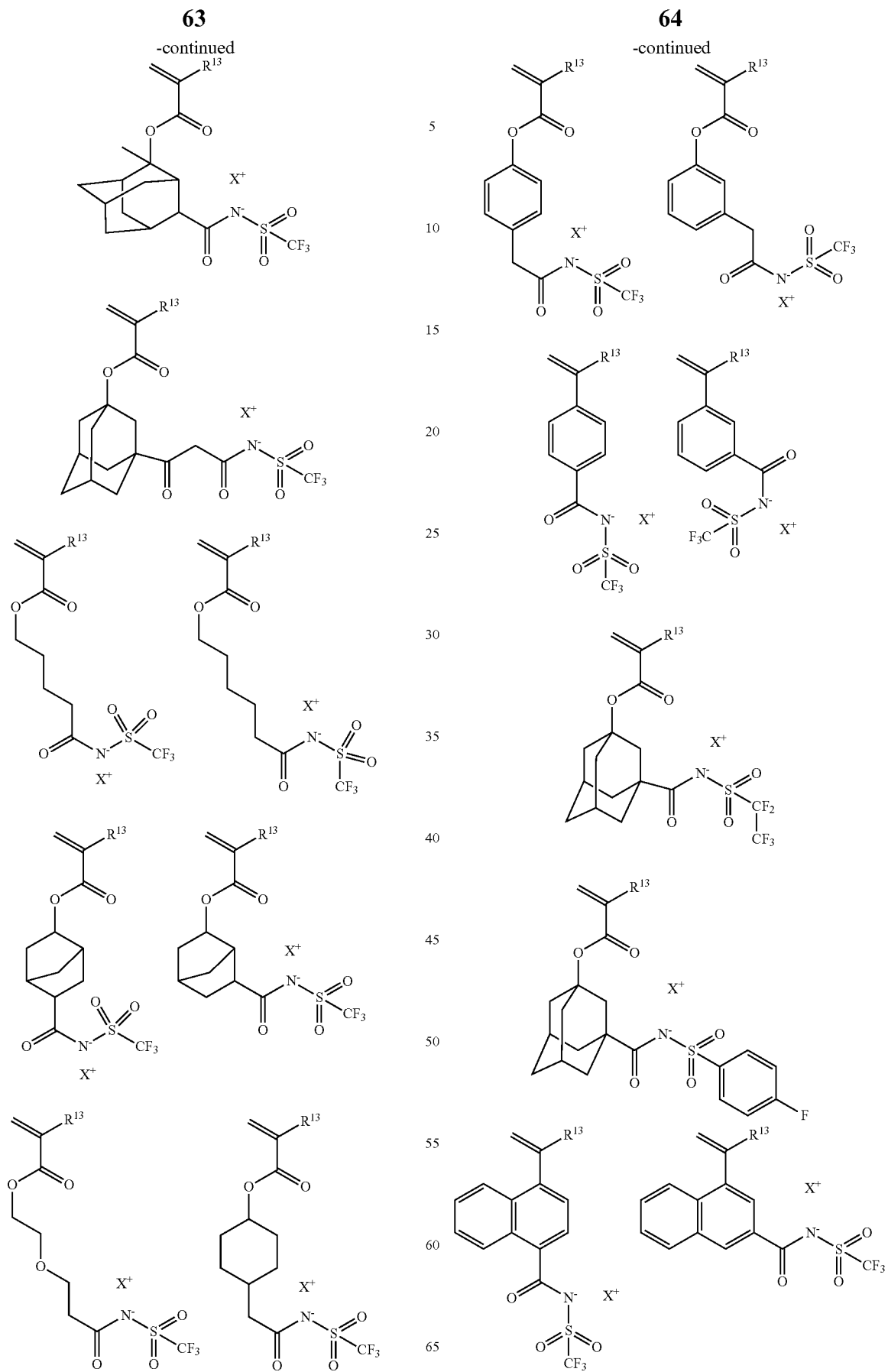

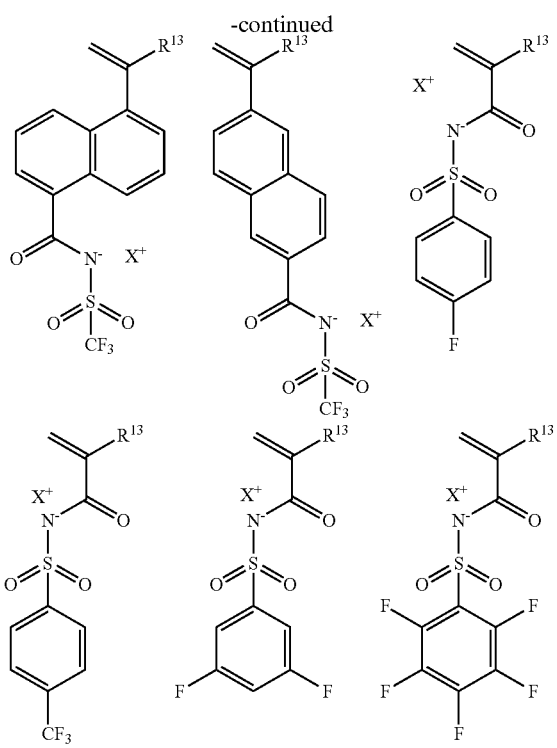

In each formula, $R^{13}$ is as defined above, and X represents Li, Na, K, or an amine compound.

Moreover, as mentioned above, the inventive polymer compound for a conductive polymer can also be copolymerized with monomers derived from styrenesulfonic acids specifically as follows:

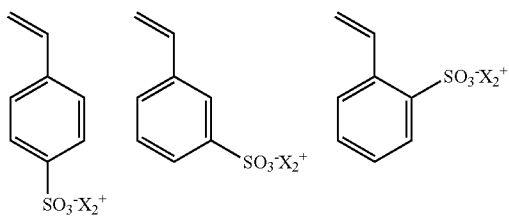

where $X_2$ represent a hydrogen atom, lithium, sodium, potassium, or an amine compound.

An example of the amine compound as $X_2$ includes a compound shown by the following general formula (5).

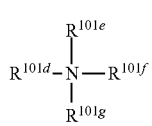

(5)

In the formula (5), $R^{101d}$, $R^{101e}$, $R^{101f}$, and $R^{101g}$ each represent a hydrogen atom, a linear, branched, or cyclic alkyl group, alkenyl group, oxoalkyl group, or oxoalkenyl group having 1 to 12 carbon atoms, an aryl group having 6 to 20 carbon atoms, or an aralkyl group or aryloxoalkyl group having 7 to 12 carbon atoms. A part or all of hydrogen atoms of these groups are optionally substituted with alkoxy groups. $R^{101d}$ and $R^{101e}$, or $R^{101d}$, $R^{101e}$, and $R^{101f}$, option- ally form a ring, and when a ring is formed, $R^{101d}$ and $R^{101e}$, or $R^{101d}$, $R^{101e}$, and $R^{101f}$ represent an alkylene group having 3 to 10 carbon atoms or a heteroaromatic ring having the nitrogen atom in the formula in the ring.

Further, the inventive polymer compound for a conductive polymer may contain a repeating unit "d" other than the repeating unit "a", the repeating units "b", and a repeating unit "c" derived from styrene sulfonic acid as described above. Examples of the repeating unit "d" include repeating units based on methacrylic, styrene, vinylnaphthalene, vinylsilane, acenaphthylene, indene, vinylcarbazole, and the like.

A monomer for obtaining the repeating unit "d" can be specifically exemplified by the following.

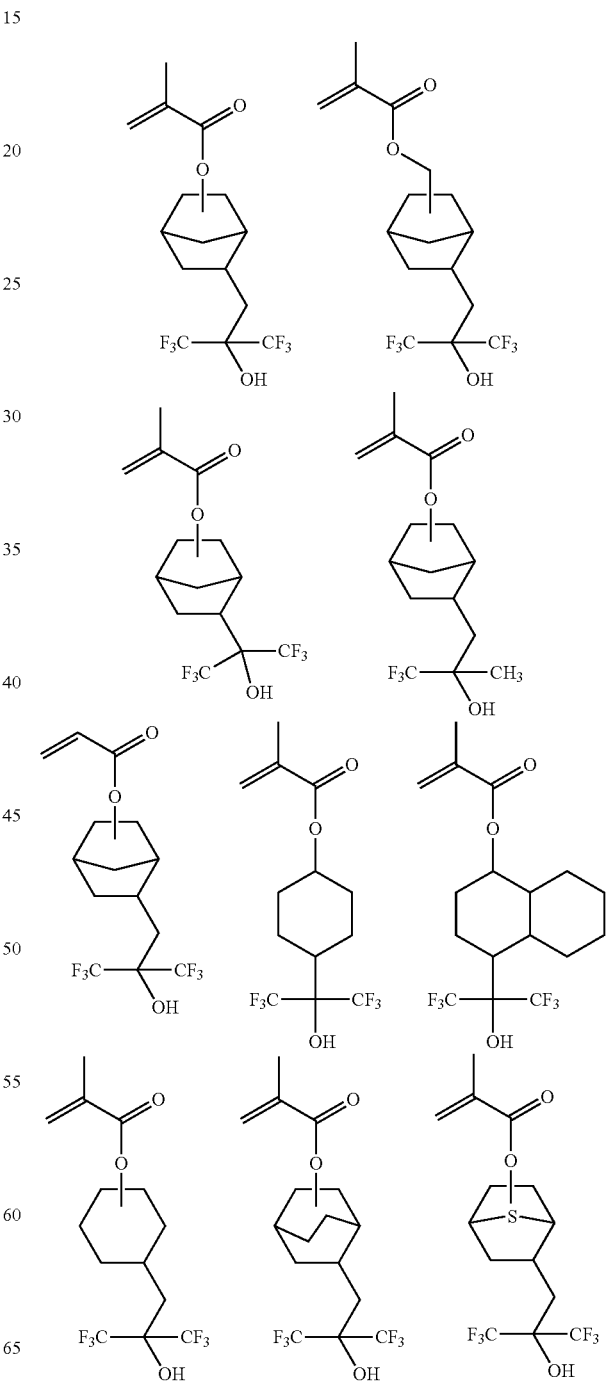

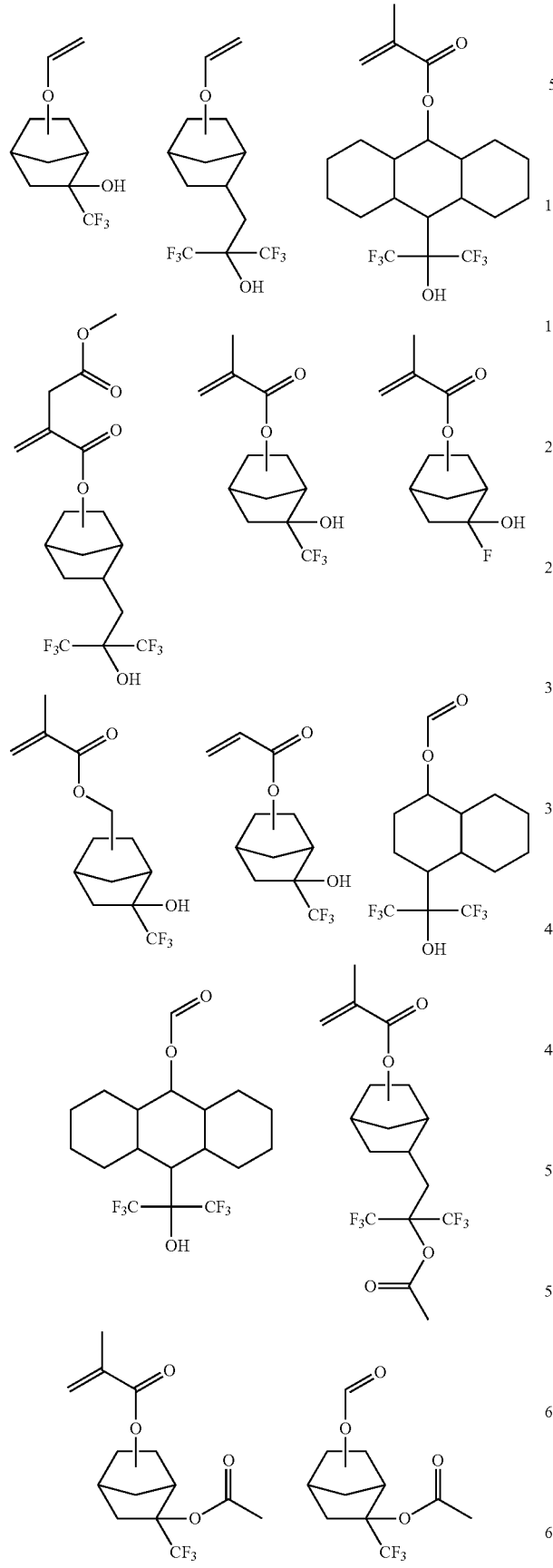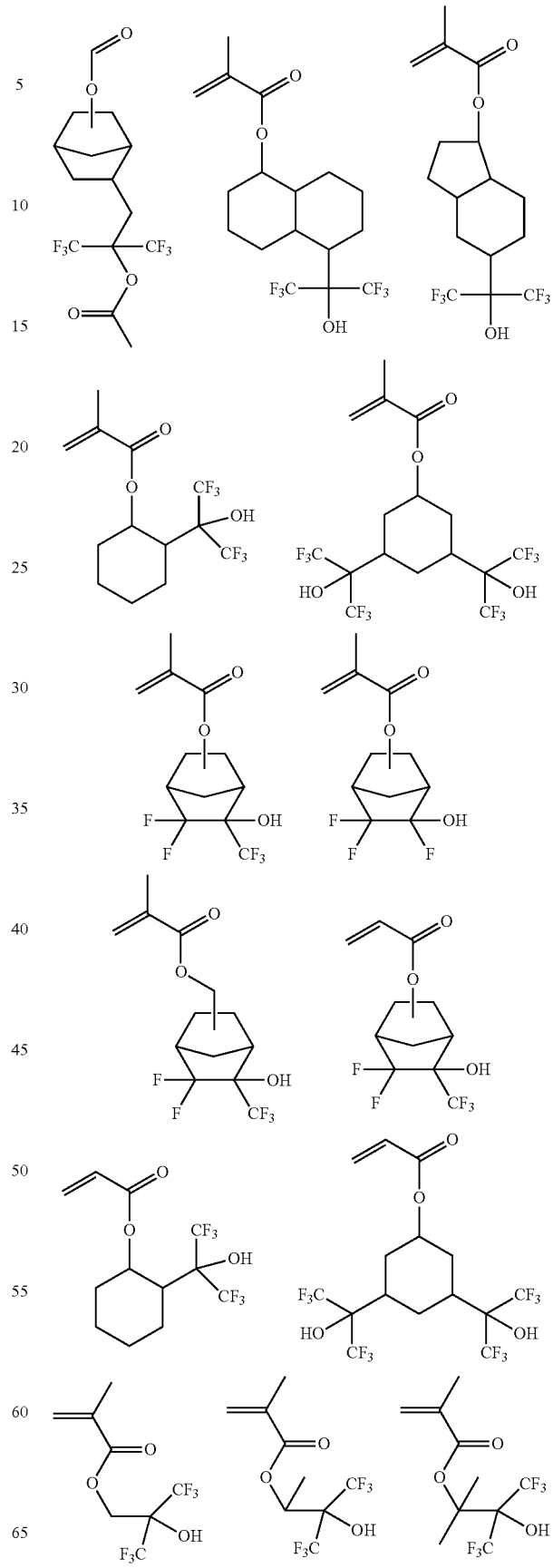

-continued
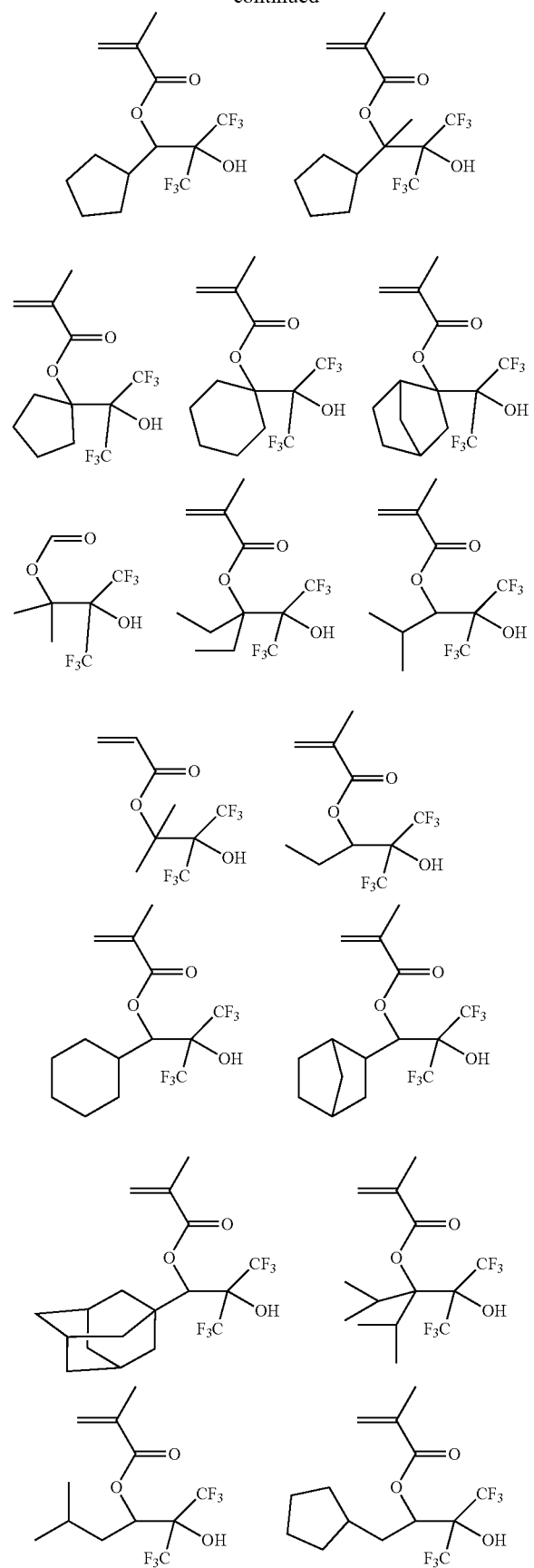
-continued
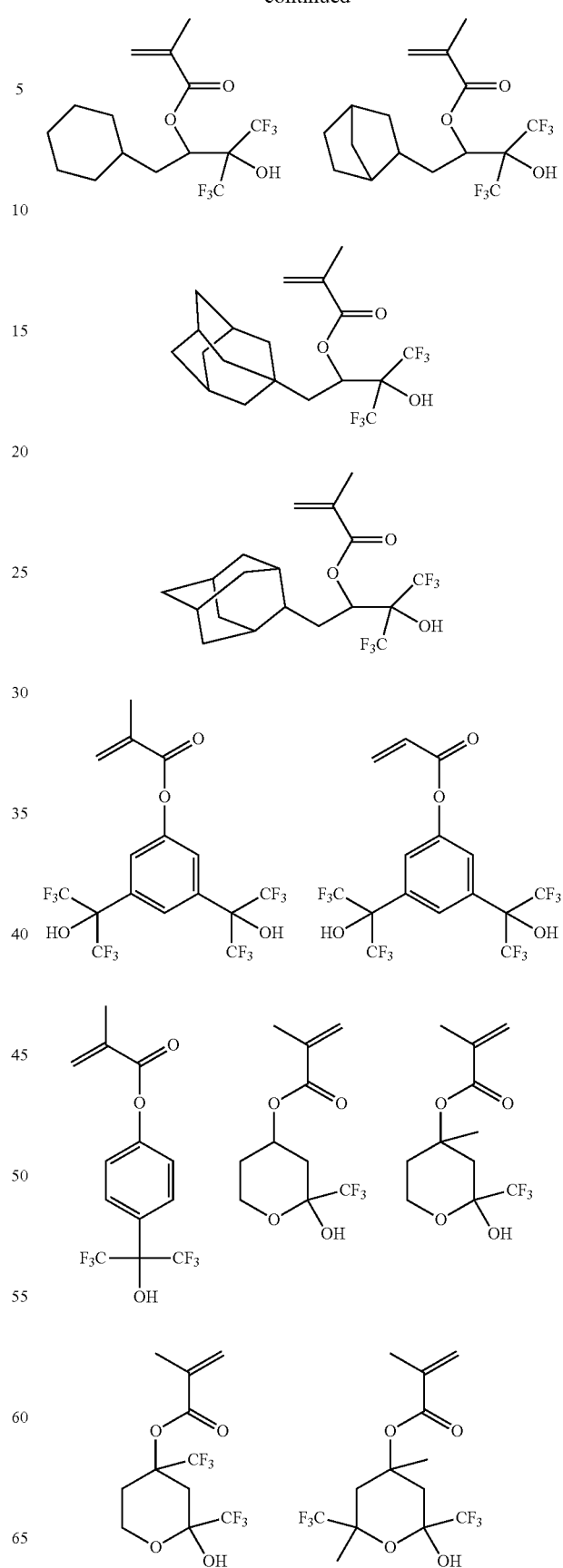

71
-continued
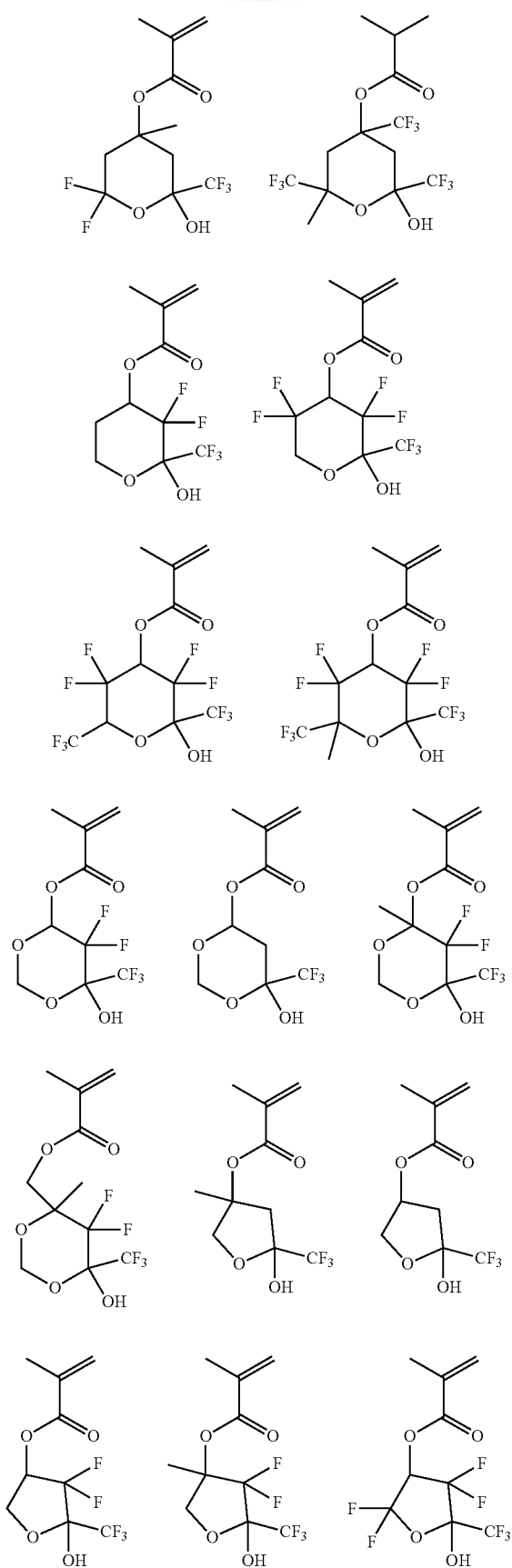
72
-continued
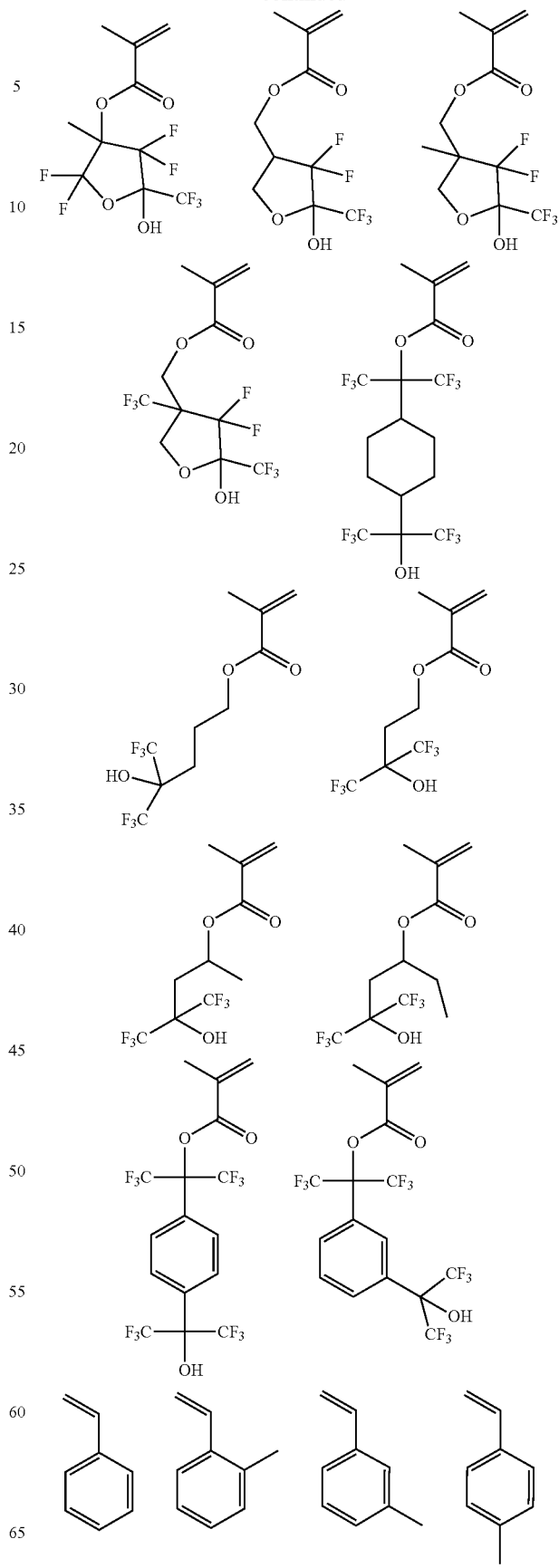

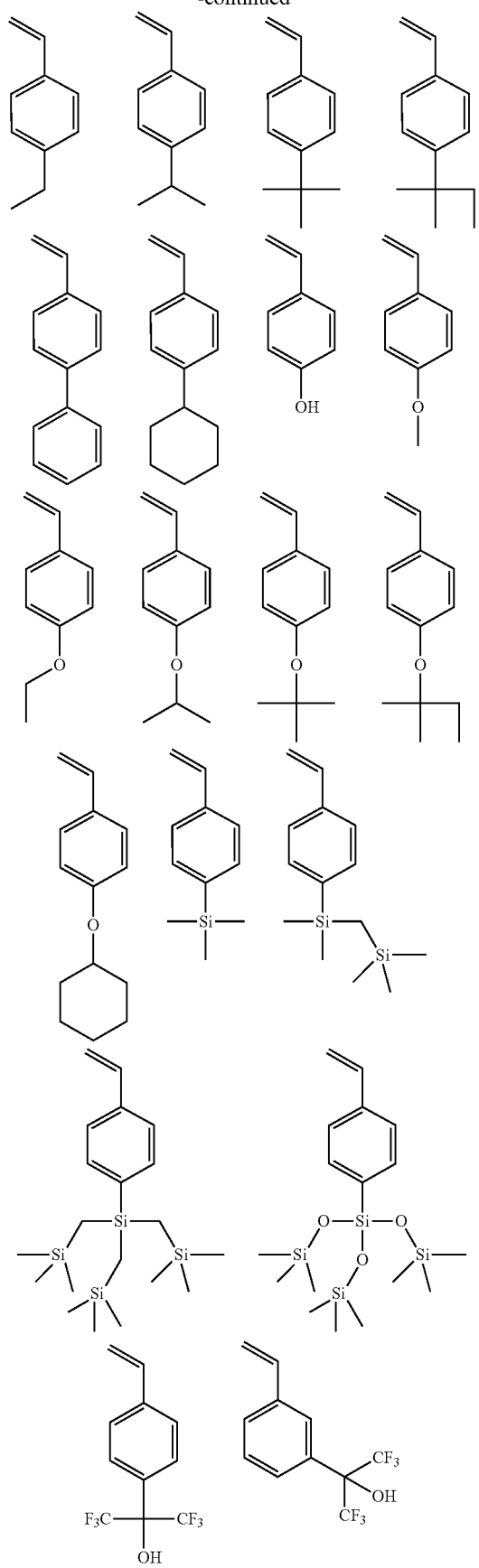
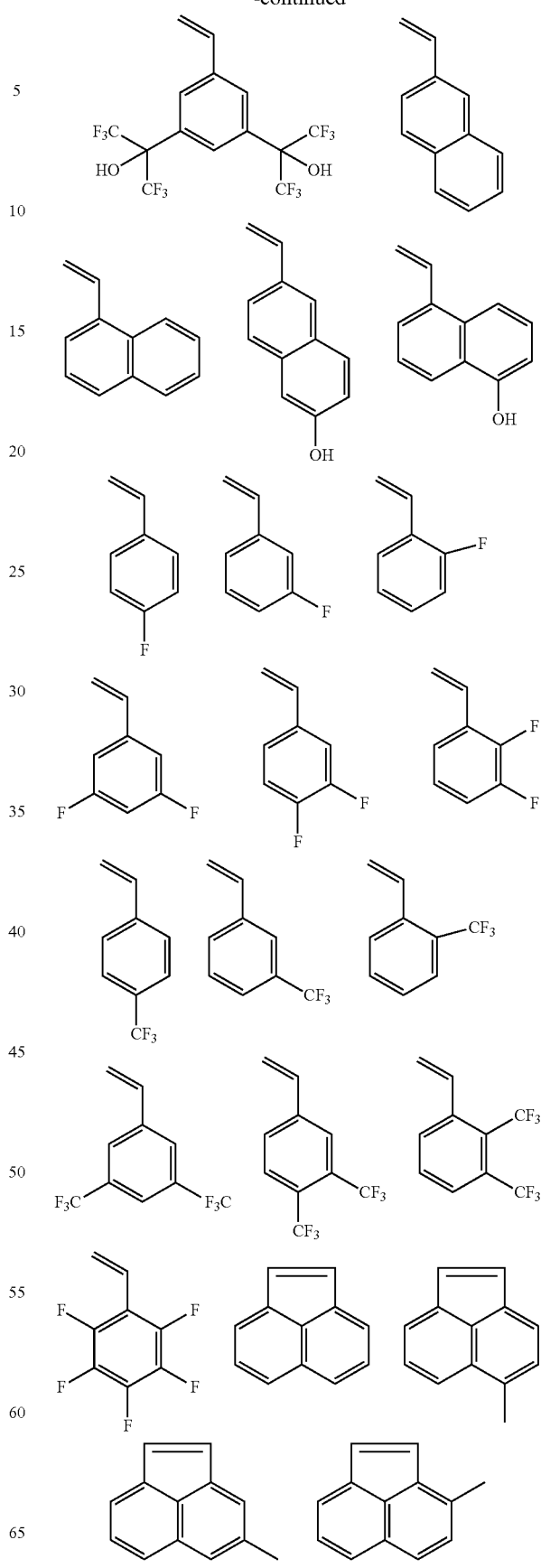

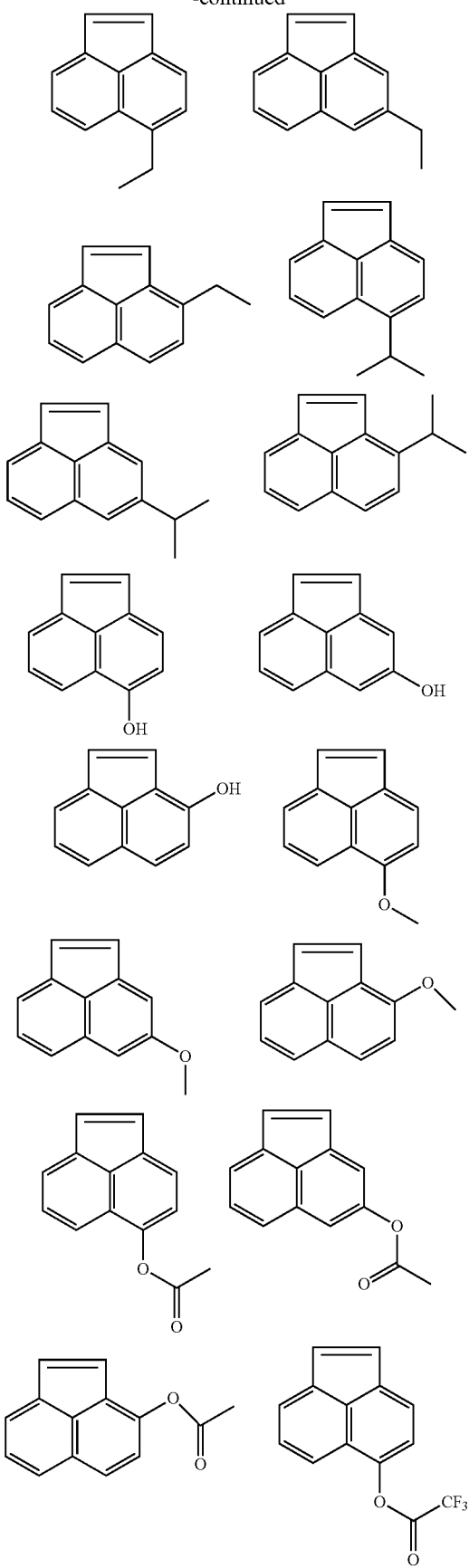
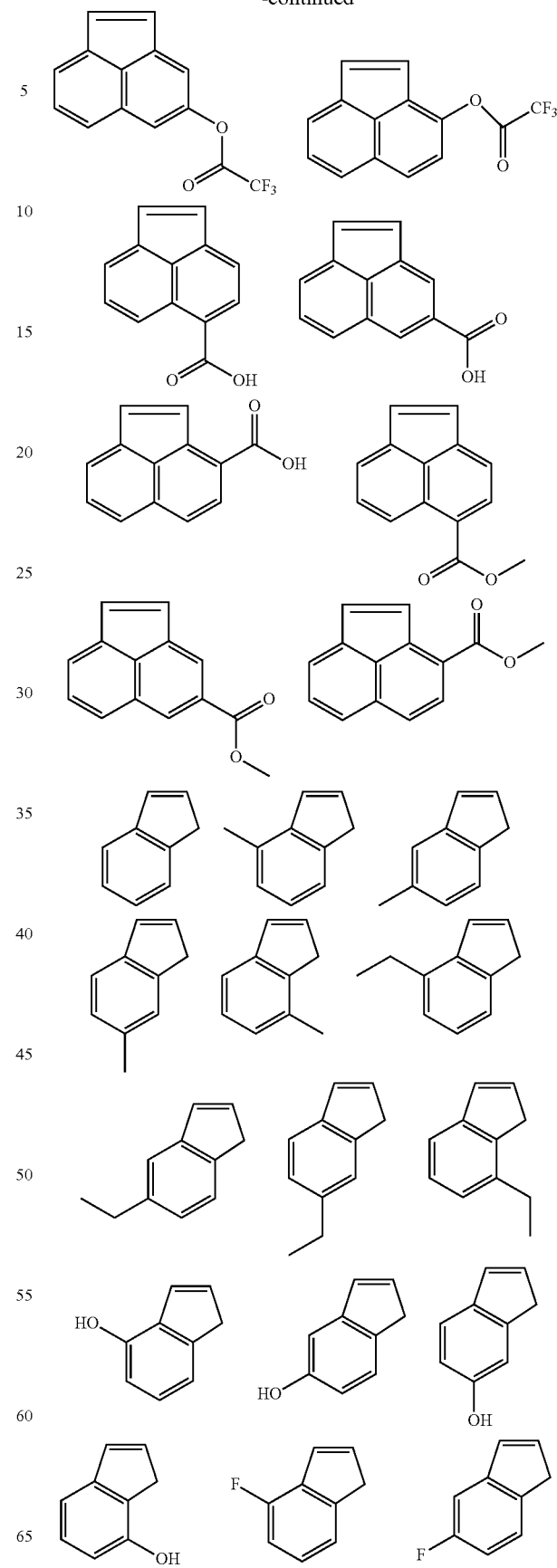

77
-continued
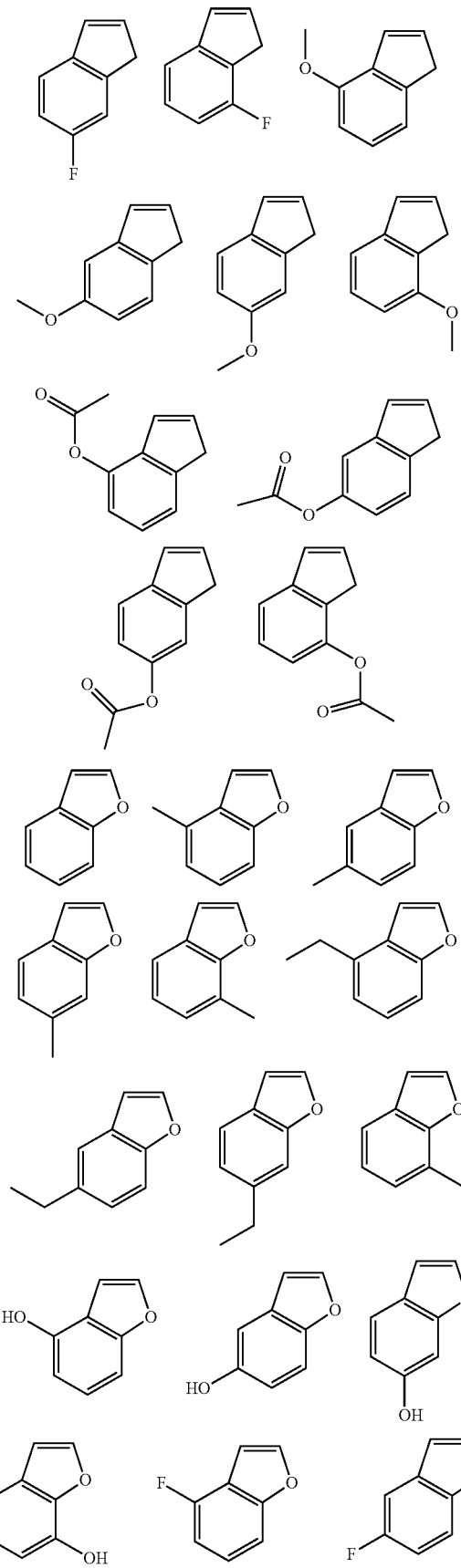
78
-continued
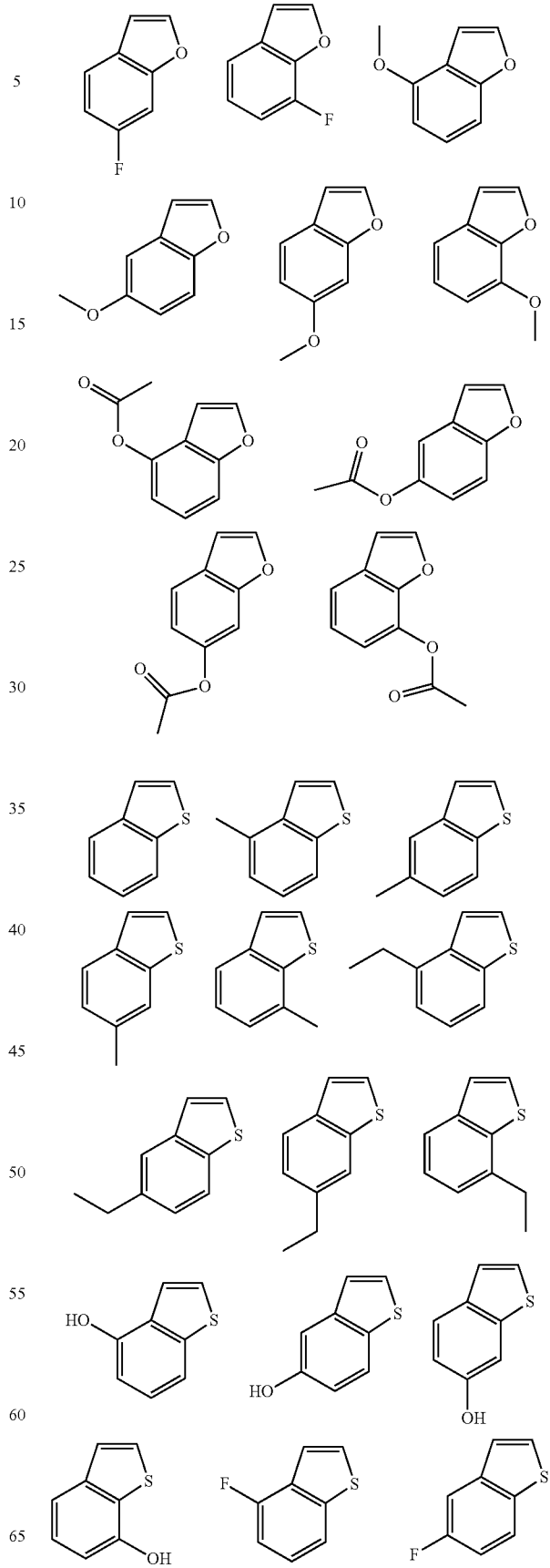

-continued

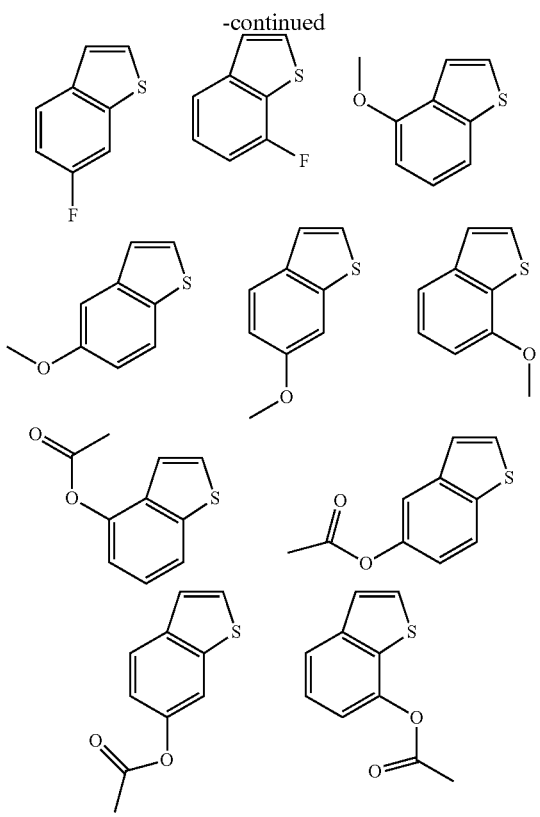

As a method of synthesizing the inventive polymer compound for a conductive polymer, the polymerizable monomer shown by the general formula (1) and at least one monomer selected from monomers each having a structure of a salt among a lithium salt, a sodium salt, a potassium salt, and a nitrogen compound salt of a fluorosulfonic acid, a fluorosulfonimide group, or a n-carbonyl-fluoro-sulfonamide group (for example, any desired monomer among the monomers for providing the repeating units b1' to b7' shown by the general formula (4)) may be subjected to polymerization under heating in a solvent by adding a radical polymerization initiator to obtain a polymer compound which is a copolymer. Then, by subjecting the obtained copolymer to ion exchange, the repeating units b1' to b7' shown by the general formula (4) can be changed to b1 to b7 shown by the general formula (3).

The solvent to be used at the time of the polymerization may be exemplified by water, methanol, ethanol, n-propanol, isopropyl alcohol, methoxyethanol, ethoxyethanol, n-butanol, ethylene glycol, propylene glycol, glycerol, diethylene glycol, dimethylsulfoamide, dimethylacetamide, acetone, dimethylsulfoxide, N-methyl-pyrrolidone, toluene, benzene, tetrahydrofuran, diethyl ether, dioxane, cyclohexane, cyclopentane, methyl ethyl ketone, γ-butyrolactone, and the like.

The radical polymerization initiator may be exemplified by di-t-butyl peroxide, dicumyl peroxide, t-butylcumyl peroxide, benzoyl peroxide, dilauryl peroxide, cumene hydroperoxide, t-butyl hydroperoxide, t-butyl peroxyisobutyrate, potassium persulfate, ammonium persulfate, aqueous hydrogen peroxide, 2,2'-azobisisobutyronitrile (AIBN), 2,2'-azobis(2,4-dimethylvaleronitrile), dimethyl 2,2-azobis(2-methylpropionate), lauroyl peroxide, 2,2'-azobis(2-amidinopropane) dihydrochloride, an alkali metal salt or an ammonium salt of 4,4'-azobis(4-cyanovaleric acid), or the like.

The reaction temperature is preferably 50 to 80° C., and the reaction time is preferably 2 to 100 hours, more preferably 5 to 20 hours.

In the inventive polymer compound for a conductive polymer, each of the monomers providing the repeating unit "a" shown by the general formula (2) and the repeating unit "b" including the repeating units b1 to b7 shown by the general formula (3) may be either one kind or in combination of two or more kinds.

Also, one kind or two or more kinds of the monomers for forming the repeating unit "a" and the repeating unit "b" including the repeating units b1 to b7 may be randomly copolymerized, or may be copolymerized in block. When the block copolymerized polymer (block copolymer) is made into a conductive film, the repeating unit portions of two or more kinds of the repeating unit "a" aggregate to form a sea-island structure, whereby a merit of improving electric conductivity can be expected.

In addition, the monomers for obtaining the repeating units "a", "b" including b1 to b7, "c", and "d" may be randomly copolymerized, or may be copolymerized in block.

When the random copolymerization is carried out by the radical polymerization, it is a general method that monomers to be copolymerized and a radical polymerization initiator are mixed and polymerized under heating. Polymerization is started in the presence of a first monomer and a radical polymerization initiator, and a second monomer is added later. Thereby, one side of the polymer molecule has a structure in which the first monomer is polymerized, and the other side has a structure in which the second monomer is polymerized. In this case, however, the repeating units of the first and second monomers are mixedly present in the intermediate portion, and the form is different from that of the block copolymer. For forming the block copolymer by the radical polymerization, living radical polymerization is preferably used.

In the living radical polymerization method called as the RAFT polymerization (Reversible Addition Fragmentation chain Transfer polymerization), the radical at the end of the polymer is always living, so that polymerization is started with the first monomer, and at the stage when it is consumed, by adding the second monomer, it is possible to form a block copolymer by the first and second repeating units. Further, when polymerization is started with the first monomer, and at the stage when it is consumed, the second monomer is added, and then, a third monomer is added, then, a tri-block copolymer can be formed.

When the RAFT polymerization is carried out, there is a characteristic that a narrow dispersion polymer in which a molecular weight distribution (dispersity) is narrow is formed. In particular, when the RAFT polymerization is carried out by adding the monomers at a time, a polymer having a narrower molecular weight distribution can be formed.

The inventive polymer compound for a conductive polymer preferably has a molecular weight distribution (Mw/Mn) of preferably 1.0 to 2.0, particularly preferably a narrow dispersion of 1.0 to 1.5. With a narrow dispersion, it is possible to prevent non-uniform electric conductivity of the conductive polymer synthesized by using the polymer compound.

For carrying out the RAFT polymerization, a chain transfer agent is necessary. Specific examples thereof include 2-cyano-2-propylbenzothioate, 4-cyano-4-phenylcarbonothioylthiopentanoic acid, 2-cyano-2-propyl dodecyl trithiocarbonate, 4-cyano-4-[(dodecylsulfanylthiocarbonyl)sulfanyl]

pentanoic acid, 2-(dodecylthiocarbonothioylthio)-2-methylpropanoic acid, cyanomethyl dodecyl thiocarbonate, cyanomethyl methyl(phenyl)carbamothioate, bis(thiobenzoyl)disulfide, and bis(dodecylsulfanylthiocarbonyl)disulfide. Among these, 2-cyano-2-propylbenzothioate is particularly preferable.

Here, a ratio of the repeating units "a", b1 to b7, "c", and "d" may be 0<a<1.0, 0≤b1<1.0, 0≤b2<1.0, 0≤b3<1.0, 0≤b4<1.0, 0≤b5<1.0, 0≤b6<1.0, 0≤b7<1.0, 0<b1+b2+b3+b4+b5+b6+b7<1.0, 0≤c<1.0, and 0≤d<1.0; preferably 0.15≤a≤0.9, 0≤b≤0.9, 0≤b2≤0.9, 0≤b3≤0.9, 0≤b4≤0.9, 0≤b5≤0.9, 0≤b6≤0.9, 0≤b7≤0.9, 0.1≤b1+b2+b3+b4+b5+b6+b7≤0.9, 0≤c≤0.8, and 0≤d≤0.8; more preferably 0.2≤a≤0.85, 0≤b1≤0.8, 0≤b2≤0.8, 0≤b3≤0.8, 0≤b4≤0.8, 0≤b5≤0.8, 0≤b6≤0.8, 0≤b7≤0.8, 0.15≤b1+b2+b3+b4+b5+b6+b7≤0.8, 0≤c≤0.7, and 0≤d≤0.7. Incidentally, it is particularly preferable that a+b1+b2+b3+b4+b5+b6+b7+c+d=1.

In the inventive method for producing a polymer compound for a conductive polymer, after the monomers are polymerized as described above, one or more selected from structures of salts among lithium, sodium, potassium, a nitrogen compound of a fluorosulfonic acid, a fluorosulfonimide group, or a n-carbonyl-fluoro-sulfonamide group are changed to the fluorosulfonic acid, the fluorosulfonimide group, or the n-carbonyl-fluoro-sulfonamide group by ion exchange. In this event, the ion exchange can be carried out, for example, by using an ion exchange resin.

According to the method as shown above, the polymer compound for a conductive polymer can be produced easily which contains: the repeating unit "a" shown by the general formula (2); and at least one repeating unit "b" selected from repeating units of monomers respectively having a fluorosulfonic acid, a fluorosulfonimide group, and a n-carbonyl-fluoro-sulfonamide group, for example, the repeating units b1 to b7 shown by the general formula (3).

EXAMPLE

Hereinafter, the present invention will be specifically described with reference to Examples, but the present invention is not limited thereto.

[Synthesis Example 1-1] Synthesis of Monomer a1

Under nitrogen atmosphere, Raw material 1 (120 g) and Raw material 2 (352 g) were prepared and suspended in toluene (400 g) and tetrahydrofuran (THF) (400 g), and cooled in an ice bath. Then, a 25 mass % sodium hydroxide aqueous solution (160 g) was added dropwise with the inner temperature at 15° C. or less. After the dropwise addition, the temperature was increased to room temperature for aging for 12 hours. After the aging, the reaction system was cooled, and 20 mass % hydrochloric acid (182 g) was added dropwise to terminate the reaction. Subsequently, toluene (500 g) was added for extraction, followed by common aqueous post-treatment (aqueous work-up). After the solvent was distilled off, the resultant was purified by distillation (boiling point: 65° C./20 Pa). Thus, 183 g of Monomer a1 was obtained as a colorless transparent oil (yield: 61%).

[Synthesis Example 1-2] Synthesis of Monomer a2

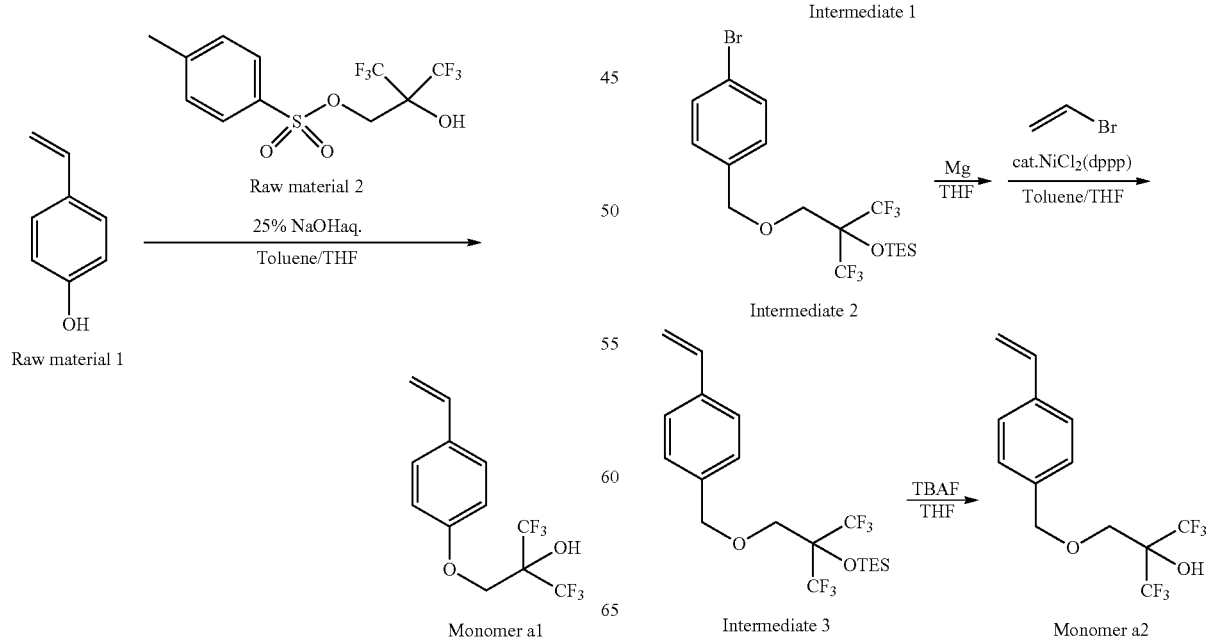

[Synthesis Example 1-2-1] Synthesis of Intermediate 1

Under nitrogen atmosphere, a THF (150 ml) solution of Raw material 3 (93 g) was added dropwise to a THF (200 ml) solution of sodium hydride (27.2 g, 55 mass %) with the inner temperature of approximately 50° C., followed by stirring at 80° C. for 6 hours. Then, the reaction solution was cooled to 10° C., and Raw material 4 (108 g) was added dropwise thereto. After the dropwise addition, the mixture was aged for 12 hours with the inner temperature of 35° C. After the aging, the reaction solution was cooled, and the reaction was terminated using a saturated ammonium chloride aqueous solution (150 g). Toluene (500 ml) was added for extraction, followed by common aqueous post-treatment (aqueous work-up). After the solvent was distilled off, the resultant was distilled under reduced pressure. Thus, 170 g of Intermediate 1 was obtained as a colorless transparent oil (yield: 93%).

[Synthesis Example 1-2-2] Synthesis of Intermediate 2

Under nitrogen atmosphere, Intermediate 1 (165 g), imidazole (46 g), and N,N-dimethylformamide (DMF) (500 g) were introduced into a flask, which was then cooled in an ice bath. Subsequently, triethylsilyl chloride (81 g) was added dropwise. After the dropwise addition, the temperature was increased to room temperature for aging for 12 hours. After the aging, the reaction liquid was ice-cooled, and saturated baking soda solution (500 g) was added dropwise to terminate the reaction. After extraction with hexane (800 ml), common aqueous post-treatment (aqueous work-up) was performed. After the solvent was distilled off, the resultant was purified by silica gel column chromatography. Thus, 210 g of Intermediate 2 was obtained as a colorless transparent oil (yield: 97%).

[Synthesis Example 1-2-3] Synthesis of Intermediate 3

Under nitrogen atmosphere, a Grignard reagent was prepared from magnesium (10.2 g), Intermediate 2 (192 g), and THF (400 g). The prepared Grignard reagent was diluted with toluene (200 g), and cooled in an ice bath. Further, [1,3-bis(diphenylphosphino)propane]nickel(II) dichloride (1.1 g) was added thereto, and the mixture was aged for 30 minutes. While the system was cooled in an ice bath, a solution of vinyl bromide (52 g), THF (100 g), and toluene (100 g) was added dropwise with the inner temperature being maintained at 20° C. or less. After the dropwise addition, the mixture was aged in an ice bath for 1 hour. After the aging, a solution of ammonium chloride (40 g), 20 mass % hydrochloric acid (40 g), and water (200 g) was added dropwise to terminate the reaction. After extraction with hexane (800 ml), common aqueous post-treatment (aqueous work-up) was performed. After the solvent was distilled off, the resultant was purified by silica gel column chromatography. Thus, 146 g of Intermediate 3 was obtained as a colorless transparent oil (yield: 85%).

[Synthesis Example 1-2-4] Synthesis of Monomer a2

Under nitrogen atmosphere, Intermediate 3 (129 g) was dissolved in THF (260 ml), and cooled in an ice bath. Then, tetrabutylammonium fluoride (300 g, 1 mol/L THF solution) was added dropwise with the inner temperature at 20° C. or less. After the dropwise addition, the mixture was further aged for 1 hour. After the aging, the reaction liquid was cooled in an ice bath, and water (500 g) was added to terminate the reaction. After extraction with toluene (500 g), common aqueous post-treatment (aqueous work-up) was performed. After the solvent was distilled off, the resultant was purified by silica gel column chromatography. Thus, 91 g of Monomer a2 was obtained as a colorless transparent oil (yield: 97%).

Monomers used in Examples are shown below.

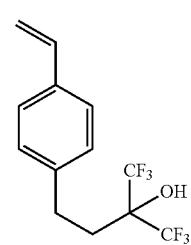

Monomer a1

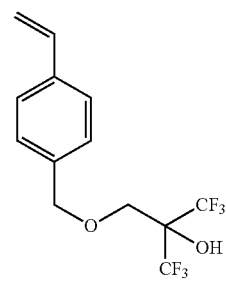

Monomer a2

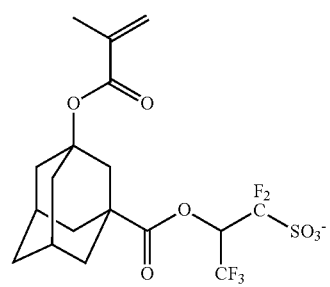

Monomer b1-1

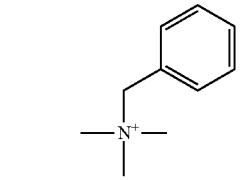

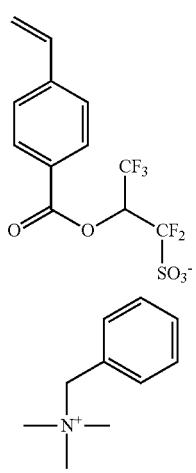

Monomer b1-2

Monomer b2-1

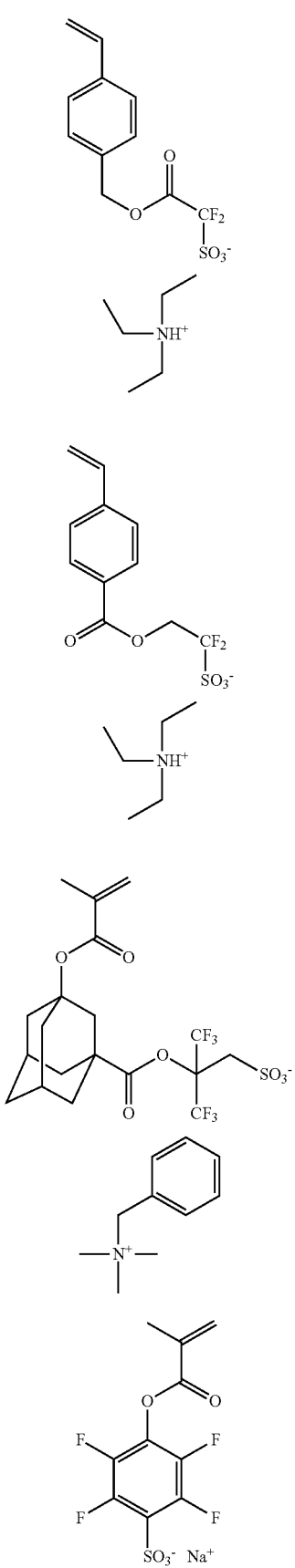

Monomer b3-1

Monomer b4-1

Monomer b5-1

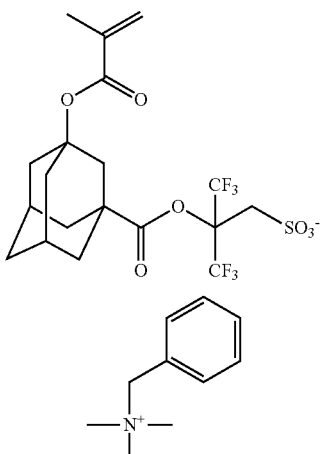

Monomer b6-1

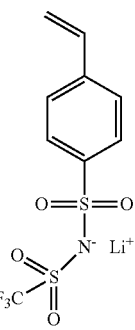

Monomer b7-1

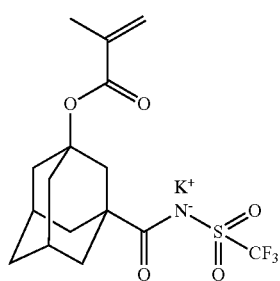

Monomer b7-2

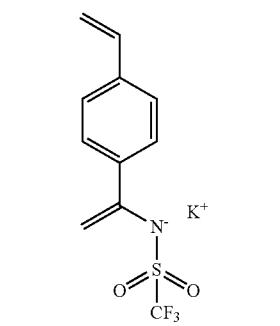

Example 1

Under nitrogen atmosphere, to 10 g of methanol stirred at 64° C. was added dropwise over 4 hours a solution of 1.20 g of Monomer a1, 3.75 g of Monomer b1-1, and 0.12 g of dimethyl 2,2'-azobis(isobutyrate) dissolved in 3 g of methanol. The mixture was further stirred at 64° C. for 4 hours. After cooled to room temperature, the reaction solution was added dropwise to 10 g of ethyl acetate under vigorous stirring. The formed solid product was collected by filtration, and dried under vacuum at 50° C. for 15 hours to obtain a white polymer.

The obtained white polymer was dissolved in 100 g of pure water, and the ammonium salt was changed to a sulfo group by using an ion exchange resin. When the obtained polymer was measured by $^{19}F$-, $^{1}H$-NMR and GPC, the following analytical results were obtained.

Weight average molecular weight (Mw)=21,000

Molecular weight distribution (Mw/Mn)=1.90

This polymer compound is made (Polymer 1).

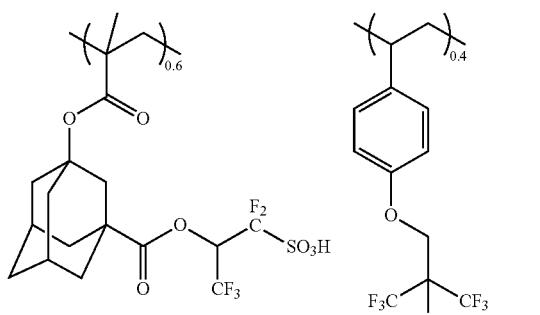

Polymer 1

Example 2

Under nitrogen atmosphere, to 10 g of methanol stirred at 64° C. was added dropwise over 4 hours a solution of 1.51 g of Monomer a1, 2.55 g of Monomer b1-2, and 0.12 g of dimethyl 2,2'-azobis(isobutyrate) dissolved in 3 g of methanol. The mixture was further stirred at 64° C. for 4 hours. After cooled to room temperature, the reaction solution was added dropwise to 10 g of ethyl acetate under vigorous stirring. The formed solid product was collected by filtration, and dried under vacuum at 50° C. for 15 hours to obtain a white polymer.

The obtained white polymer was dissolved in 100 g of pure water, and the ammonium salt was changed to a sulfo group by using an ion exchange resin. When the obtained polymer was measured by $^{19}$F-, $^{1}$H-NMR and GPC, the following analytical results were obtained.

Weight average molecular weight (Mw)=22,000
Molecular weight distribution (Mw/Mn)=1.93
This polymer compound is made (Polymer 2).

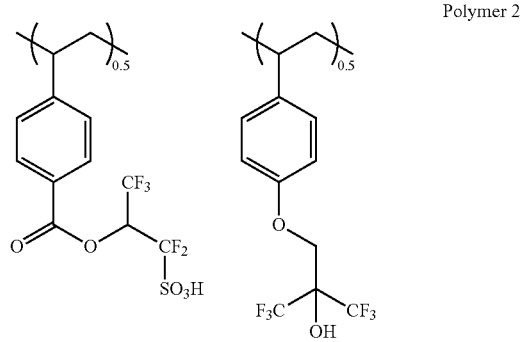

Polymer 2

Example 3

Under nitrogen atmosphere, to 10 g of methanol stirred at 64° C. was added dropwise over 4 hours a solution of 1.57 g of Monomer a2, 2.55 g of Monomer b1-2, and 0.12 g of dimethyl 2,2'-azobis(isobutyrate) dissolved in 3 g of methanol. The mixture was further stirred at 64° C. for 4 hours. After cooled to room temperature, the reaction solution was added dropwise to 10 g of ethyl acetate under vigorous stirring. The formed solid product was collected by filtration, and dried under vacuum at 50° C. for 15 hours to obtain a white polymer.

The obtained white polymer was dissolved in 100 g of pure water, and the ammonium salt was changed to a sulfo group by using an ion exchange resin. When the obtained polymer was measured by $^{19}$F-, $^{1}$H-NMR and GPC, the following analytical results were obtained.

Weight average molecular weight (Mw)=26,000
Molecular weight distribution (Mw/Mn)=1.99
This polymer compound is made (Polymer 3).

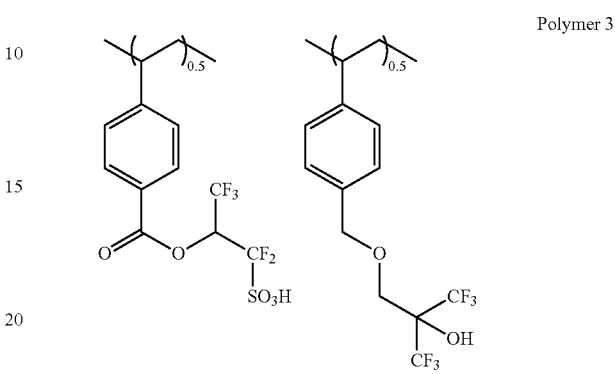

Polymer 3

Example 4

Under nitrogen atmosphere, to 10 g of methanol stirred at 64° C. was added dropwise over 4 hours a solution of 1.51 g of Monomer a1, 1.97 g of Monomer b2-1, and 0.12 g of dimethyl 2,2'-azobis(isobutyrate) dissolved in 3 g of methanol. The mixture was further stirred at 64° C. for 4 hours. After cooled to room temperature, the reaction solution was added dropwise to 10 g of ethyl acetate under vigorous stirring. The formed solid product was collected by filtration, and dried under vacuum at 50° C. for 15 hours to obtain a white polymer.

The obtained white polymer was dissolved in 100 g of pure water, and the ammonium salt was changed to a sulfo group by using an ion exchange resin. When the obtained polymer was measured by $^{19}$F-, $^{1}$H-NMR and GPC, the following analytical results were obtained.

Weight average molecular weight (Mw)=19,000
Molecular weight distribution (Mw/Mn)=1.61
This polymer compound is made (Polymer 4).

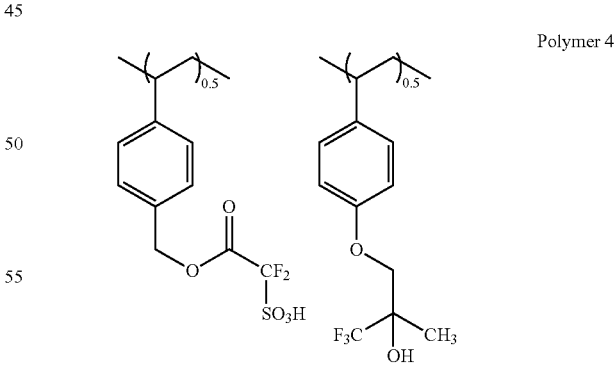

Polymer 4

Example 5

Under nitrogen atmosphere, to 10 g of methanol stirred at 65° C. was added dropwise over 4 hours a solution of 1.51 g of Monomer a1, 1.97 g of Monomer b3-1, and 0.12 g of dimethyl 2,2'-azobis(isobutyrate) dissolved in 3 g of methanol. The mixture was further stirred at 64° C. for 4 hours.

After cooled to room temperature, the reaction solution was added dropwise to 10 g of ethyl acetate under vigorous stirring. The formed solid product was collected by filtration, and dried under vacuum at 50° C. for 15 hours to obtain a white polymer.

The obtained white polymer was dissolved in 100 g of pure water, and the ammonium salt was changed to a sulfo group by using an ion exchange resin. When the obtained polymer was measured by $^{19}$F-, $^1$H-NMR and GPC, the following analytical results were obtained.

Weight average molecular weight (Mw)=18,000
Molecular weight distribution (Mw/Mn)=1.68
This polymer compound is made (Polymer 5).

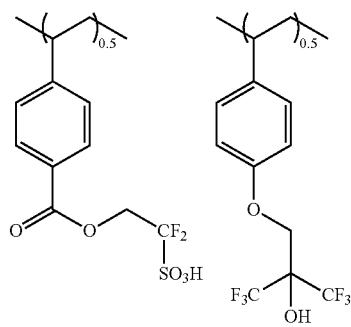

Polymer 5

Example 6

Under nitrogen atmosphere, to 10 g of methanol stirred at 64° C. was added dropwise over 4 hours a solution of 0.90 g of Monomer a1, 4.60 g of Monomer b4-1, and 0.12 g of dimethyl 2,2'-azobis(isobutyrate) dissolved in 3 g of methanol. The mixture was further stirred at 64° C. for 4 hours. After cooled to room temperature, the reaction solution was added dropwise to 10 g of ethyl acetate under vigorous stirring. The formed solid product was collected by filtration, and dried under vacuum at 50° C. for 15 hours to obtain a white polymer.

The obtained white polymer was dissolved in 100 g of pure water, and the ammonium salt was changed to a sulfo group by using an ion exchange resin. When the obtained polymer was measured by $^{19}$F-, $^1$H-NMR and GPC, the following analytical results were obtained.

Weight average molecular weight (Mw)=26,000
Molecular weight distribution (Mw/Mn)=2.04
This polymer compound is made (Polymer 6).

Polymer 6

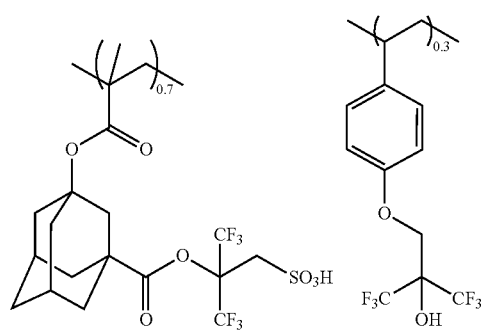

Example 7

Under nitrogen atmosphere, to 10 g of methanol stirred at 64° C. was added dropwise over 4 hours a solution of 0.90 g of Monomer a1, 2.35 g of Monomer b5-1, and 0.12 g of dimethyl 2,2'-azobis(isobutyrate) dissolved in 3 g of methanol. The mixture was further stirred at 64° C. for 4 hours. After cooled to room temperature, the reaction solution was added dropwise to 10 g of ethyl acetate under vigorous stirring. The formed solid product was collected by filtration, and dried under vacuum at 50° C. for 15 hours to obtain a white polymer.

The obtained white polymer was dissolved in 100 g of pure water, and the sodium salt was changed to a sulfo group by using an ion exchange resin. When the obtained polymer was measured by $^{19}$F-, $^1$H-NMR and GPC, the following analytical results were obtained.

Weight average molecular weight (Mw)=31,000
Molecular weight distribution (Mw/Mn)=2.11
This polymer compound is made (Polymer 7).

Polymer 7

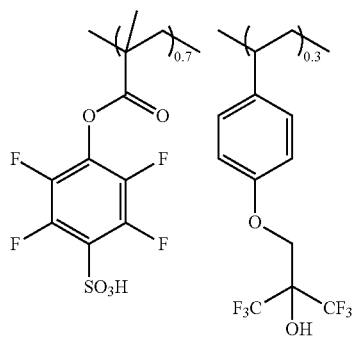

Example 8

Under nitrogen atmosphere, to 10 g of methanol stirred at 64° C. was added dropwise over 4 hours a solution of 1.20 g of Monomer a1, 1.93 g of Monomer b6-1, and 0.12 g of dimethyl 2,2'-azobis(isobutyrate) dissolved in 3 g of methanol. The mixture was further stirred at 64° C. for 4 hours. After cooled to room temperature, the reaction solution was added dropwise to 10 g of ethyl acetate under vigorous stirring. The formed solid product was collected by filtration, and dried under vacuum at 50° C. for 15 hours to obtain a white polymer.

The obtained white polymer was dissolved in 100 g of pure water, and the lithium salt was changed to a sulfonimide group by using an ion exchange resin. When the obtained polymer was measured by $^{19}$F-, $^1$H-NMR and GPC, the following analytical results were obtained.

Weight average molecular weight (Mw)=23,000
Molecular weight distribution (Mw/Mn)=1.88
This polymer compound is made (Polymer 8).

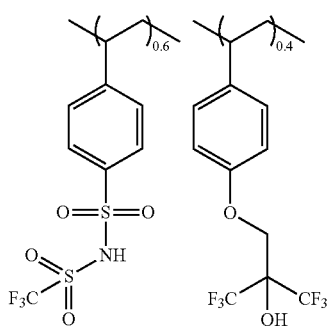

Polymer 8

Example 9

Under nitrogen atmosphere, to 10 g of methanol stirred at 64° C. was added dropwise over 4 hours a solution of 1.20 g of Monomer a1, 2.60 g of Monomer b7-1, and 0.12 g of dimethyl 2,2'-azobis(isobutyrate) dissolved in 3 g of methanol. The mixture was further stirred at 64° C. for 4 hours. After cooled to room temperature, the reaction solution was added dropwise to 10 g of ethyl acetate under vigorous stirring. The formed solid product was collected by filtration, and dried under vacuum at 50° C. for 15 hours to obtain a white polymer.

The obtained white polymer was dissolved in 100 g of pure water, and the potassium salt was changed to a n-carbonyl-sulfonamide group by using an ion exchange resin. When the obtained polymer was measured by 19F-, $^1$H-NMR and GPC, the following analytical results were obtained.

Weight average molecular weight (Mw)=29,000
Molecular weight distribution (Mw/Mn)=1.66
This polymer compound is made (Polymer 9).

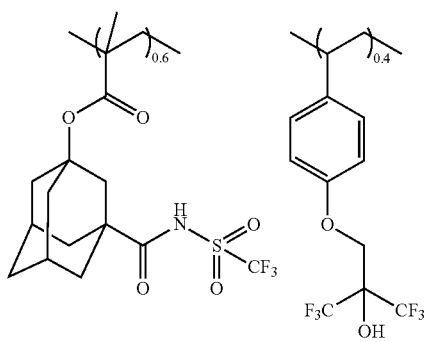

Polymer 9

Example 10

Under nitrogen atmosphere, to 10 g of methanol stirred at 64° C. was added dropwise over 4 hours a solution of 1.20 g of Monomer a1, 1.90 g of Monomer b7-2, and 0.12 g of dimethyl 2,2'-azobis(isobutyrate) dissolved in 3 g of methanol. The mixture was further stirred at 64° C. for 4 hours. After cooled to room temperature, the reaction solution was added dropwise to 10 g of ethyl acetate under vigorous stirring. The formed solid product was collected by filtration, and dried under vacuum at 50° C. for 15 hours to obtain a white polymer.

The obtained white polymer was dissolved in 100 g of pure water, and the potassium salt was changed to a n-carbonyl-sulfonamide group by using an ion exchange resin. When the obtained polymer was measured by $^{19}$F-, $^1$H-NMR and GPC, the following analytical results were obtained.

Weight average molecular weight (Mw)=27,000
Molecular weight distribution (Mw/Mn)=1.61
This polymer compound is made (Polymer 10).

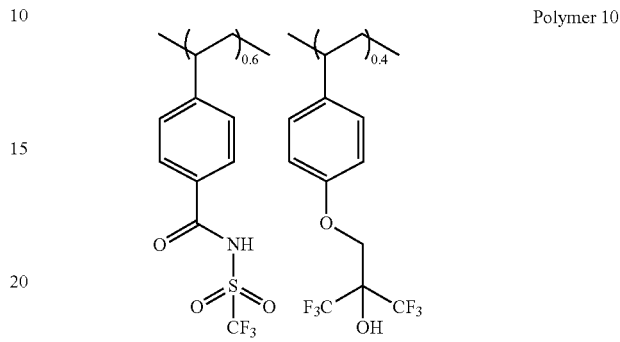

Polymer 10

It should be noted that the present invention is not limited to the above-described embodiments. The embodiments are just examples, and any examples that have substantially the same feature and demonstrate the same functions and effects as those in the technical concept disclosed in claims of the present invention are included in the technical scope of the present invention.

The invention claimed is:

1. A polymer compound for a conductive polymer, comprising a copolymer containing:
    a repeating unit shown by the following general formula (2); and
    at least one repeating unit "b" selected from repeating units of monomers respectively having a fluorosulfonic acid, a fluorosulfonimide group, a n-carbonyl-fluoro-sulfonamide group and repeating units of monomers each having a structure of a salt among a lithium salt, a sodium salt, a potassium salt, and a nitrogen compound salt of a fluorosulfonic acid, a fluorosulfonimide group, and a n-carbonyl-fluoro-sulfonamide group,
    wherein the polymer compound for a conductive polymer has a weight average molecular weight in a range of 1,000 to 500,000,

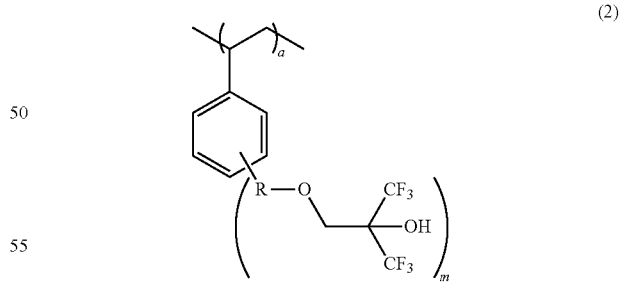

(2)

wherein R represents a single bond, a methylene group, or an ethylidene group; "m" represents 1 or 2; and "a" represents a molar ratio based on all repeating units in the polymer compound, and 0<a<1.0.

2. The polymer compound for a conductive polymer according to claim 1, wherein the repeating unit of a monomer having a fluorosulfonic acid is shown by any of b1 to b5, the repeating unit having a fluorosulfonimide group is shown by b6, and the repeating unit having a n-carbonyl-fluoro-sulfonamide group is shown by b7 in the following general formula (3):

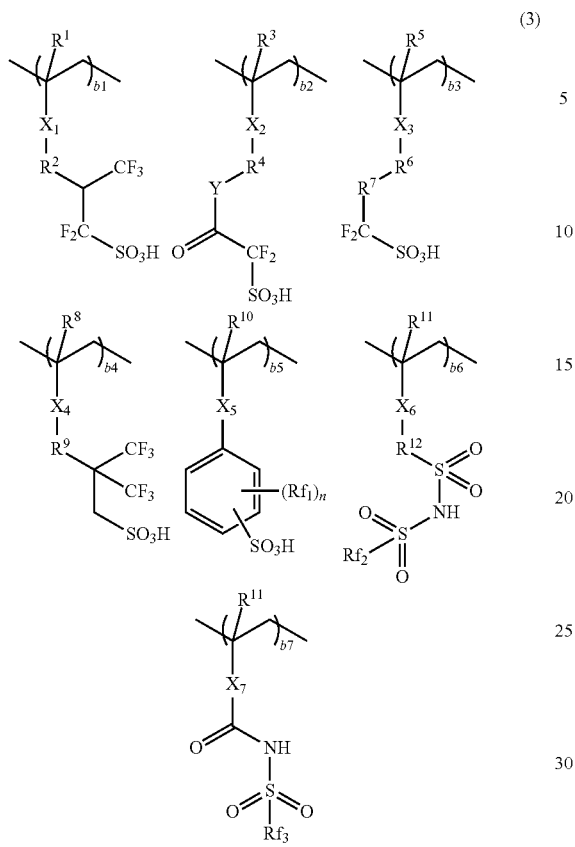

(3)

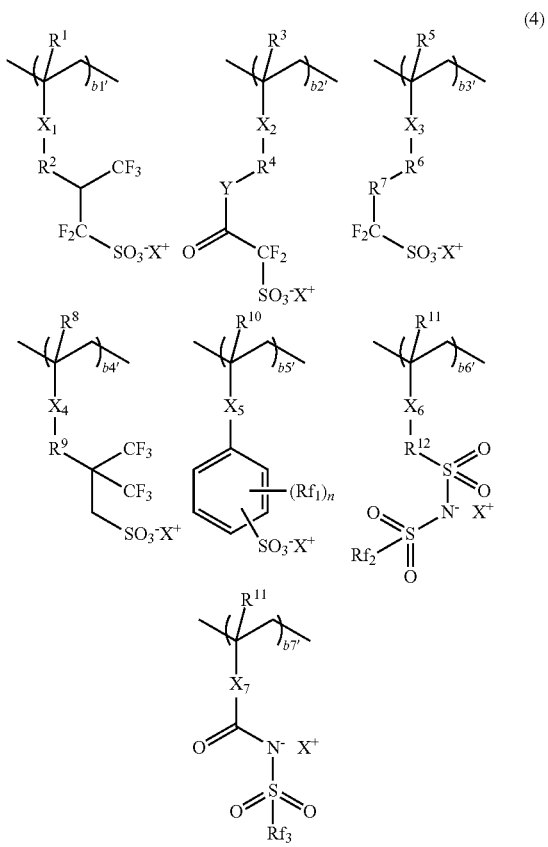

(4)

wherein $R^1$, $R^3$, $R^5$, $R^8$, $R^{10}$, $R^{11}$, and $R^{13}$ each independently represent a hydrogen atom or a methyl group; $R^2$, $R^4$, $R^6$, $R^9$, and $R^{12}$ each independently represent any of a single bond and a linear, branched, or cyclic hydrocarbon group having 1 to 12 carbon atoms optionally having one or both of an ether group and an ester group; $R^7$ represents a linear or branched alkylene group having 1 to 4 carbon atoms, and one or two hydrogen atoms in $R^7$ are optionally substituted with a fluorine atom; $X_1$, $X_2$, $X_3$, $X_4$, $X_6$, and $X_7$ each independently represent any of a single bond, a phenylene group, a naphthylene group, an ether group, an ester group, and an amide group; $X_5$ represents any of a single bond, an ether group, and an ester group; Y represents any of an ether group and an amino group which optionally contains any of a hydrogen atom and a linear, branched, or cyclic hydrocarbon group having 1 to 12 carbon atoms optionally containing a hetero atom; $Rf_1$ represents a fluorine atom or a trifluoromethyl group; $Rf_2$ and $Rf_3$ each represent a linear or branched alkyl group having 1 to 4 carbon atoms with one or more fluorine atoms, or a phenyl group substituted with a fluorine atom or a trifluoromethyl group; "n" represents an integer of 1 to 4; and b1, b2, b3, b4, b5, b6, and b7 represent a molar ratio based on all repeating units in the polymer compound, and satisfy $0 \leq b1 < 1.0$, $0 \leq b2 < 1.0$, $0 \leq b3 < 1.0$, $0 \leq b4 < 1.0$, $0 \leq b5 < 1.0$, $0 \leq b6 < 1.0$, $0 \leq b7 < 1.0$, and $0 < b1+b2+b3+b4+b5+b6+b7 < 1.0$.

3. The polymer compound for a conductive polymer according to claim 1, wherein the repeating unit of a monomer having a structure of a salt among a lithium salt, a sodium salt, a potassium salt, and a nitrogen compound salt of a fluorosulfonic acid, a fluorosulfonimide group, or a n-carbonyl-fluoro-sulfonamide group is any of repeating units b1' to b7' shown by the following general formula (4):

wherein $R^1$, $R^3$, $R^5$, $R^8$, $R^{10}$, $R^{11}$, and $R^{13}$ each independently represent a hydrogen atom or a methyl group; $R^2$, $R^4$, $R^6$, $R^9$, and $R^{12}$ each independently represent any of a single bond and a linear, branched, or cyclic hydrocarbon group having 1 to 12 carbon atoms optionally having one or both of an ether group and an ester group; $R^7$ represents a linear or branched alkylene group having 1 to 4 carbon atoms, and one or two hydrogen atoms in $R^7$ are optionally substituted with a fluorine atom; $X_1$, $X_2$, $X_3$, $X_4$, $X_6$, and $X_7$ each independently represent any of a single bond, a phenylene group, a naphthylene group, an ether group, an ester group, and an amide group; $X_5$ represents any of a single bond, an ether group, and an ester group; Y represents any of an ether group and an amino group which optionally contains any of a hydrogen atom and a linear, branched, or cyclic hydrocarbon group having 1 to 12 carbon atoms optionally containing a hetero atom; $Rf_1$ represents a fluorine atom or a trifluoromethyl group; $Rf_2$ and $Rf_3$ each represent a linear or branched alkyl group having 1 to 4 carbon atoms with one or more fluorine atoms, or a phenyl group substituted with a fluorine atom or a trifluoromethyl group; "n" represents an integer of 1 to 4; X represents lithium, sodium, potassium, or a nitrogen compound shown by the following general formula (5); and b1', b2', b3', b4', b5', b6', and b7' represent a molar ratio based on all repeating units in the polymer compound, and satisfy $0 \leq b1' < 1.0$, $0 \leq b2' < 1.0$, $0 \leq b3' < 1.0$, $0 \leq b4' < 1.0$, $0 \leq b5' < 1.0$, $0 \leq b6' < 1.0$, $0 \leq b7' < 1.0$, and $0 < b1'+b2'+b3'+b4'+b5'+b6'+b7' < 1.0$,

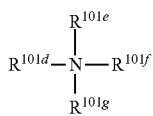
(5)

wherein $R^{101d}$, $R^{101e}$, $R^{101f}$, and $R^{101g}$ each represent a hydrogen atom, a linear, branched, or cyclic alkyl group, alkenyl group, oxoalkyl group, or oxoalkenyl group having 1 to 12 carbon atoms, an aryl group having 6 to 20 carbon atoms, or an aralkyl group or aryloxoalkyl group having 7 to 12 carbon atoms, and a part or all of hydrogen atoms of these groups are optionally substituted with alkoxy groups; and $R^{101d}$, $R^{101e}$, or $R^{101d}$, $R^{101e}$, and $R^{101f}$, optionally form a ring, and when a ring is formed, $R^{101d}$, $R^{101e}$, or $R^{101d}$, $R^{101e}$, and $R^{101f}$, represent an alkylene group having 3 to 10 carbon atoms or a heteroaromatic ring having the nitrogen atom in the formula in the ring.

4. A method for producing a polymer compound for a conductive polymer, comprising:

performing polymerization reaction using a polymerizable monomer shown by the following general formula (1) and at least one monomer selected from monomers each having a structure of a salt among a lithium salt, a sodium salt, a potassium salt, and a nitrogen compound salt of a fluorosulfonic acid, a fluorosulfonimide group, and a n-carbonyl-fluoro-sulfonamide group,

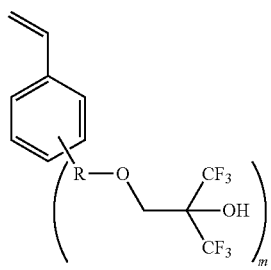
(1)

wherein R represents a single bond, a methylene group, or an ethylidene group, and "m" represents 1 or 2; and changing the structure of the salt of the monomer as a repeating unit of a polymer obtained by the polymerization reaction to the fluorosulfonic acid, the fluorosulfonimide group, or the n-carbonyl-fluoro-sulfonamide group by ion exchange, wherein the polymer compound for a conductive polymer comprises a copolymer containing a repeating unit "a" shown by the following general formula (2) and at least one repeating unit "b" selected from repeating units of monomers respectively having the fluorosulfonic acid, the fluorosulfonimide group, and the n-carbonyl-fluoro-sulfonamide group, and has a weight average molecular weight in a range of 1,000 to 500,000,

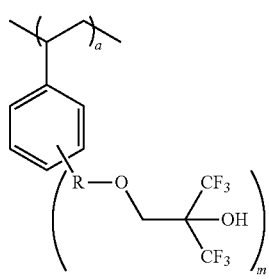
(2)

wherein R and "m" are as defined above, and "a" represents a molar ratio based on all repeating units in the polymer compound, and 0<a<1.0.

* * * * *